(12) United States Patent
Uchida et al.

(10) Patent No.: US 11,307,208 B2
(45) Date of Patent: Apr. 19, 2022

(54) BIOMARKERS FOR COGNITIVE IMPAIRMENT AND METHODS FOR DETECTING COGNITIVE IMPAIRMENT USING SUCH BIOMARKERS

(71) Applicant: MCBI INC., Tsukuba (JP)

(72) Inventors: Kazuhiko Uchida, Tsukuba (JP); Kohji Meno, Tsukuba (JP); Hideaki Suzuki, Tsukuba (JP)

(73) Assignee: MCBI, Inc., Tsukuba (JP)

( * ) Notice: Subject to any disclaimer, the term of this patent is extended or adjusted under 35 U.S.C. 154(b) by 0 days.

(21) Appl. No.: 16/791,984

(22) Filed: Feb. 14, 2020

(65) Prior Publication Data

US 2020/0200768 A1 Jun. 25, 2020

Related U.S. Application Data

(63) Continuation of application No. 15/639,735, filed on Jun. 30, 2017, now abandoned, which is a (Continued)

(30) Foreign Application Priority Data

Dec. 22, 2010 (JP) .................................. 2010-285726

(51) Int. Cl.
*G01N 33/48* (2006.01)
*C07K 14/435* (2006.01)
(Continued)

(52) U.S. Cl.
CPC ......... *G01N 33/6896* (2013.01); *C07K 16/40* (2013.01); *G01N 2333/974* (2013.01); (Continued)

(58) Field of Classification Search
None
See application file for complete search history.

(56) References Cited

U.S. PATENT DOCUMENTS

| 2002/0104104 A1 | 8/2002 | Games et al. |
| 2003/0100016 A1 | 5/2003 | Jackowski et al. |

(Continued)

FOREIGN PATENT DOCUMENTS

| EP | 0 582 450 A2 | 2/1994 |
| JP | 11-507821 A | 7/1999 |

(Continued)

OTHER PUBLICATIONS

Benkirane et al., "Antigenicity and Immunogenicity of Modified Synthetic Peptides Containing D-Amino Acid Residues", The Journal of Biological Chemistry, vol. 268, No. 35, pp. 26279-26285, 1993.

(Continued)

*Primary Examiner* — Aurora M Fontainhas
(74) *Attorney, Agent, or Firm* — Birch, Stewart, Kolasch & Birch, LLP

(57) ABSTRACT

The present invention aims to provide methods to detect cognitive impairment including mild cognitive impairment and Alzheimer disease by using a protein or its partial peptide that differs in presence or absence, or in quantity between non-cognitive impairment and patients with cognitive impairment and further aims to present biomarkers comprising said protein and said partial peptide to be used to detect cognitive impairment including Alzheimer disease or mild cognitive impairment. Specifically, a biomarker for diagnosis of psychiatry disease or cognitive impairment comprising protein fragment or peptide of not less than 5 amino acid residues arising from at least one protein or peptide selected from the group of proteins consisting of amino acid sequence expressed by SEQ ID NOS: 1, 3, 5, 7, (Continued)

9, 11, 13, 15, 17, 19, 21, 23, and 25 and selected from the group of partial peptide in these proteins consisting of amino acid sequence expressed by SEQ ID NOS: 2, 4, 6, 8, 10, 12, 14, 16, 18, 20, 22, 24, 26, and 27. And further aims to provide diagnostic method using these biomarker.

3 Claims, 17 Drawing Sheets

Specification includes a Sequence Listing.

Related U.S. Application Data continuation of application No. 15/467,646, filed on Mar. 23, 2017, now abandoned, which is a continuation of application No. 14/582,778, filed on Dec. 24, 2014, now abandoned, which is a continuation of application No. 13/995,682, filed as application No. PCT/JP2011/007150 on Dec. 21, 2011, now abandoned.

(51) Int. Cl.
  *A61K 39/00* (2006.01)
  *G01N 33/68* (2006.01)
  *C07K 16/40* (2006.01)

(52) U.S. Cl.
  CPC ......... *G01N 2800/2814* (2013.01); *G01N 2800/2821* (2013.01); *G01N 2800/60* (2013.01)

(56) References Cited

U.S. PATENT DOCUMENTS

| | | |
|---|---|---|
| 2004/0265825 A1 | 12/2004 | Tartakovsky |
| 2005/0048584 A1 | 3/2005 | Lamping et al. |
| 2006/0014147 A1 | 1/2006 | Golz |
| 2008/0070995 A1 | 3/2008 | Westbrook et al. |
| 2009/0130060 A1 | 5/2009 | Weimer et al. |
| 2010/0167937 A1 | 7/2010 | Goldknopf et al. |
| 2012/0149034 A1 | 6/2012 | Uchida et al. |

FOREIGN PATENT DOCUMENTS

| | | |
|---|---|---|
| JP | 2004-333274 A | 11/2004 |
| JP | 2005-511063 A | 4/2005 |
| JP | 2005-523420 A | 8/2005 |
| JP | 2006-308533 A | 11/2006 |
| JP | 2008-514946 A | 5/2008 |
| WO | WO 03/048775 A2 | 6/2003 |
| WO | WO 2005/047484 A2 | 5/2005 |
| WO | WO 2006/108051 A2 | 10/2006 |
| WO | WO 2007/132291 A2 | 11/2007 |
| WO | WO 2010/084327 A2 | 7/2010 |
| WO | WO 2010/134308 A1 | 11/2010 |

OTHER PUBLICATIONS

Ansubel et al., "Current protocols in molecular biology," Section II, Preparation of Monodonal Antibodies, Unit 11.4 to Unit 11.11, vol. 2, 1992.

Chen et al., "Crystal Structure of Prethrombin-1", PNAS, vol. 107, No. 45 (2010) pp. 19278-19283.

European Patent Office Communication and extended search report issued in the European Patent Application No. 18163415.5 dated Sep. 19, 2018.

Extended European Search Report for European Application No. 17178675.9, dated Oct. 2, 2017.

German et al., "Serum biomarkers for Alzheimer's disease: Proteomic discovery," Biomedicine & Pharmacotherapy, vol. 61, 2007 (Available online Jun. 18, 2007), pp. 383-389.

International Search Report, dated Mar. 19, 2012, issued in PCT/JP2011/007150.

Lopez et al., "High-Resolution Serum Proteomic Profiling of Alzheimer Disease Samples Reveals Disease-Specific, Carrier-Protein-Bound Mass Signatures," Clinical Chemistry, vol. 51, No. 10, XP008131749, 2005, pp. 1946-1954.

Mayilyan et al., "The complement system in schizophrenia," Drug News & Perspectives, vol. 21, No. 4, May 2008, pp. 200-210.

Nakano et al., "The better understanding of Alzheimer's disease", Nagai Shoten Co., Ltd., pp. 33-34, 72-73, 82-83, 107, 115-116 and 145, 2004.

Rask et al., "Anti-prothrombin Antibodies are Associated with Thrombosis in Children", Thrombosis Research, vol. 125 (2010) pp. 19-24.

Stott et al., "Activation of Hemostasis and Decline in Cognitive Function in Older People", Arterioscler Thromb Vasc Biol, vol. 30 (2010—originally published online Dec. 23, 2009), pp. 605-611.

Rozek et al., "Sera proteomic biomarker profiling in HIV-1 infected subjects with cognitive impairment," Proteomics—Clinical Applications, vol. 2, 2008, pp. 1498-1507.

Zipser et al., "Microvascular injury and blood-brain barrier leakage in Alzheimer's disease," Neurobiol Aging, vol. 28, No. 7, Jul. 2007 (available online Jun. 16, 2006), pp. 977-986.

SEQUENCE LISTING

```
<160> NUMBER OF SEQ ID NOS: 27

<210> SEQ ID NO 1
<211> LENGTH: 1641
<212> TYPE: PRT
<213> ORGANISM: Homo sapiens

<400> SEQUENCE: 1

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
            180                 185                 190
```

```
Gln Gln Val Phe Ser Thr Glu Phe Glu Val Lys Glu Tyr Val Leu Pro
    195                 200                 205

Ser Phe Glu Val Ile Val Glu Pro Thr Glu Lys Phe Tyr Tyr Ile Tyr
210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Pro Arg Ala Glu Asp Leu Val Gly Lys Ser Leu Tyr Val
    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
        355                 360                 365

Val Gln Gly Glu Asp Thr Val Gln Ser Leu Thr Gln Gly Asp Gly Val
    370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415

Arg Thr Met Gln Ala Leu Pro Tyr Ser Thr Val Gly Asn Ser Asn Asn
            420                 425                 430

Tyr Leu His Leu Ser Val Leu Arg Thr Glu Leu Arg Pro Gly Glu Thr
        435                 440                 445

Leu Asn Val Asn Phe Leu Leu Arg Met Asp Arg Ala His Glu Ala Lys
    450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
            500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
            580                 585                 590

Lys Ile Trp Asp Val Val Glu Lys Ala Asp Ile Gly Cys Thr Pro Gly
        595                 600                 605

Ser Gly Lys Asp Tyr Ala Gly Val Phe Ser Asp Ala Gly Leu Thr Phe
```

-continued

```
            610                 615                 620
Thr Ser Ser Ser Gly Gln Gln Thr Ala Gln Arg Ala Glu Leu Gln Cys
625                 630                 635                 640

Pro Gln Pro Ala Ala Arg Arg Arg Ser Val Gln Leu Thr Glu Lys
                645                 650                 655

Arg Met Asp Lys Val Gly Lys Tyr Pro Lys Glu Leu Arg Lys Cys Cys
                660                 665                 670

Glu Asp Gly Met Arg Glu Asn Pro Met Arg Phe Ser Cys Gln Arg Arg
                675                 680                 685

Thr Arg Phe Ile Ser Leu Gly Glu Ala Cys Lys Lys Val Phe Leu Asp
                690                 695                 700

Cys Cys Asn Tyr Ile Thr Glu Leu Arg Arg Gln His Ala Arg Ala Ser
705                 710                 715                 720

His Leu Gly Leu Ala Arg Ser Asn Leu Asp Glu Asp Ile Ile Ala Glu
                725                 730                 735

Glu Asn Ile Val Ser Arg Ser Glu Phe Pro Glu Ser Trp Leu Trp Asn
                740                 745                 750

Val Glu Asp Leu Lys Glu Pro Pro Lys Asn Gly Ile Ser Thr Lys Leu
                755                 760                 765

Met Asn Ile Phe Leu Lys Asp Ser Ile Thr Thr Trp Glu Ile Leu Ala
770                 775                 780

Val Ser Met Ser Asp Lys Lys Gly Ile Cys Val Ala Asp Pro Phe Glu
785                 790                 795                 800

Val Thr Val Met Gln Asp Phe Phe Ile Asp Leu Arg Leu Pro Tyr Ser
                805                 810                 815

Val Val Arg Asn Glu Gln Val Glu Ile Arg Ala Val Leu Tyr Asn Tyr
                820                 825                 830

Arg Gln Asn Gln Glu Leu Lys Val Arg Val Glu Leu Leu His Asn Pro
                835                 840                 845

Ala Phe Cys Ser Leu Ala Thr Thr Lys Arg Arg His Gln Gln Thr Val
850                 855                 860

Thr Ile Pro Pro Lys Ser Ser Leu Ser Val Pro Tyr Val Ile Val Pro
865                 870                 875                 880

Leu Lys Thr Gly Leu Gln Glu Val Glu Val Lys Ala Ala Val Tyr His
                885                 890                 895

His Phe Ile Ser Asp Gly Val Arg Lys Ser Leu Lys Val Val Pro Glu
                900                 905                 910

Gly Ile Arg Met Asn Lys Thr Val Ala Val Arg Thr Leu Asp Pro Glu
                915                 920                 925

Arg Leu Gly Arg Glu Gly Val Gln Lys Glu Asp Ile Pro Pro Ala Asp
930                 935                 940

Leu Ser Asp Gln Val Pro Asp Thr Glu Ser Glu Thr Arg Ile Leu Leu
945                 950                 955                 960

Gln Gly Thr Pro Val Ala Gln Met Thr Glu Asp Ala Val Asp Ala Glu
                965                 970                 975

Arg Leu Lys His Leu Ile Val Thr Pro Ser Gly Cys Gly Glu Gln Asn
                980                 985                 990

Met Ile Gly Met Thr Pro Thr Val  Ile Ala Val His Tyr  Leu Asp Glu
                995                 1000                1005

Thr Glu  Gln Trp Glu Lys Phe  Gly Leu Glu Lys Arg  Gln Gly Ala
    1010                1015                1020

Leu Glu  Leu Ile Lys Lys Gly  Tyr Thr Gln Gln Leu  Ala Phe Arg
    1025                1030                1035
```

```
Gln Pro Ser Ser Ala Phe Ala Ala Phe Val Lys Arg Ala Pro Ser
    1040                1045                1050

Thr Trp Leu Thr Ala Tyr Val Val Lys Val Phe Ser Leu Ala Val
    1055                1060                1065

Asn Leu Ile Ala Ile Asp Ser Gln Val Leu Cys Gly Ala Val Lys
    1070                1075                1080

Trp Leu Ile Leu Glu Lys Gln Lys Pro Asp Gly Val Phe Gln Glu
    1085                1090                1095

Asp Ala Pro Val Ile His Gln Glu Met Ile Gly Gly Leu Arg Asn
    1100                1105                1110

Asn Asn Glu Lys Asp Met Ala Leu Thr Ala Phe Val Leu Ile Ser
    1115                1120                1125

Leu Gln Glu Ala Lys Asp Ile Cys Glu Glu Gln Val Asn Ser Leu
    1130                1135                1140

Pro Gly Ser Ile Thr Lys Ala Gly Asp Phe Leu Glu Ala Asn Tyr
    1145                1150                1155

Met Asn Leu Gln Arg Ser Tyr Thr Val Ala Ile Ala Gly Tyr Ala
    1160                1165                1170

Leu Ala Gln Met Gly Arg Leu Lys Gly Pro Leu Leu Asn Lys Phe
    1175                1180                1185

Leu Thr Thr Ala Lys Asp Lys Asn Arg Trp Glu Asp Pro Gly Lys
    1190                1195                1200

Gln Leu Tyr Asn Val Glu Ala Thr Ser Tyr Ala Leu Leu Ala Leu
    1205                1210                1215

Leu Gln Leu Lys Asp Phe Asp Phe Val Pro Pro Val Val Arg Trp
    1220                1225                1230

Leu Asn Glu Gln Arg Tyr Tyr Gly Gly Gly Tyr Gly Ser Thr Gln
    1235                1240                1245

Ala Thr Phe Met Val Phe Gln Ala Leu Ala Gln Tyr Gln Lys Asp
    1250                1255                1260

Ala Pro Asp His Gln Glu Leu Asn Leu Asp Val Ser Leu Gln Leu
    1265                1270                1275

Pro Ser Arg Ser Ser Lys Ile Thr His Arg Ile His Trp Glu Ser
    1280                1285                1290

Ala Ser Leu Leu Arg Ser Glu Glu Thr Lys Glu Asn Glu Gly Phe
    1295                1300                1305

Thr Val Thr Ala Glu Gly Lys Gly Gln Gly Thr Leu Ser Val Val
    1310                1315                1320

Thr Met Tyr His Ala Lys Ala Lys Asp Gln Leu Thr Cys Asn Lys
    1325                1330                1335

Phe Asp Leu Lys Val Thr Ile Lys Pro Ala Pro Glu Thr Glu Lys
    1340                1345                1350

Arg Pro Gln Asp Ala Lys Asn Thr Met Ile Leu Glu Ile Cys Thr
    1355                1360                1365

Arg Tyr Arg Gly Asp Gln Asp Ala Thr Met Ser Ile Leu Asp Ile
    1370                1375                1380

Ser Met Met Thr Gly Phe Ala Pro Asp Thr Asp Asp Leu Lys Gln
    1385                1390                1395

Leu Ala Asn Gly Val Asp Arg Tyr Ile Ser Lys Tyr Glu Leu Asp
    1400                1405                1410

Lys Ala Phe Ser Asp Arg Asn Thr Leu Ile Ile Tyr Leu Asp Lys
    1415                1420                1425
```

-continued

```
Val Ser His Ser Glu Asp Asp Cys Leu Ala Phe Lys Val His Gln
    1430                1435                1440

Tyr Phe Asn Val Glu Leu Ile Gln Pro Gly Ala Val Lys Val Tyr
    1445                1450                1455

Ala Tyr Tyr Asn Leu Glu Glu Ser Cys Thr Arg Phe Tyr His Pro
    1460                1465                1470

Glu Lys Glu Asp Gly Lys Leu Asn Lys Leu Cys Arg Asp Glu Leu
    1475                1480                1485

Cys Arg Cys Ala Glu Glu Asn Cys Phe Ile Gln Lys Ser Asp Asp
    1490                1495                1500

Lys Val Thr Leu Glu Glu Arg Leu Asp Lys Ala Cys Glu Pro Gly
    1505                1510                1515

Val Asp Tyr Val Tyr Lys Thr Arg Leu Val Lys Val Gln Leu Ser
    1520                1525                1530

Asn Asp Phe Asp Glu Tyr Ile Met Ala Ile Glu Gln Thr Ile Lys
    1535                1540                1545

Ser Gly Ser Asp Glu Val Gln Val Gly Gln Gln Arg Thr Phe Ile
    1550                1555                1560

Ser Pro Ile Lys Cys Arg Glu Ala Leu Lys Leu Glu Glu Lys Lys
    1565                1570                1575

His Tyr Leu Met Trp Gly Leu Ser Ser Asp Phe Trp Gly Glu Lys
    1580                1585                1590

Pro Asn Leu Ser Tyr Ile Ile Gly Lys Asp Thr Trp Val Glu His
    1595                1600                1605

Trp Pro Glu Glu Asp Glu Cys Gln Asp Glu Glu Asn Gln Lys Gln
    1610                1615                1620

Cys Gln Asp Leu Gly Ala Phe Thr Glu Ser Met Val Val Phe Gly
    1625                1630                1635

Cys Pro Asn
    1640

<210> SEQ ID NO 2
<211> LENGTH: 14
<212> TYPE: PRT
<213> ORGANISM: Homo sapiens

<400> SEQUENCE: 2

Ala Pro Val Ile His Gln Glu Met Ile Gly Gly Leu Arg Asn
1               5                   10

<210> SEQ ID NO 3
<211> LENGTH: 450
<212> TYPE: PRT
<213> ORGANISM: Homo sapiens

<400> SEQUENCE: 3

Met Leu Trp Lys Ile Thr Asp Asn Val Lys Tyr Glu Glu Asp Cys Glu
1               5                   10                  15

Asp Arg His Asp Gly Ser Ser Asn Gly Asn Pro Arg Val Pro His Leu
                20                  25                  30

Ser Ser Ala Gly Gln His Leu Tyr Ser Pro Ala Pro Pro Leu Ser His
            35                  40                  45

Thr Gly Val Ala Glu Tyr Gln Pro Pro Pro Tyr Phe Pro Pro Pro Tyr
        50                  55                  60

Gln Gln Leu Ala Tyr Ser Gln Ser Ala Asp Pro Tyr Ser His Leu Gly
65                  70                  75                  80
```

```
Glu Ala Tyr Ala Ala Ile Asn Pro Leu His Gln Pro Ala Pro Thr
                85                  90                  95

Gly Ser Gln Gln Gln Ala Trp Pro Gly Arg Gln Ser Gln Glu Gly Ala
            100                 105                 110

Gly Leu Pro Ser His His Gly Arg Pro Ala Gly Leu Leu Pro His Leu
            115                 120                 125

Ser Gly Leu Glu Ala Gly Ala Val Ser Ala Arg Arg Asp Ala Tyr Arg
            130                 135                 140

Arg Ser Asp Leu Leu Leu Pro His Ala His Ala Leu Asp Ala Ala Gly
145                 150                 155                 160

Leu Ala Glu Asn Leu Gly Leu His Asp Met Pro His Gln Met Asp Glu
                165                 170                 175

Val Gln Asn Val Asp Asp Gln His Leu Leu Leu His Asp Gln Thr Val
            180                 185                 190

Ile Arg Lys Gly Pro Ile Ser Met Thr Lys Asn Pro Leu Asn Leu Pro
            195                 200                 205

Cys Gln Lys Glu Leu Val Gly Ala Val Met Asn Pro Thr Glu Val Phe
    210                 215                 220

Cys Ser Val Pro Gly Arg Leu Ser Leu Leu Ser Ser Thr Ser Lys Tyr
225                 230                 235                 240

Lys Val Thr Val Ala Glu Val Gln Arg Arg Leu Ser Pro Pro Glu Cys
                245                 250                 255

Leu Asn Ala Ser Leu Leu Gly Gly Val Leu Arg Arg Ala Lys Ser Lys
            260                 265                 270

Asn Gly Gly Arg Ser Leu Arg Glu Lys Leu Asp Lys Ile Gly Leu Asn
            275                 280                 285

Leu Pro Ala Gly Arg Arg Lys Ala Ala His Val Thr Leu Leu Thr Ser
290                 295                 300

Leu Val Glu Gly Glu Ala Val His Leu Ala Arg Asp Phe Ala Tyr Val
305                 310                 315                 320

Cys Glu Ala Glu Phe Pro Ser Lys Pro Val Ala Glu Tyr Leu Thr Arg
                325                 330                 335

Pro His Leu Gly Gly Arg Asn Glu Met Ala Ala Arg Lys Asn Met Leu
            340                 345                 350

Leu Ala Ala Gln Gln Leu Cys Lys Glu Phe Thr Glu Leu Leu Ser Gln
            355                 360                 365

Asp Arg Thr Pro His Gly Thr Ser Arg Leu Ala Pro Val Leu Glu Thr
        370                 375                 380

Asn Ile Gln Asn Cys Leu Ser His Phe Ser Leu Ile Thr His Gly Phe
385                 390                 395                 400

Gly Ser Gln Ala Ile Cys Ala Ala Val Ser Ala Leu Gln Asn Tyr Ile
            405                 410                 415

Lys Glu Ala Leu Ile Val Ile Asp Lys Ser Tyr Met Asn Pro Gly Asp
                420                 425                 430

Gln Ser Pro Ala Asp Ser Asn Lys Thr Leu Glu Lys Met Glu Lys His
            435                 440                 445

Arg Lys
    450

<210> SEQ ID NO 4
<211> LENGTH: 16
<212> TYPE: PRT
<213> ORGANISM: Homo sapiens

<400> SEQUENCE: 4
```

Pro Gly Arg Gln Ser Gln Glu Gly Ala Gly Leu Pro Ser His His Gly
1               5                   10                  15

<210> SEQ ID NO 5
<211> LENGTH: 580
<212> TYPE: PRT
<213> ORGANISM: Homo sapiens

<400> SEQUENCE: 5

Met Asn Phe Leu Arg Arg Arg Leu Ser Asp Ser Ser Phe Met Ala Asn
1               5                   10                  15

Leu Pro Asn Gly Tyr Met Thr Asp Leu Gln Arg Pro Asp Ser Ser Thr
            20                  25                  30

Ser Ser Pro Ala Ser Pro Ala Met Glu Arg Arg His Pro Gln Pro Leu
        35                  40                  45

Ala Ala Ser Phe Ser Ser Pro Gly Ser Ser Leu Phe Ser Ser Leu Ser
    50                  55                  60

Ser Ala Met Lys Gln Ala Pro Gln Ala Thr Ser Gly Leu Met Glu Pro
65                  70                  75                  80

Pro Gly Pro Ser Thr Pro Ile Val Gln Arg Pro Arg Ile Leu Leu Val
                85                  90                  95

Ile Asp Asp Ala His Thr Asp Trp Ser Lys Tyr Phe His Gly Lys Lys
            100                 105                 110

Val Asn Gly Glu Ile Glu Ile Arg Val Glu Gln Ala Glu Phe Ser Glu
        115                 120                 125

Leu Asn Leu Ala Ala Tyr Val Thr Gly Gly Cys Met Val Asp Met Gln
    130                 135                 140

Val Val Arg Asn Gly Thr Lys Val Val Ser Arg Ser Phe Lys Pro Asp
145                 150                 155                 160

Phe Ile Leu Val Arg Gln His Ala Tyr Ser Met Ala Leu Gly Glu Asp
                165                 170                 175

Tyr Arg Ser Leu Val Ile Gly Leu Gln Tyr Gly Gly Leu Pro Ala Val
            180                 185                 190

Asn Ser Leu Tyr Ser Val Tyr Asn Phe Cys Ser Lys Pro Trp Val Phe
        195                 200                 205

Ser Gln Leu Ile Lys Ile Phe His Ser Leu Gly Pro Glu Lys Phe Pro
    210                 215                 220

Leu Val Glu Gln Thr Phe Phe Pro Asn His Lys Pro Met Val Thr Ala
225                 230                 235                 240

Pro His Phe Pro Val Val Lys Leu Gly His Ala His Ala Gly Met
                245                 250                 255

Gly Lys Ile Lys Val Glu Asn Gln Leu Asp Phe Gln Asp Ile Thr Ser
            260                 265                 270

Val Val Ala Met Ala Lys Thr Tyr Ala Thr Thr Glu Ala Phe Ile Asp
        275                 280                 285

Ser Lys Tyr Asp Ile Arg Ile Gln Lys Ile Gly Ser Asn Tyr Lys Ala
    290                 295                 300

Tyr Met Arg Thr Ser Ile Ser Gly Asn Trp Lys Ala Asn Thr Gly Ser
305                 310                 315                 320

Ala Met Leu Glu Gln Val Ala Met Thr Glu Arg Tyr Arg Leu Trp Val
                325                 330                 335

Asp Ser Cys Ser Glu Met Phe Gly Gly Leu Asp Ile Cys Ala Val Lys
            340                 345                 350

Ala Val His Ser Lys Asp Gly Arg Asp Tyr Ile Ile Glu Val Met Asp

```
            355                 360                 365
Ser Ser Met Pro Leu Ile Gly Glu His Val Glu Glu Asp Arg Gln Leu
370                 375                 380

Met Ala Asp Leu Val Val Ser Lys Met Ser Gln Leu Pro Met Pro Gly
385                 390                 395                 400

Gly Thr Ala Pro Ser Pro Leu Arg Pro Trp Ala Pro Gln Ile Lys Ser
                405                 410                 415

Ala Lys Ser Pro Gly Gln Ala Gln Leu Gly Pro Gln Leu Gly Gln Pro
                420                 425                 430

Gln Pro Arg Pro Pro Gln Gly Gly Pro Arg Gln Ala Gln Ser Pro
                435                 440                 445

Gln Pro Gln Arg Ser Gly Ser Pro Ser Gln Arg Leu Ser Pro Gln
        450                 455                 460

Gly Gln Gln Pro Leu Ser Pro Gln Ser Gly Ser Pro Gln Gln Arg
465                 470                 475                 480

Ser Pro Gly Ser Pro Gln Leu Ser Arg Ala Ser Ser Gly Ser Ser Pro
                485                 490                 495

Asn Gln Ala Ser Lys Pro Gly Ala Thr Leu Ala Ser Gln Pro Arg Pro
                500                 505                 510

Pro Val Gln Gly Arg Ser Thr Ser Gln Gln Gly Glu Ser Lys Lys
        515                 520                 525

Pro Ala Pro Pro His Pro His Leu Asn Lys Ser Gln Ser Leu Thr Asn
                530                 535                 540

Ser Leu Ser Thr Ser Asp Thr Ser Gln Arg Gly Thr Pro Ser Glu Asp
545                 550                 555                 560

Glu Ala Lys Ala Glu Thr Ile Arg Asn Leu Arg Lys Ser Phe Ala Ser
                565                 570                 575

Leu Phe Ser Asp
            580

<210> SEQ ID NO 6
<211> LENGTH: 17
<212> TYPE: PRT
<213> ORGANISM: Homo sapiens

<400> SEQUENCE: 6

Glu Met Phe Gly Gly Leu Asp Ile Cys Ala Val Lys Ala Val His Ser
1               5                   10                  15

Lys

<210> SEQ ID NO 7
<211> LENGTH: 389
<212> TYPE: PRT
<213> ORGANISM: Homo sapiens

<400> SEQUENCE: 7

Met Glu Gly Ala Leu Ala Ala Asn Trp Ser Glu Ala Ala Asn Ala
1               5                   10                  15

Ser Ala Ala Pro Pro Gly Ala Glu Gly Asn Arg Thr Ala Gly Pro Pro
                20                  25                  30

Arg Arg Asn Glu Ala Leu Ala Arg Val Glu Val Ala Val Leu Cys Leu
            35                  40                  45

Ile Leu Leu Leu Ala Leu Ser Gly Asn Ala Cys Val Leu Leu Ala Leu
        50                  55                  60

Arg Thr Thr Arg Gln Lys His Ser Arg Leu Phe Phe Phe Met Lys His
65                  70                  75                  80
```

```
Leu Ser Ile Ala Asp Leu Val Ala Val Phe Gln Val Leu Pro Gln
                85                  90                  95

Leu Leu Trp Asp Ile Thr Phe Arg Phe Tyr Gly Pro Asp Leu Leu Cys
            100                 105                 110

Arg Leu Val Lys Tyr Leu Gln Val Val Gly Met Phe Ala Ser Thr Tyr
            115                 120                 125

Leu Leu Leu Leu Met Ser Leu Asp Arg Cys Leu Ala Ile Cys Gln Pro
        130                 135                 140

Leu Arg Ser Leu Arg Arg Arg Thr Asp Arg Leu Ala Val Leu Ala Thr
145                 150                 155                 160

Trp Leu Gly Cys Leu Val Ala Ser Ala Pro Gln Val His Ile Phe Ser
                165                 170                 175

Leu Arg Glu Val Ala Asp Gly Val Phe Asp Cys Trp Ala Val Phe Ile
            180                 185                 190

Gln Pro Trp Gly Pro Lys Ala Tyr Ile Thr Trp Ile Thr Leu Ala Val
            195                 200                 205

Tyr Ile Val Pro Val Ile Val Leu Ala Ala Cys Tyr Gly Leu Ile Ser
        210                 215                 220

Phe Lys Ile Trp Gln Asn Leu Arg Leu Lys Thr Ala Ala Ala Ala Ala
225                 230                 235                 240

Ala Glu Ala Pro Glu Gly Ala Ala Ala Gly Asp Gly Gly Arg Val Ala
                245                 250                 255

Leu Ala Arg Val Ser Ser Val Lys Leu Ile Ser Lys Ala Lys Ile Arg
            260                 265                 270

Thr Val Lys Met Thr Phe Ile Ile Val Leu Ala Phe Ile Val Cys Trp
            275                 280                 285

Thr Pro Phe Phe Phe Val Gln Met Trp Ser Val Trp Asp Ala Asn Ala
        290                 295                 300

Pro Lys Glu Ala Ser Ala Phe Ile Ile Val Met Leu Leu Ala Ser Leu
305                 310                 315                 320

Asn Ser Cys Cys Asn Pro Trp Ile Tyr Met Leu Phe Thr Gly His Leu
                325                 330                 335

Phe His Glu Leu Val Gln Arg Phe Leu Cys Cys Ser Ala Ser Tyr Leu
            340                 345                 350

Lys Gly Arg Arg Leu Gly Glu Thr Ser Ala Ser Lys Lys Ser Asn Ser
            355                 360                 365

Ser Ser Phe Val Leu Ser His Arg Ser Ser Ser Gln Arg Ser Cys Ser
        370                 375                 380

Gln Pro Ser Thr Ala
385

<210> SEQ ID NO 8
<211> LENGTH: 11
<212> TYPE: PRT
<213> ORGANISM: Homo sapiens

<400> SEQUENCE: 8

Ala Ala Pro Pro Gly Ala Glu Gly Asn Arg Thr
1               5                   10

<210> SEQ ID NO 9
<211> LENGTH: 1290
<212> TYPE: PRT
<213> ORGANISM: Homo sapiens

<400> SEQUENCE: 9
```

```
Gly Pro Pro Val Pro Ala Ser Ser Thr Lys Leu Leu Met Thr Ser
1               5                   10                  15

Tyr Ser Met Arg Ser Thr Val Val Ser Arg Tyr Ala His Thr Leu Val
            20                  25                  30

Thr Ser Val Leu Phe Asn Pro His Ala Glu Ala His Glu Ala Ile Phe
        35                  40                  45

Asp Leu Asp Leu Pro His Leu Ala Phe Ile Ser Asn Phe Thr Met Thr
    50                  55                  60

Ile Asn Asn Lys Val Tyr Ile Ala Glu Val Lys Glu Lys His Gln Ala
65                  70                  75                  80

Lys Lys Ile Tyr Glu Glu Ala His Gln Gln Gly Lys Thr Ala Ala His
                85                  90                  95

Val Gly Ile Arg Asp Arg Glu Ser Glu Lys Phe Arg Ile Ser Thr Ser
            100                 105                 110

Leu Ala Ala Gly Thr Glu Val Thr Phe Ser Leu Ala Tyr Glu Glu Leu
        115                 120                 125

Leu Gln Arg His Gln Gly Gln Tyr Gln Leu Val Val Ser Leu Arg Pro
    130                 135                 140

Gly Gln Leu Val Lys Arg Leu Ser Ile Glu Val Thr Val Ser Glu Arg
145                 150                 155                 160

Thr Gly Ile Ser Tyr Val His Ile Pro Pro Leu Arg Thr Gly Arg Leu
            165                 170                 175

Arg Thr Asn Ala His Ala Ser Glu Val Asp Ser Pro Ser Thr Arg
        180                 185                 190

Ile Glu Arg Gly Glu Thr Cys Val Arg Ile Thr Tyr Cys Pro Thr Leu
            195                 200                 205

Gln Asp Gln Ser Ser Ile Ser Gly Ser Gly Ile Met Ala Asp Phe Leu
    210                 215                 220

Val Gln Tyr Asp Val Val Met Glu Asp Ile Ile Gly Asp Val Gln Ile
225                 230                 235                 240

Tyr Asp Asp Tyr Phe Ile His Tyr Phe Ala Pro Arg Gly Leu Pro Pro
            245                 250                 255

Met Glu Lys Asn Val Val Phe Val Ile Asp Val Ser Ser Ser Met Phe
        260                 265                 270

Gly Thr Lys Met Glu Gln Thr Lys Thr Ala Met Asn Val Ile Leu Ser
    275                 280                 285

Asp Leu Gln Ala Asn Asp Tyr Phe Asn Ile Ile Ser Phe Ser Asp Thr
    290                 295                 300

Val Asn Val Trp Lys Ala Gly Gly Ser Ile Gln Ala Thr Ile Gln Asn
305                 310                 315                 320

Val His Ser Ala Lys Asp Tyr Leu His Cys Met Glu Ala Asp Gly Trp
            325                 330                 335

Thr Asp Val Asn Ser Ala Leu Leu Ala Ala Ser Val Leu Asn His
        340                 345                 350

Ser Asn Gln Glu Pro Gly Arg Gly Pro Ser Val Gly Arg Ile Pro Leu
    355                 360                 365

Ile Ile Phe Leu Thr Asp Gly Pro Thr Ala Gly Val Thr Thr Pro
        370                 375                 380

Ser Val Ile Leu Ser Asn Val Arg Gln Ala Leu Gly His Arg Val Ser
385                 390                 395                 400

Leu Phe Ser Leu Ala Phe Gly Asp Asp Ala Asp Phe Thr Leu Leu Arg
            405                 410                 415

Arg Leu Ser Leu Glu Asn Arg Gly Ile Ala Arg Arg Ile Tyr Glu Asp
        420                 425                 430

Thr Asp Ala Ala Leu Gln Leu Lys Gly Leu Tyr Glu Glu Ile Ser Met
        435                 440                 445
```

```
Pro Leu Leu Ala Asp Val Arg Leu Asn Tyr Leu Gly Gly Leu Val Gly
450                 455                 460

Ala Ser Pro Trp Ala Val Phe Pro Asn Tyr Phe Gly Gly Ser Glu Leu
465                 470                 475                 480

Val Val Ala Gly Gln Val Gln Pro Gly Lys Gln Glu Leu Gly Ile His
            485                 490                 495

Leu Ala Ala Arg Gly Pro Lys Asp Gln Leu Leu Val Ala His His Ser
            500                 505                 510

Glu Gly Ala Thr Asn Asn Ser Gln Lys Ala Phe Gly Cys Pro Gly Glu
            515                 520                 525

Pro Ala Pro Asn Val Ala His Phe Ile Arg Arg Leu Trp Ala Tyr Val
530                 535                 540

Thr Ile Gly Glu Leu Leu Asp Ala His Phe Gln Ala Arg Asp Thr Thr
545                 550                 555                 560

Thr Arg His Leu Leu Ala Ala Lys Val Leu Asn Leu Ser Leu Glu Tyr
            565                 570                 575

Asn Phe Val Thr Pro Leu Thr Ser Leu Val Met Val Gln Pro Lys Gln
            580                 585                 590

Ala Ser Glu Glu Thr Arg Arg Gln Thr Ser Thr Ser Ala Gly Pro Asp
            595                 600                 605

Thr Ile Met Pro Ser Ser Ser Arg His Gly Leu Gly Val Ser Thr
610                 615                 620

Ala Gln Pro Ala Leu Val Pro Lys Val Ile Ser Pro Lys Ser Arg Pro
625                 630                 635                 640

Val Lys Pro Lys Phe Tyr Leu Ser Ser Thr Thr Ala Ser Thr Lys
            645                 650                 655

Lys Met Leu Ser Ser Lys Glu Leu Glu Pro Leu Gly Glu Ser Pro His
            660                 665                 670

Thr Leu Ser Met Pro Thr Tyr Pro Lys Ala Lys Ile Pro Ala Gln Gln
            675                 680                 685

Asp Ser Gly Thr Leu Ala Gln Pro Thr Leu Arg Thr Lys Pro Thr Ile
690                 695                 700

Leu Val Pro Ser Asn Ser Gly Thr Leu Leu Pro Leu Lys Pro Gly Ser
705                 710                 715                 720

Leu Ser His Gln Asn Pro Asp Ile Leu Pro Thr Asn Ser Arg Thr Gln
            725                 730                 735

Val Pro Pro Val Lys Pro Gly Ile Pro Ala Ser Pro Lys Ala Asp Thr
            740                 745                 750

Val Lys Cys Val Thr Pro Leu His Ser Lys Pro Gly Ala Pro Ser His
            755                 760                 765

Pro Gln Leu Gly Ala Leu Thr Ser Gln Ala Pro Lys Gly Leu Pro Gln
770                 775                 780

Ser Arg Pro Gly Val Ser Thr Leu Gln Val Pro Lys Tyr Pro Leu His
785                 790                 795                 800

Thr Arg Pro Arg Val Pro Ala Pro Lys Thr Arg Asn Asn Met Pro His
            805                 810                 815

Leu Gly Pro Gly Ile Leu Leu Ser Lys Thr Pro Lys Ile Leu Leu Ser
            820                 825                 830

Leu Lys Pro Ser Ala Pro Pro His Gln Ile Ser Thr Ser Ile Ser Leu
            835                 840                 845

Ser Lys Pro Glu Thr Pro Asn Pro His Met Pro Gln Thr Pro Leu Pro
850                 855                 860

Pro Arg Pro Asp Arg Pro Arg Pro Pro Leu Pro Glu Ser Leu Ser Thr
```

```
            865                 870                 875                 880
     Phe Pro Asn Thr Ile Ser Ser Thr Gly Pro Ser Ser Thr Thr Thr
                     885                 890                 895

Thr Ser Val Leu Gly Glu Pro Leu Pro Met Pro Phe Thr Pro Thr Leu
                     900                 905                 910

Pro Pro Gly Arg Phe Trp His Gln Tyr Asp Leu Leu Pro Gly Pro Gln
                     915                 920                 925

Arg Thr Arg Gln Val Leu Gly Pro Ser Arg Pro Gly Val Pro Thr Met
                 930                 935                 940

Ser Leu Leu Asn Ser Ser Arg Pro Thr Pro Glu Gly Ser Pro Asn
     945                 950                 955                 960

Leu Pro Ile Leu Leu Pro Ser Ser Ile Leu Pro Glu Ala Ile Ser Leu
                     965                 970                 975

Leu Leu Leu Pro Glu Glu Leu Glu Leu Leu Ser Glu Ser Met Val Glu
                     980                 985                 990

Ser Lys Phe Val Glu Ser Leu Asn Pro Pro Ala Phe Tyr Thr Phe Leu
                 995                1000                1005

Thr Pro Asp Glu Asp Gly Ser Pro Asn Trp Asp Gly Asn Ser Glu
     1010                1015                1020

Glu Ile Leu Gly Gly Ala Gly Gly Ser Met Glu Ser Gln Gly Ser
     1025                1030                1035

Ser Val Gly Leu Ala Lys Gly Thr Leu Pro Ser Ile Phe Thr Phe
     1040                1045                1050

Ser Ser Ser Val Asp Gly Asp Pro His Phe Val Ile Gln Ile Pro
     1055                1060                1065

His Ser Glu Glu Lys Ile Cys Phe Thr Leu Asn Gly His Pro Gly
     1070                1075                1080

Asp Leu Leu Gln Leu Ile Glu Asp Pro Lys Ala Gly Leu His Val
     1085                1090                1095

Ser Gly Lys Leu Leu Gly Ala Pro Pro Arg Pro Gly His Lys Asp
     1100                1105                1110

Gln Thr Arg Thr Tyr Phe Gln Ile Ile Thr Val Thr Thr Asp Lys
     1115                1120                1125

Pro Arg Ala Tyr Thr Ile Thr Ile Ser Arg Ser Ser Ile Ser Leu
     1130                1135                1140

Arg Gly Glu Gly Thr Leu Arg Leu Ser Trp Asp Gln Pro Ala Leu
     1145                1150                1155

Leu Lys Arg Pro Gln Leu Glu Leu Tyr Val Ala Ala Ala Ala Arg
     1160                1165                1170

Leu Thr Leu Arg Leu Gly Pro Tyr Leu Glu Phe Leu Val Leu Arg
     1175                1180                1185

His Arg Tyr Arg His Pro Ser Thr Leu Gln Leu Pro His Leu Gly
     1190                1195                1200

Phe Tyr Val Ala Asn Gly Ser Gly Leu Ser Pro Ala Arg Gly
     1205                1210                1215

Leu Ile Gly Gln Phe Gln His Ala Asp Ile Arg Leu Val Thr Gly
     1220                1225                1230

Pro Met Gly Pro Cys Leu Arg Arg His His Gly Pro Asp Val Pro
     1235                1240                1245

Val Ile Leu Gly Lys Arg Leu Leu Lys Asp Ser Pro Arg Leu Leu
     1250                1255                1260

Pro Arg Trp Ala Ser Cys Trp Leu Val Lys Arg Ser His Val Glu
     1265                1270                1275
```

Leu Leu Leu Gly His Pro Tyr Leu Ser Tyr Val Leu
    1280            1285            1290

<210> SEQ ID NO 10
<211> LENGTH: 14
<212> TYPE: PRT
<213> ORGANISM: Homo sapiens

<400> SEQUENCE: 10

Arg Val Ser Leu Phe Ser Leu Ala Phe Gly Asp Asp Ala Asp
1               5                   10

<210> SEQ ID NO 11
<211> LENGTH: 4834
<212> TYPE: PRT
<213> ORGANISM: Homo sapiens

<400> SEQUENCE: 11

Met Pro Ser Glu Ser Phe Cys Leu Ala Ala Gln Ala Arg Leu Asp Ser
1               5                   10                  15

Lys Trp Leu Lys Thr Asp Ile Gln Leu Ala Phe Thr Arg Asp Gly Leu
            20                  25                  30

Cys Gly Leu Trp Asn Glu Met Val Lys Asp Gly Ile Val Tyr Thr
        35                  40                  45

Gly Thr Glu Ser Thr Gln Asn Gly Glu Leu Pro Pro Arg Lys Asp Asp
    50                  55                  60

Ser Val Glu Pro Ser Gly Thr Lys Lys Glu Asp Leu Asn Asp Lys Glu
65                  70                  75                  80

Lys Lys Asp Glu Glu Glu Thr Pro Ala Pro Ile Tyr Arg Ala Lys Ser
                85                  90                  95

Ile Leu Asp Ser Trp Val Trp Gly Lys Gln Pro Asp Val Asn Glu Leu
            100                 105                 110

Lys Glu Cys Leu Ser Val Leu Val Lys Glu Gln Gln Ala Leu Ala Val
        115                 120                 125

Gln Ser Ala Thr Thr Thr Leu Ser Ala Leu Arg Leu Lys Gln Arg Leu
    130                 135                 140

Val Ile Leu Glu Arg Tyr Phe Ile Ala Leu Asn Arg Thr Val Phe Gln
145                 150                 155                 160

Glu Asn Val Lys Val Lys Trp Lys Ser Ser Gly Ile Ser Leu Pro Pro
                165                 170                 175

Val Asp Lys Lys Ser Ser Arg Pro Ala Gly Lys Gly Val Glu Gly Leu
            180                 185                 190

Ala Arg Val Gly Ser Arg Ala Ala Leu Ser Phe Ala Phe Ala Phe Leu
        195                 200                 205

Arg Arg Ala Trp Arg Ser Gly Glu Asp Ala Asp Leu Cys Ser Glu Leu
    210                 215                 220

Leu Gln Glu Ser Leu Asp Ala Leu Arg Ala Leu Pro Glu Ala Ser Leu
225                 230                 235                 240

Phe Asp Glu Ser Thr Val Ser Val Trp Leu Glu Val Val Glu Arg
                245                 250                 255

Ala Thr Arg Phe Leu Arg Ser Val Thr Gly Asp Val His Gly Thr
            260                 265                 270

Pro Ala Thr Lys Gly Pro Gly Ser Ile Pro Leu Gln Asp Gln His Leu
        275                 280                 285

Ala Leu Ala Ile Leu Leu Glu Leu Ala Val Gln Arg Gly Thr Leu Ser
    290                 295                 300

```
Gln Met Leu Ser Ala Ile Leu Leu Leu Gln Leu Trp Asp Ser Gly
305                 310                 315                 320

Ala Gln Glu Thr Asp Asn Glu Arg Ser Ala Gln Gly Thr Ser Ala Pro
            325                 330                 335

Leu Leu Pro Leu Leu Gln Arg Phe Gln Ser Ile Ile Cys Arg Lys Asp
            340                 345                 350

Ala Pro His Ser Glu Gly Asp Met His Leu Leu Ser Gly Pro Leu Ser
            355                 360                 365

Pro Asn Glu Ser Phe Leu Arg Tyr Leu Thr Leu Pro Gln Asp Asn Glu
    370                 375                 380

Leu Ala Ile Asp Leu Arg Gln Thr Ala Val Val Met Ala His Leu
385                 390                 395                 400

Asp Arg Leu Ala Thr Pro Cys Met Pro Pro Leu Cys Ser Ser Pro Thr
                405                 410                 415

Ser His Lys Gly Ser Leu Gln Glu Val Ile Gly Trp Gly Leu Ile Gly
                420                 425                 430

Trp Lys Tyr Tyr Ala Asn Val Ile Gly Pro Ile Gln Cys Glu Gly Leu
            435                 440                 445

Ala Asn Leu Gly Val Thr Gln Ile Ala Cys Ala Glu Lys Arg Phe Leu
450                 455                 460

Ile Leu Ser Arg Asn Gly Arg Val Tyr Thr Gln Ala Tyr Asn Ser Asp
465                 470                 475                 480

Thr Leu Ala Pro Gln Leu Val Gln Gly Leu Ala Ser Arg Asn Ile Val
            485                 490                 495

Lys Ile Ala Ala His Ser Asp Gly His His Tyr Leu Ala Leu Ala Ala
                500                 505                 510

Thr Gly Glu Val Tyr Ser Trp Gly Cys Gly Asp Gly Gly Arg Leu Gly
            515                 520                 525

His Gly Asp Thr Val Pro Leu Glu Glu Pro Lys Val Ile Ser Ala Phe
    530                 535                 540

Ser Gly Lys Gln Ala Gly Lys His Val Val His Ile Ala Cys Gly Ser
545                 550                 555                 560

Thr Tyr Ser Ala Ala Ile Thr Ala Glu Gly Glu Leu Tyr Thr Trp Gly
                565                 570                 575

Arg Gly Asn Tyr Gly Arg Leu Gly His Gly Ser Ser Glu Asp Glu Ala
            580                 585                 590

Ile Pro Met Leu Val Ala Gly Leu Lys Gly Leu Lys Val Ile Asp Val
    595                 600                 605

Ala Cys Gly Ser Gly Asp Ala Gln Thr Leu Ala Val Thr Glu Asn Gly
    610                 615                 620

Gln Val Trp Ser Trp Gly Asp Gly Asp Tyr Gly Lys Leu Gly Arg Gly
625                 630                 635                 640

Gly Ser Asp Gly Cys Lys Thr Pro Lys Leu Ile Glu Lys Leu Gln Asp
                645                 650                 655

Leu Asp Val Val Lys Val Arg Cys Gly Ser Gln Phe Ser Ile Ala Leu
            660                 665                 670

Thr Lys Asp Gly Gln Val Tyr Ser Trp Gly Lys Gly Asp Asn Gln Arg
            675                 680                 685

Leu Gly His Gly Thr Glu Glu His Val Arg Tyr Pro Lys Leu Leu Glu
    690                 695                 700

Gly Leu Gln Gly Lys Lys Val Ile Asp Val Ala Ala Gly Ser Thr His
705                 710                 715                 720
```

-continued

```
Cys Leu Ala Leu Thr Glu Asp Ser Glu Val His Ser Trp Gly Ser Asn
                725                 730                 735

Asp Gln Cys Gln His Phe Asp Thr Leu Arg Val Thr Lys Pro Glu Pro
            740                 745                 750

Ala Ala Leu Pro Gly Leu Asp Thr Lys His Ile Val Gly Ile Ala Cys
        755                 760                 765

Gly Pro Ala Gln Ser Phe Ala Trp Ser Cys Ser Glu Trp Ser Ile
    770                 775                 780

Gly Leu Arg Val Pro Phe Val Val Asp Ile Cys Ser Met Thr Phe Glu
785                 790                 795                 800

Gln Leu Asp Leu Leu Arg Gln Val Ser Glu Gly Met Asp Gly Ser
                805                 810                 815

Ala Asp Trp Pro Pro Gln Glu Lys Glu Cys Val Ala Val Ala Thr
            820                 825                 830

Leu Asn Leu Leu Arg Leu Gln Leu His Ala Ala Ile Ser His Gln Val
                835                 840                 845

Asp Pro Glu Phe Leu Gly Leu Gly Leu Gly Ser Ile Leu Leu Asn Ser
    850                 855                 860

Leu Lys Gln Thr Val Val Thr Leu Ala Ser Ser Ala Gly Val Leu Ser
865                 870                 875                 880

Thr Val Gln Ser Ala Ala Gln Ala Val Leu Gln Ser Gly Trp Ser Val
                885                 890                 895

Leu Leu Pro Thr Ala Glu Glu Arg Ala Arg Ala Leu Ser Ala Leu Leu
            900                 905                 910

Pro Cys Ala Val Ser Gly Asn Glu Val Asn Ile Ser Pro Gly Arg Arg
        915                 920                 925

Phe Met Ile Asp Leu Leu Val Gly Ser Leu Met Ala Asp Gly Gly Leu
    930                 935                 940

Glu Ser Ala Leu His Ala Ala Ile Thr Ala Glu Ile Gln Asp Ile Glu
945                 950                 955                 960

Ala Lys Lys Glu Ala Gln Lys Glu Lys Glu Ile Asp Glu Gln Glu Ala
                965                 970                 975

Asn Ala Ser Thr Phe His Arg Ser Arg Thr Pro Leu Asp Lys Asp Leu
            980                 985                 990

Ile Asn Thr Gly Ile Cys Glu Ser  Ser Gly Lys Gln Cys  Leu Pro Leu
        995                 1000                1005

Val Gln  Leu Ile Gln Gln Leu  Leu Arg Asn Ile Ala  Ser Gln Thr
    1010                1015                1020

Val Ala  Arg Leu Lys Asp Val  Ala Arg Arg Ile Ser  Ser Cys Leu
    1025                1030                1035

Asp Phe  Glu Gln His Ser Arg  Glu Arg Ser Ala Ser  Leu Asp Leu
    1040                1045                1050

Leu Leu  Arg Phe Gln Arg Leu  Leu Ile Ser Lys Leu  Tyr Pro Gly
    1055                1060                1065

Glu Ser  Ile Gly Gln Thr Ser  Asp Ile Ser Ser Pro  Glu Leu Met
    1070                1075                1080

Gly Val  Gly Ser Leu Leu Lys  Lys Tyr Thr Ala Leu  Leu Cys Thr
    1085                1090                1095

His Ile  Gly Asp Ile Leu Pro  Val Ala Ala Ser Ile  Ala Ser Thr
    1100                1105                1110

Ser Trp  Arg His Phe Ala Glu  Val Ala Tyr Ile Val  Glu Gly Asp
    1115                1120                1125

Phe Thr  Gly Val Leu Leu Pro  Glu Leu Val Val Ser  Ile Val Leu
```

-continued

```
            1130                1135                1140
Leu Leu Ser Lys Asn Ala Gly Leu Met Gln Glu Ala Gly Ala Val
    1145                1150                1155
Pro Leu Leu Gly Gly Leu Leu Glu His Leu Asp Arg Phe Asn His
    1160                1165                1170
Leu Ala Pro Gly Lys Glu Arg Asp Asp His Glu Glu Leu Ala Trp
    1175                1180                1185
Pro Gly Ile Met Glu Ser Phe Phe Thr Gly Gln Asn Cys Arg Asn
    1190                1195                1200
Asn Glu Glu Val Thr Leu Ile Arg Lys Ala Asp Leu Glu Asn His
    1205                1210                1215
Asn Lys Asp Gly Gly Phe Trp Thr Val Ile Asp Gly Lys Val Tyr
    1220                1225                1230
Asp Ile Lys Asp Phe Gln Thr Gln Ser Leu Thr Gly Asn Ser Ile
    1235                1240                1245
Leu Ala Gln Phe Ala Gly Glu Asp Pro Val Val Ala Leu Glu Ala
    1250                1255                1260
Ala Leu Gln Phe Glu Asp Thr Arg Glu Ser Met His Ala Phe Cys
    1265                1270                1275
Val Gly Gln Tyr Leu Glu Pro Asp Gln Glu Ile Val Thr Ile Pro
    1280                1285                1290
Asp Leu Gly Ser Leu Ser Ser Pro Leu Ile Asp Thr Glu Arg Asn
    1295                1300                1305
Leu Gly Leu Leu Leu Gly Leu His Ala Ser Tyr Leu Ala Met Ser
    1310                1315                1320
Thr Pro Leu Ser Pro Val Glu Ile Glu Cys Ala Lys Trp Leu Gln
    1325                1330                1335
Ser Ser Ile Phe Ser Gly Gly Leu Gln Thr Ser Gln Ile His Tyr
    1340                1345                1350
Ser Tyr Asn Glu Glu Lys Asp Glu Asp His Cys Ser Ser Pro Gly
    1355                1360                1365
Gly Thr Pro Ala Ser Lys Ser Arg Leu Cys Ser His Arg Arg Ala
    1370                1375                1380
Leu Gly Asp His Ser Gln Ala Phe Leu Gln Ala Ile Ala Asp Asn
    1385                1390                1395
Asn Ile Gln Asp His Asn Val Lys Asp Phe Leu Cys Gln Ile Glu
    1400                1405                1410
Arg Tyr Cys Arg Gln Cys His Leu Thr Thr Pro Ile Met Phe Pro
    1415                1420                1425
Pro Glu His Pro Val Glu Glu Val Gly Arg Leu Leu Leu Cys Cys
    1430                1435                1440
Leu Leu Lys His Glu Asp Leu Gly His Val Ala Leu Ser Leu Val
    1445                1450                1455
His Ala Gly Ala Leu Gly Ile Glu Gln Val Lys His Arg Thr Leu
    1460                1465                1470
Pro Lys Ser Val Val Asp Val Cys Arg Val Val Tyr Gln Ala Lys
    1475                1480                1485
Cys Ser Leu Ile Lys Thr His Gln Glu Gln Gly Arg Ser Tyr Lys
    1490                1495                1500
Glu Val Cys Ala Pro Val Ile Glu Arg Leu Arg Phe Leu Phe Asn
    1505                1510                1515
Glu Leu Arg Pro Ala Val Cys Asn Asp Leu Ser Ile Met Ser Lys
    1520                1525                1530
```

```
Phe Lys Leu Leu Ser Ser Leu Pro Arg Trp Arg Ile Ala Gln
1535             1540                1545

Lys Ile Ile Arg Glu Arg Arg Lys Lys Arg Val Pro Lys Lys Pro
1550             1555                1560

Glu Ser Thr Asp Asp Glu Glu Lys Ile Gly Asn Glu Glu Ser Asp
1565             1570                1575

Leu Glu Glu Ala Cys Ile Leu Pro His Ser Pro Ile Asn Val Asp
1580             1585                1590

Lys Arg Pro Ile Ala Ile Lys Ser Pro Lys Asp Lys Trp Gln Pro
1595             1600                1605

Leu Leu Ser Thr Val Thr Gly Val His Lys Tyr Lys Trp Leu Lys
1610             1615                1620

Gln Asn Val Gln Gly Leu Tyr Pro Gln Ser Pro Leu Leu Ser Thr
1625             1630                1635

Ile Ala Glu Phe Ala Leu Lys Glu Glu Pro Val Asp Val Glu Lys
1640             1645                1650

Met Arg Lys Cys Leu Leu Lys Gln Leu Glu Arg Ala Glu Val Arg
1655             1660                1665

Leu Glu Gly Ile Asp Thr Ile Leu Lys Leu Ala Ser Lys Asn Phe
1670             1675                1680

Leu Leu Pro Ser Val Gln Tyr Ala Met Phe Cys Gly Trp Gln Arg
1685             1690                1695

Leu Ile Pro Glu Gly Ile Asp Ile Gly Glu Pro Leu Thr Asp Cys
1700             1705                1710

Leu Lys Asp Val Asp Leu Ile Pro Pro Phe Asn Arg Met Leu Leu
1715             1720                1725

Glu Val Thr Phe Gly Lys Leu Tyr Ala Trp Ala Val Gln Asn Ile
1730             1735                1740

Arg Asn Val Leu Met Asp Ala Ser Ala Lys Phe Lys Glu Leu Gly
1745             1750                1755

Ile Gln Pro Val Pro Leu Gln Thr Ile Thr Asn Glu Asn Pro Ser
1760             1765                1770

Gly Pro Ser Leu Gly Thr Ile Pro Gln Ala Arg Phe Leu Leu Val
1775             1780                1785

Met Leu Ser Met Leu Thr Leu Gln His Gly Ala Asn Asn Leu Asp
1790             1795                1800

Leu Leu Leu Asn Ser Gly Met Leu Ala Leu Thr Gln Thr Ala Leu
1805             1810                1815

Arg Leu Ile Gly Pro Ser Cys Asp Asn Val Glu Glu Asp Met Asn
1820             1825                1830

Ala Ser Ala Gln Gly Ala Ser Ala Thr Val Leu Glu Glu Thr Arg
1835             1840                1845

Lys Glu Thr Ala Pro Val Gln Leu Pro Val Ser Gly Pro Glu Leu
1850             1855                1860

Ala Ala Met Met Lys Ile Gly Thr Arg Val Met Arg Gly Val Asp
1865             1870                1875

Trp Lys Trp Gly Asp Gln Asp Gly Pro Pro Pro Gly Leu Gly Arg
1880             1885                1890

Val Ile Gly Glu Leu Gly Glu Asp Gly Trp Ile Arg Val Gln Trp
1895             1900                1905

Asp Thr Gly Ser Thr Asn Ser Tyr Arg Met Gly Lys Glu Gly Lys
1910             1915                1920
```

-continued

```
Tyr Asp Leu Lys Leu Ala Glu Leu Pro Ala Ala Ala Gln Pro Ser
    1925            1930                1935

Ala Glu Asp Ser Asp Thr Glu Asp Asp Ser Glu Ala Glu Gln Thr
    1940            1945                1950

Glu Arg Asn Ile His Pro Thr Ala Met Met Phe Thr Ser Thr Ile
    1955            1960                1965

Asn Leu Leu Gln Thr Leu Cys Leu Ser Ala Gly Val His Ala Glu
    1970            1975                1980

Ile Met Gln Ser Glu Ala Thr Lys Thr Leu Cys Gly Leu Leu Arg
    1985            1990                1995

Met Leu Val Glu Ser Gly Thr Thr Asp Lys Thr Ser Ser Pro Asn
    2000            2005                2010

Arg Leu Val Tyr Arg Glu Gln His Arg Ser Trp Cys Thr Leu Gly
    2015            2020                2025

Phe Val Arg Ser Ile Ala Leu Thr Pro Gln Val Cys Gly Ala Leu
    2030            2035                2040

Ser Ser Pro Gln Trp Ile Thr Leu Leu Met Lys Val Val Glu Gly
    2045            2050                2055

His Ala Pro Phe Thr Ala Thr Ser Leu Gln Arg Gln Ile Leu Ala
    2060            2065                2070

Val His Leu Leu Gln Ala Val Leu Pro Ser Trp Asp Lys Thr Glu
    2075            2080                2085

Arg Ala Arg Asp Met Lys Cys Leu Val Glu Lys Leu Phe Asp Phe
    2090            2095                2100

Leu Gly Ser Leu Leu Thr Thr Cys Ser Ser Asp Val Pro Leu Leu
    2105            2110                2115

Arg Glu Ser Thr Leu Arg Arg Arg Val Arg Pro Gln Ala Ser
    2120            2125                2130

Leu Thr Ala Thr His Ser Ser Thr Leu Ala Glu Glu Val Val Ala
    2135            2140                2145

Leu Leu Arg Thr Leu His Ser Leu Thr Gln Trp Asn Gly Leu Ile
    2150            2155                2160

Asn Lys Tyr Ile Asn Ser Gln Leu Arg Ser Ile Thr His Ser Phe
    2165            2170                2175

Val Gly Arg Pro Ser Glu Gly Ala Gln Leu Glu Asp Tyr Phe Pro
    2180            2185                2190

Asp Ser Glu Asn Pro Glu Val Gly Gly Leu Met Ala Val Leu Ala
    2195            2200                2205

Val Ile Gly Gly Ile Asp Gly Arg Leu Arg Leu Gly Gly Gln Val
    2210            2215                2220

Met His Asp Glu Phe Gly Glu Gly Thr Val Thr Arg Ile Thr Pro
    2225            2230                2235

Lys Gly Lys Ile Thr Val Gln Phe Ser Asp Met Arg Thr Cys Arg
    2240            2245                2250

Val Cys Pro Leu Asn Gln Leu Lys Pro Leu Pro Ala Val Ala Phe
    2255            2260                2265

Asn Val Asn Asn Leu Pro Phe Thr Glu Pro Met Leu Ser Val Trp
    2270            2275                2280

Ala Gln Leu Val Asn Leu Ala Gly Ser Lys Leu Glu Lys His Lys
    2285            2290                2295

Ile Lys Lys Ser Thr Lys Gln Ala Phe Ala Gly Gln Val Asp Leu
    2300            2305                2310

Asp Leu Leu Arg Cys Gln Gln Leu Lys Leu Tyr Ile Leu Lys Ala
```

```
                2315                2320                 2325
Gly Arg Ala Leu Leu Ser His Gln Asp Lys Leu Arg Gln Ile Leu
            2330                2335                2340

Ser Gln Pro Ala Val Gln Glu Thr Gly Thr Val His Thr Asp Asp
            2345                2350                2355

Gly Ala Val Val Ser Pro Asp Leu Gly Asp Met Ser Pro Glu Gly
            2360                2365                2370

Pro Gln Pro Pro Met Ile Leu Leu Gln Gln Leu Leu Ala Ser Ala
            2375                2380                2385

Thr Gln Pro Ser Pro Val Lys Ala Ile Phe Asp Lys Gln Glu Leu
            2390                2395                2400

Glu Ala Ala Ala Leu Ala Val Cys Gln Cys Leu Ala Val Glu Ser
            2405                2410                2415

Thr His Pro Ser Ser Pro Gly Phe Glu Asp Cys Ser Ser Ser Glu
            2420                2425                2430

Ala Thr Thr Pro Val Ala Val Gln His Ile Arg Pro Ala Arg Val
            2435                2440                2445

Lys Arg Arg Lys Gln Ser Pro Val Pro Ala Leu Pro Ile Val Val
            2450                2455                2460

Gln Leu Met Glu Met Gly Phe Ser Arg Arg Asn Ile Glu Phe Ala
            2465                2470                2475

Leu Lys Ser Leu Thr Gly Ala Ser Gly Asn Ala Ser Ser Leu Pro
            2480                2485                2490

Gly Val Glu Ala Leu Val Gly Trp Leu Leu Asp His Ser Asp Ile
            2495                2500                2505

Gln Val Thr Glu Leu Ser Asp Ala Asp Thr Val Ser Asp Glu Tyr
            2510                2515                2520

Ser Asp Glu Glu Val Val Glu Asp Val Asp Ala Ala Tyr Ser
            2525                2530                2535

Met Ser Thr Gly Ala Val Val Thr Glu Ser Gln Thr Tyr Lys Lys
            2540                2545                2550

Arg Ala Asp Phe Leu Ser Asn Asp Asp Tyr Ala Val Tyr Val Arg
            2555                2560                2565

Glu Asn Ile Gln Val Gly Met Met Val Arg Cys Cys Arg Ala Tyr
            2570                2575                2580

Glu Glu Val Cys Glu Gly Asp Val Gly Lys Val Ile Lys Leu Asp
            2585                2590                2595

Arg Asp Gly Leu His Asp Leu Asn Val Gln Cys Asp Trp Gln Gln
            2600                2605                2610

Lys Gly Gly Thr Tyr Trp Val Arg Tyr Ile His Val Glu Leu Ile
            2615                2620                2625

Gly Tyr Pro Pro Ser Ser Ser Ser His Ile Lys Ile Gly Asp
            2630                2635                2640

Lys Val Arg Val Lys Ala Ser Val Thr Thr Pro Lys Tyr Lys Trp
            2645                2650                2655

Gly Ser Val Thr His Gln Ser Val Gly Val Val Lys Ala Phe Ser
            2660                2665                2670

Ala Asn Gly Lys Asp Ile Ile Val Asp Phe Pro Gln Gln Ser His
            2675                2680                2685

Trp Thr Gly Leu Leu Ser Glu Met Glu Leu Val Pro Ser Ile His
            2690                2695                2700

Pro Gly Val Thr Cys Asp Gly Cys Gln Met Phe Pro Ile Asn Gly
            2705                2710                2715
```

```
Ser Arg Phe Lys Cys Arg Asn Cys Asp Asp Phe Asp Phe Cys Glu
2720                2725                2730

Thr Cys Phe Lys Thr Lys Lys His Asn Thr Arg His Thr Phe Gly
2735                2740                2745

Arg Ile Asn Glu Pro Gly Gln Ser Ala Val Phe Cys Gly Arg Ser
2750                2755                2760

Gly Lys Gln Leu Lys Arg Cys His Ser Ser Gln Pro Gly Met Leu
2765                2770                2775

Leu Asp Ser Trp Ser Arg Met Val Lys Ser Leu Asn Val Ser Ser
2780                2785                2790

Ser Val Asn Gln Ala Ser Arg Leu Ile Asp Gly Ser Glu Pro Cys
2795                2800                2805

Trp Gln Ser Ser Gly Ser Gln Gly Lys His Trp Ile Arg Leu Glu
2810                2815                2820

Ile Phe Pro Asp Val Leu Val His Arg Leu Lys Met Ile Val Asp
2825                2830                2835

Pro Ala Asp Ser Ser Tyr Met Pro Ser Leu Val Val Val Ser Gly
2840                2845                2850

Gly Asn Ser Leu Asn Asn Leu Ile Glu Leu Lys Thr Ile Asn Ile
2855                2860                2865

Asn Pro Ser Asp Thr Thr Val Pro Leu Leu Asn Asp Cys Thr Glu
2870                2875                2880

Tyr His Arg Tyr Ile Glu Ile Ala Ile Lys Gln Cys Arg Ser Ser
2885                2890                2895

Gly Ile Asp Cys Lys Ile His Gly Leu Ile Leu Leu Gly Arg Ile
2900                2905                2910

Arg Ala Glu Glu Glu Asp Leu Ala Ala Val Pro Phe Leu Ala Ser
2915                2920                2925

Asp Asn Glu Glu Glu Glu Asp Glu Lys Gly Asn Ser Gly Ser Leu
2930                2935                2940

Ile Arg Lys Lys Ala Ala Gly Leu Glu Ser Ala Ala Thr Ile Arg
2945                2950                2955

Thr Lys Val Phe Val Trp Gly Leu Asn Asp Lys Asp Gln Leu Gly
2960                2965                2970

Gly Leu Lys Gly Ser Lys Ile Lys Val Pro Ser Phe Ser Glu Thr
2975                2980                2985

Leu Ser Ala Leu Asn Val Val Gln Val Ala Gly Gly Ser Lys Ser
2990                2995                3000

Leu Phe Ala Val Thr Val Glu Gly Lys Val Tyr Ala Cys Gly Glu
3005                3010                3015

Ala Thr Asn Gly Arg Leu Gly Leu Gly Ile Ser Ser Gly Thr Val
3020                3025                3030

Pro Ile Pro Arg Gln Ile Thr Ala Leu Ser Ser Tyr Val Val Lys
3035                3040                3045

Lys Val Ala Val His Ser Gly Gly Arg His Ala Thr Ala Leu Thr
3050                3055                3060

Val Asp Gly Lys Val Phe Ser Trp Gly Glu Gly Asp Asp Gly Lys
3065                3070                3075

Leu Gly His Phe Ser Arg Met Asn Cys Asp Lys Pro Arg Leu Ile
3080                3085                3090

Glu Ala Leu Lys Thr Lys Arg Ile Arg Asp Ile Ala Cys Gly Ser
3095                3100                3105
```

```
Ser His Ser Ala Ala Leu Thr Ser Ser Gly Glu Leu Tyr Thr Trp
3110                3115                3120

Gly Leu Gly Glu Tyr Gly Arg Leu Gly His Gly Asp Asn Thr Thr
3125                3130                3135

Gln Leu Lys Pro Lys Met Val Lys Val Leu Leu Gly His Arg Val
3140                3145                3150

Ile Gln Val Ala Cys Gly Ser Arg Asp Ala Gln Thr Leu Ala Leu
3155                3160                3165

Thr Asp Glu Gly Leu Val Phe Ser Trp Gly Asp Gly Asp Phe Gly
3170                3175                3180

Lys Leu Gly Arg Gly Gly Ser Glu Gly Cys Asn Ile Pro Gln Asn
3185                3190                3195

Ile Glu Arg Leu Asn Gly Gln Gly Val Cys Gln Ile Glu Cys Gly
3200                3205                3210

Ala Gln Phe Ser Leu Ala Leu Thr Lys Ser Gly Val Val Trp Thr
3215                3220                3225

Trp Gly Lys Gly Asp Tyr Phe Arg Leu Gly His Gly Ser Asp Val
3230                3235                3240

His Val Arg Lys Pro Gln Val Val Glu Gly Leu Arg Gly Lys Lys
3245                3250                3255

Ile Val His Val Ala Val Gly Ala Leu His Cys Leu Ala Val Thr
3260                3265                3270

Asp Ser Gly Gln Val Tyr Ala Trp Gly Asp Asn Asp His Gly Gln
3275                3280                3285

Gln Gly Asn Gly Thr Thr Thr Val Asn Arg Lys Pro Thr Leu Val
3290                3295                3300

Gln Gly Leu Glu Gly Gln Lys Ile Thr Arg Val Ala Cys Gly Ser
3305                3310                3315

Ser His Ser Val Ala Trp Thr Thr Val Asp Val Ala Thr Pro Ser
3320                3325                3330

Val His Glu Pro Val Leu Phe Gln Thr Ala Arg Asp Pro Leu Gly
3335                3340                3345

Ala Ser Tyr Leu Gly Val Pro Ser Asp Ala Asp Ser Ser Ala Ala
3350                3355                3360

Ser Asn Lys Ile Ser Gly Ala Ser Asn Ser Lys Pro Asn Arg Pro
3365                3370                3375

Ser Leu Ala Lys Ile Leu Leu Ser Leu Asp Gly Asn Leu Ala Lys
3380                3385                3390

Gln Gln Ala Leu Ser His Ile Leu Thr Ala Leu Gln Ile Met Tyr
3395                3400                3405

Ala Arg Asp Ala Val Val Gly Ala Leu Met Pro Ala Ala Met Ile
3410                3415                3420

Ala Pro Val Glu Cys Pro Ser Phe Ser Ser Ala Ala Pro Ser Asp
3425                3430                3435

Ala Ser Ala Met Ala Ser Pro Met Asn Gly Glu Glu Cys Met Leu
3440                3445                3450

Ala Val Asp Ile Glu Asp Arg Leu Ser Pro Asn Pro Trp Gln Glu
3455                3460                3465

Lys Arg Glu Ile Val Ser Ser Glu Asp Ala Val Thr Pro Ser Ala
3470                3475                3480

Val Thr Pro Ser Ala Pro Ser Ala Ser Ala Arg Pro Phe Ile Pro
3485                3490                3495

Val Thr Asp Asp Leu Gly Ala Ala Ser Ile Ile Ala Glu Thr Met
```

-continued

```
            3500                3505                3510
Thr Lys Thr Lys Glu Asp Val Glu Ser Gln Asn Lys Ala Ala Gly
    3515                3520                3525

Pro Glu Pro Gln Ala Leu Asp Glu Phe Thr Ser Leu Leu Ile Ala
    3530                3535                3540

Asp Asp Thr Arg Val Val Val Asp Leu Leu Lys Leu Ser Val Cys
    3545                3550                3555

Ser Arg Ala Gly Asp Arg Gly Arg Asp Val Leu Ser Ala Val Leu
    3560                3565                3570

Ser Gly Met Gly Thr Ala Tyr Pro Gln Val Ala Asp Met Leu Leu
    3575                3580                3585

Glu Leu Cys Val Thr Glu Leu Glu Asp Val Ala Thr Asp Ser Gln
    3590                3595                3600

Ser Gly Arg Leu Ser Ser Gln Pro Val Val Val Glu Ser Ser His
    3605                3610                3615

Pro Tyr Thr Asp Asp Thr Ser Thr Ser Gly Thr Val Lys Ile Pro
    3620                3625                3630

Gly Ala Glu Gly Leu Arg Val Glu Phe Asp Arg Gln Cys Ser Thr
    3635                3640                3645

Glu Arg Arg His Asp Pro Leu Thr Val Met Asp Gly Val Asn Arg
    3650                3655                3660

Ile Val Ser Val Arg Ser Gly Arg Glu Trp Ser Asp Trp Ser Ser
    3665                3670                3675

Glu Leu Arg Ile Pro Gly Asp Glu Leu Lys Trp Lys Phe Ile Ser
    3680                3685                3690

Asp Gly Ser Val Asn Gly Trp Gly Trp Arg Phe Thr Val Tyr Pro
    3695                3700                3705

Ile Met Pro Ala Ala Gly Pro Lys Glu Leu Leu Ser Asp Arg Cys
    3710                3715                3720

Val Leu Ser Cys Pro Ser Met Asp Leu Val Thr Cys Leu Leu Asp
    3725                3730                3735

Phe Arg Leu Asn Leu Ala Ser Asn Arg Ser Ile Val Pro Arg Leu
    3740                3745                3750

Ala Ala Ser Leu Ala Ala Cys Ala Gln Leu Ser Ala Leu Ala Ala
    3755                3760                3765

Ser His Arg Met Trp Ala Leu Gln Arg Leu Arg Lys Leu Leu Thr
    3770                3775                3780

Thr Glu Phe Gly Gln Ser Ile Asn Ile Asn Arg Leu Leu Gly Glu
    3785                3790                3795

Asn Asp Gly Glu Thr Arg Ala Leu Ser Phe Thr Gly Ser Ala Leu
    3800                3805                3810

Ala Ala Leu Val Lys Gly Leu Pro Glu Ala Leu Gln Arg Gln Phe
    3815                3820                3825

Glu Tyr Glu Asp Pro Ile Val Arg Gly Gly Lys Gln Leu Leu His
    3830                3835                3840

Ser Pro Phe Phe Lys Val Leu Val Ala Leu Ala Cys Asp Leu Glu
    3845                3850                3855

Leu Asp Thr Leu Pro Cys Cys Ala Glu Thr His Lys Trp Ala Trp
    3860                3865                3870

Phe Arg Arg Tyr Cys Met Ala Ser Arg Val Ala Val Ala Leu Asp
    3875                3880                3885

Lys Arg Thr Pro Leu Pro Arg Leu Phe Leu Asp Glu Val Ala Lys
    3890                3895                3900
```

-continued

Lys Ile Arg Glu Leu Met Ala Asp Ser Glu Asn Met Asp Val Leu
3905               3910                3915

His Glu Ser His Asp Ile Phe Lys Arg Glu Gln Asp Glu Gln Leu
3920               3925                3930

Val Gln Trp Met Asn Arg Arg Pro Asp Asp Trp Thr Leu Ser Ala
3935               3940                3945

Gly Gly Ser Gly Thr Ile Tyr Gly Trp Gly His Asn His Arg Gly
3950               3955                3960

Gln Leu Gly Gly Ile Glu Gly Ala Lys Val Lys Val Pro Thr Pro
3965               3970                3975

Cys Glu Ala Leu Ala Thr Leu Arg Pro Val Gln Leu Ile Gly Gly
3980               3985                3990

Glu Gln Thr Leu Phe Ala Val Thr Ala Asp Gly Lys Leu Tyr Ala
3995               4000                4005

Thr Gly Tyr Gly Ala Gly Gly Arg Leu Gly Ile Gly Gly Thr Glu
4010               4015                4020

Ser Val Ser Thr Pro Thr Leu Leu Glu Ser Ile Gln His Val Phe
4025               4030                4035

Ile Lys Lys Val Ala Val Asn Ser Gly Gly Lys His Cys Leu Ala
4040               4045                4050

Leu Ser Ser Glu Gly Glu Val Tyr Ser Trp Gly Glu Ala Glu Asp
4055               4060                4065

Gly Lys Leu Gly His Gly Asn Arg Ser Pro Cys Asp Arg Pro Arg
4070               4075                4080

Val Ile Glu Ser Leu Arg Gly Ile Glu Val Val Asp Val Ala Ala
4085               4090                4095

Gly Gly Ala His Ser Ala Cys Val Thr Ala Ala Gly Asp Leu Tyr
4100               4105                4110

Thr Trp Gly Lys Gly Arg Tyr Gly Arg Leu Gly His Ser Asp Ser
4115               4120                4125

Glu Asp Gln Leu Lys Pro Lys Leu Val Glu Ala Leu Gln Gly His
4130               4135                4140

Arg Val Val Asp Ile Ala Cys Gly Ser Gly Asp Ala Gln Thr Leu
4145               4150                4155

Cys Leu Thr Asp Asp Asp Thr Val Trp Ser Trp Gly Asp Gly Asp
4160               4165                4170

Tyr Gly Lys Leu Gly Arg Gly Gly Ser Asp Gly Cys Lys Val Pro
4175               4180                4185

Met Lys Ile Asp Ser Leu Thr Gly Leu Gly Val Val Lys Val Glu
4190               4195                4200

Cys Gly Ser Gln Phe Ser Val Ala Leu Thr Lys Ser Gly Ala Val
4205               4210                4215

Tyr Thr Trp Gly Lys Gly Asp Tyr His Arg Leu Gly His Gly Ser
4220               4225                4230

Asp Asp His Val Arg Arg Pro Arg Gln Val Gln Gly Leu Gln Gly
4235               4240                4245

Lys Lys Val Ile Ala Ile Ala Thr Gly Ser Leu His Cys Val Cys
4250               4255                4260

Cys Thr Glu Asp Gly Glu Val Tyr Thr Trp Gly Asp Asn Asp Glu
4265               4270                4275

Gly Gln Leu Gly Asp Gly Thr Thr Asn Ala Ile Gln Arg Pro Arg
4280               4285                4290

```
Leu Val Ala Ala Leu Gln Gly Lys Lys Val Asn Arg Val Ala Cys
    4295            4300                4305
Gly Ser Ala His Thr Leu Ala Trp Ser Thr Ser Lys Pro Ala Ser
    4310            4315                4320
Ala Gly Lys Leu Pro Ala Gln Val Pro Met Glu Tyr Asn His Leu
    4325            4330                4335
Gln Glu Ile Pro Ile Ile Ala Leu Arg Asn Arg Leu Leu Leu Leu
    4340            4345                4350
His His Leu Ser Glu Leu Phe Cys Pro Cys Ile Pro Met Phe Asp
    4355            4360                4365
Leu Glu Gly Ser Leu Asp Glu Thr Gly Leu Gly Pro Ser Val Gly
    4370            4375                4380
Phe Asp Thr Leu Arg Gly Ile Leu Ile Ser Gln Gly Lys Glu Ala
    4385            4390                4395
Ala Phe Arg Lys Val Val Gln Ala Thr Met Val Arg Asp Arg Gln
    4400            4405                4410
His Gly Pro Val Val Glu Leu Asn Arg Ile Gln Val Lys Arg Ser
    4415            4420                4425
Arg Ser Lys Gly Gly Leu Ala Gly Pro Asp Gly Thr Lys Ser Val
    4430            4435                4440
Phe Gly Gln Met Cys Ala Lys Met Ser Ser Phe Gly Pro Asp Ser
    4445            4450                4455
Leu Leu Leu Pro His Arg Val Trp Lys Val Lys Phe Val Gly Glu
    4460            4465                4470
Ser Val Asp Asp Cys Gly Gly Gly Tyr Ser Glu Ser Ile Ala Glu
    4475            4480                4485
Ile Cys Glu Glu Leu Gln Asn Gly Leu Thr Pro Leu Leu Ile Val
    4490            4495                4500
Thr Pro Asn Gly Arg Asp Glu Ser Gly Ala Asn Arg Asp Cys Tyr
    4505            4510                4515
Leu Leu Ser Pro Ala Ala Arg Ala Pro Val His Ser Ser Met Phe
    4520            4525                4530
Arg Phe Leu Gly Val Leu Leu Gly Ile Ala Ile Arg Thr Gly Ser
    4535            4540                4545
Pro Leu Ser Leu Asn Leu Ala Glu Pro Val Trp Lys Gln Leu Ala
    4550            4555                4560
Gly Met Ser Leu Thr Ile Ala Asp Leu Ser Glu Val Asp Lys Asp
    4565            4570                4575
Phe Ile Pro Gly Leu Met Tyr Ile Arg Asp Asn Glu Ala Thr Ser
    4580            4585                4590
Glu Glu Phe Glu Ala Met Ser Leu Pro Phe Thr Val Pro Ser Ala
    4595            4600                4605
Ser Gly Gln Asp Ile Gln Leu Ser Ser Lys His Thr His Ile Thr
    4610            4615                4620
Leu Asp Asn Arg Ala Glu Tyr Val Arg Leu Ala Ile Asn Tyr Arg
    4625            4630                4635
Leu His Glu Phe Asp Glu Gln Val Ala Ala Val Arg Glu Gly Met
    4640            4645                4650
Ala Arg Val Val Pro Val Pro Leu Leu Ser Leu Phe Thr Gly Tyr
    4655            4660                4665
Glu Leu Glu Thr Met Val Cys Gly Ser Pro Asp Ile Pro Leu His
    4670            4675                4680
Leu Leu Lys Ser Val Ala Thr Tyr Lys Gly Ile Glu Pro Ser Ala
```

```
                    4685                4690                4695
Ser Leu Ile Gln Trp Phe Trp Glu Val Met Ser Phe Ser Asn
    4700                4705                4710

Thr Glu Arg Ser Leu Phe Leu Arg Phe Val Trp Gly Arg Thr Arg
    4715                4720                4725

Leu Pro Arg Thr Ile Ala Asp Phe Arg Gly Arg Asp Phe Val Ile
    4730                4735                4740

Gln Val Leu Asp Lys Tyr Asn Pro Pro Asp His Phe Leu Pro Glu
    4745                4750                4755

Ser Tyr Thr Cys Phe Phe Leu Leu Lys Leu Pro Arg Tyr Ser Cys
    4760                4765                4770

Lys Gln Val Leu Glu Glu Lys Leu Lys Tyr Ala Ile His Phe Cys
    4775                4780                4785

Lys Ser Ile Asp Thr Asp Asp Tyr Ala Arg Ile Ala Leu Thr Gly
    4790                4795                4800

Glu Pro Ala Ala Asp Asp Ser Asp Asp Ser Asp Asn Glu Asp
    4805                4810                4815

Val Asp Ser Phe Ala Ser Ser Thr Gln Asp Tyr Leu Thr Gly
    4820                4825                4830
His

<210> SEQ ID NO 12
<211> LENGTH: 17
<212> TYPE: PRT
<213> ORGANISM: Homo sapiens

<400> SEQUENCE: 12

Lys Leu Ala Glu Leu Pro Ala Ala Ala Gln Pro Ser Ala Glu Asp Ser
1               5                   10                  15
Asp

<210> SEQ ID NO 13
<211> LENGTH: 579
<212> TYPE: PRT
<213> ORGANISM: Homo sapiens

<400> SEQUENCE: 13

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
                20                  25                  30

Ser Ser Thr Ala Thr Asp Val Phe Trp Ala Lys Tyr Thr Ala Cys Glu
            35                  40                  45

Thr Ala Arg Thr Pro Arg Asp Lys Leu Ala Ala Cys Leu Glu Gly Asn
        50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
                100                 105                 110

Phe Cys Arg Asn Pro Asp Ser Ser Thr Thr Gly Pro Trp Cys Tyr Thr
            115                 120                 125

Thr Asp Pro Thr Val Arg Arg Gln Glu Cys Ser Ile Pro Val Cys Gly
        130                 135                 140
```

```
Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
```

```
                        565                 570                 575
Phe Gly Glu

<210> SEQ ID NO 14
<211> LENGTH: 21
<212> TYPE: PRT
<213> ORGANISM: Homo sapiens

<400> SEQUENCE: 14

Thr Ala Thr Ser Glu Tyr Gln Thr Phe Phe Asn Pro Arg Thr Phe Gly
1               5                   10                  15

Ser Gly Glu Ala Asp
            20

<210> SEQ ID NO 15
<211> LENGTH: 127
<212> TYPE: PRT
<213> ORGANISM: Homo sapiens

<400> SEQUENCE: 15

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
                20                  25                  30

Phe Arg Lys Ala Ala Asp Asp Thr Trp Glu Pro Phe Ala Ser Gly Lys
            35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65              70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 16
<211> LENGTH: 20
<212> TYPE: PRT
<213> ORGANISM: Homo sapiens

<400> SEQUENCE: 16

Ala Val Arg Gly Ser Pro Ala Ile Asn Val Ala Val His Val Phe Arg
1               5                   10                  15

Lys Ala Ala Asp
            20

<210> SEQ ID NO 17
<211> LENGTH: 399
<212> TYPE: PRT
<213> ORGANISM: Homo sapiens

<400> SEQUENCE: 17

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
```

```
                35                  40                  45
Val Ser Ala Thr Glu Pro Cys Lys Pro Cys Thr Glu Cys Val Gly Leu
 50                  55                  60

Gln Ser Met Ser Ala Pro Cys Val Glu Ala Asp Asp Ala Val Cys Arg
 65                  70                  75                  80

Cys Ala Tyr Gly Tyr Gln Asp Glu Thr Thr Gly Arg Cys Glu Ala
                 85                  90                  95

Cys Arg Val Cys Glu Ala Gly Ser Gly Leu Val Phe Ser Cys Gln Asp
                100                 105                 110

Lys Gln Asn Thr Val Cys Glu Glu Cys Pro Asp Gly Thr Tyr Ser Asp
                115                 120                 125

Glu Ala Asn His Val Asp Pro Cys Leu Pro Cys Thr Val Cys Glu Asp
                130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
                180                 185                 190

Gln Asp Leu Ile Ala Ser Thr Val Ala Gly Val Val Thr Thr Val Met
                195                 200                 205

Gly Ser Ser Gln Pro Val Val Thr Arg Gly Thr Thr Asp Asn Leu Ile
                210                 215                 220

Pro Val Tyr Cys Ser Ile Leu Ala Ala Val Val Val Gly Leu Val Ala
225                 230                 235                 240

Tyr Ile Ala Phe Lys Arg Trp Asn Ser Cys Lys Gln Asn Lys Gln Gly
                245                 250                 255

Ala Asn Ser Arg Pro Val Asn Gln Thr Pro Pro Glu Gly Glu Lys
                260                 265                 270

Leu His Ser Asp Ser Gly Ile Ser Val Asp Ser Gln Ser Leu His Asp
                275                 280                 285

Gln Gln Pro His Thr Gln Thr Ala Ser Gly Gln Ala Leu Lys Gly Asp
                290                 295                 300

Gly Gly Leu Tyr Ser Ser Leu Pro Pro Ala Lys Arg Glu Glu Val Glu
305                 310                 315                 320

Lys Leu Leu Asn Gly Ser Ala Gly Asp Thr Trp Arg His Leu Ala Gly
                325                 330                 335

Glu Leu Gly Tyr Gln Pro Glu His Ile Asp Ser Phe Thr His Glu Ala
                340                 345                 350

Cys Pro Val Arg Ala Leu Leu Ala Ser Trp Ala Thr Gln Asp Ser Ala
                355                 360                 365

Thr Leu Asp Ala Leu Leu Ala Ala Leu Arg Arg Ile Gln Arg Ala Asp
                370                 375                 380

Leu Val Glu Ser Leu Cys Ser Glu Ser Thr Ala Thr Ser Pro Val
385                 390                 395

<210> SEQ ID NO 18
<211> LENGTH: 16
<212> TYPE: PRT
<213> ORGANISM: Homo sapiens

<400> SEQUENCE: 18

Gln Thr Ala Ser Gly Gln Ala Leu Lys Gly Asp Gly Gly Leu Tyr Ser
 1               5                  10                  15
```

```
<210> SEQ ID NO 19
<211> LENGTH: 1725
<212> TYPE: PRT
<213> ORGANISM: Homo sapiens

<400> SEQUENCE: 19

Lys Pro Arg Leu Leu Leu Phe Ser Pro Ser Val His Leu Gly Val
1               5                   10                  15

Pro Leu Ser Val Gly Val Gln Leu Gln Asp Val Pro Arg Gly Gln Val
            20                  25                  30

Val Lys Gly Ser Val Phe Leu Arg Asn Pro Ser Arg Asn Asn Val Pro
        35                  40                  45

Cys Ser Pro Lys Val Asp Phe Thr Leu Ser Ser Glu Arg Asp Phe Ala
50                  55                  60

Leu Leu Ser Leu Gln Val Pro Leu Lys Asp Ala Lys Ser Cys Gly Leu
65                  70                  75                  80

His Gln Leu Leu Arg Gly Pro Glu Val Gln Leu Val Ala His Ser Pro
                85                  90                  95

Trp Leu Lys Asp Ser Leu Ser Arg Thr Thr Asn Ile Gln Gly Ile Asn
            100                 105                 110

Leu Leu Phe Ser Ser Arg Arg Gly His Leu Phe Leu Gln Thr Asp Gln
        115                 120                 125

Pro Ile Tyr Asn Pro Gly Gln Arg Val Arg Tyr Arg Val Phe Ala Leu
    130                 135                 140

Asp Gln Lys Met Arg Pro Ser Thr Asp Thr Ile Thr Val Met Val Glu
145                 150                 155                 160

Asn Ser His Gly Leu Arg Val Arg Lys Lys Glu Val Tyr Met Pro Ser
                165                 170                 175

Ser Ile Phe Gln Asp Asp Phe Val Ile Pro Asp Ile Ser Glu Pro Gly
            180                 185                 190

Thr Trp Lys Ile Ser Ala Arg Phe Ser Asp Gly Leu Glu Ser Asn Ser
        195                 200                 205

Ser Thr Gln Phe Glu Val Lys Lys Tyr Val Leu Pro Asn Phe Glu Val
    210                 215                 220

Lys Ile Thr Pro Gly Lys Pro Tyr Ile Leu Thr Val Pro Gly His Leu
225                 230                 235                 240

Asp Glu Met Gln Leu Asp Ile Gln Ala Arg Tyr Ile Tyr Gly Lys Pro
                245                 250                 255

Val Gln Gly Val Ala Tyr Val Arg Phe Gly Leu Leu Asp Glu Asp Gly
            260                 265                 270

Lys Lys Thr Phe Phe Arg Gly Leu Glu Ser Gln Thr Lys Leu Val Asn
        275                 280                 285

Gly Gln Ser His Ile Ser Leu Ser Lys Ala Glu Phe Gln Asp Ala Leu
    290                 295                 300

Glu Lys Leu Asn Met Gly Ile Thr Asp Leu Gln Gly Leu Arg Leu Tyr
305                 310                 315                 320

Val Ala Ala Ala Ile Ile Glu Ser Pro Gly Gly Glu Met Glu Glu Ala
                325                 330                 335

Glu Leu Thr Ser Trp Tyr Phe Val Ser Ser Pro Phe Ser Leu Asp Leu
            340                 345                 350

Ser Lys Thr Lys Arg His Leu Val Pro Gly Ala Pro Phe Leu Leu Gln
        355                 360                 365

Ala Leu Val Arg Glu Met Ser Gly Ser Pro Ala Ser Gly Ile Pro Val
    370                 375                 380
```

```
Lys Val Ser Ala Thr Val Ser Pro Gly Ser Val Pro Glu Val Gln
385                 390                 395                 400

Asp Ile Gln Gln Asn Thr Asp Gly Ser Gly Gln Val Ser Ile Pro Ile
            405                 410                 415

Ile Ile Pro Gln Thr Ile Ser Glu Leu Gln Leu Ser Val Ser Ala Gly
        420                 425                 430

Ser Pro His Pro Ala Ile Ala Arg Leu Thr Val Ala Ala Pro Pro Ser
        435                 440                 445

Gly Gly Pro Gly Phe Leu Ser Ile Glu Arg Pro Asp Ser Arg Pro Pro
        450                 455                 460

Arg Val Gly Asp Thr Leu Asn Leu Asn Leu Arg Ala Val Gly Ser Gly
465                 470                 475                 480

Ala Thr Phe Ser His Tyr Tyr Tyr Met Ile Leu Ser Arg Gly Gln Ile
            485                 490                 495

Val Phe Met Asn Arg Glu Pro Lys Arg Thr Leu Thr Ser Val Ser Val
            500                 505                 510

Phe Val Asp His His Leu Ala Pro Ser Phe Tyr Phe Val Ala Phe Tyr
            515                 520                 525

Tyr His Gly Asp His Pro Val Ala Asn Ser Leu Arg Val Asp Val Gln
            530                 535                 540

Ala Gly Ala Cys Glu Gly Lys Leu Glu Leu Ser Val Asp Gly Ala Lys
545                 550                 555                 560

Gln Tyr Arg Asn Gly Glu Ser Val Lys Leu His Leu Glu Thr Asp Ser
            565                 570                 575

Leu Ala Leu Val Ala Leu Gly Ala Leu Asp Thr Ala Leu Tyr Ala Ala
            580                 585                 590

Gly Ser Lys Ser His Lys Pro Leu Asn Met Gly Lys Val Phe Glu Ala
            595                 600                 605

Met Asn Ser Tyr Asp Leu Gly Cys Gly Pro Gly Gly Gly Asp Ser Ala
            610                 615                 620

Leu Gln Val Phe Gln Ala Ala Gly Leu Ala Phe Ser Asp Gly Asp Gln
625                 630                 635                 640

Trp Thr Leu Ser Arg Lys Arg Leu Ser Cys Pro Lys Glu Lys Thr Thr
            645                 650                 655

Arg Lys Lys Arg Asn Val Asn Phe Gln Lys Ala Ile Asn Glu Lys Leu
            660                 665                 670

Gly Gln Tyr Ala Ser Pro Thr Ala Lys Arg Cys Cys Gln Asp Gly Val
            675                 680                 685

Thr Arg Leu Pro Met Met Arg Ser Cys Glu Gln Arg Ala Ala Arg Val
            690                 695                 700

Gln Gln Pro Asp Cys Arg Glu Pro Phe Leu Ser Cys Cys Gln Phe Ala
705                 710                 715                 720

Glu Ser Leu Arg Lys Lys Ser Arg Asp Lys Gly Gln Ala Gly Leu Gln
            725                 730                 735

Arg Ala Leu Glu Ile Leu Gln Glu Glu Asp Leu Ile Asp Glu Asp Asp
            740                 745                 750

Ile Pro Val Arg Ser Phe Phe Pro Glu Asn Trp Leu Trp Arg Val Glu
            755                 760                 765

Thr Val Asp Arg Phe Gln Ile Leu Thr Leu Trp Leu Pro Asp Ser Leu
            770                 775                 780

Thr Thr Trp Glu Ile His Gly Leu Ser Leu Ser Lys Thr Lys Gly Leu
785                 790                 795                 800
```

```
Cys Val Ala Thr Pro Val Gln Leu Arg Val Phe Arg Glu Phe His Leu
            805                 810                 815

His Leu Arg Leu Pro Met Ser Val Arg Arg Phe Glu Gln Leu Glu Leu
            820                 825                 830

Arg Pro Val Leu Tyr Asn Tyr Leu Asp Lys Asn Leu Thr Val Ser Val
            835                 840                 845

His Val Ser Pro Val Glu Gly Leu Cys Leu Ala Gly Gly Gly Gly Leu
850                 855                 860

Ala Gln Gln Val Leu Val Pro Ala Gly Ser Ala Arg Pro Val Ala Phe
865                 870                 875                 880

Ser Val Val Pro Thr Ala Ala Ala Val Ser Leu Lys Val Val Ala
                885                 890                 895

Arg Gly Ser Phe Glu Phe Pro Val Gly Asp Ala Val Ser Lys Val Leu
            900                 905                 910

Gln Ile Glu Lys Glu Gly Ala Ile His Arg Glu Glu Leu Val Tyr Glu
            915                 920                 925

Leu Asn Pro Leu Asp His Arg Gly Arg Thr Leu Glu Ile Pro Gly Asn
            930                 935                 940

Ser Asp Pro Asn Met Ile Pro Asp Gly Asp Phe Asn Ser Tyr Val Arg
945                 950                 955                 960

Val Thr Ala Ser Asp Pro Leu Asp Thr Leu Gly Ser Glu Gly Ala Leu
                965                 970                 975

Ser Pro Gly Gly Val Ala Ser Leu Leu Arg Leu Pro Arg Gly Cys Gly
            980                 985                 990

Glu Gln Thr Met Ile Tyr Leu Ala Pro Thr Leu Ala Ala Ser Arg Tyr
            995                 1000                1005

Leu Asp Lys Thr Glu Gln Trp Ser Thr Leu Pro Pro Glu Thr Lys
            1010                1015                1020

Asp His Ala Val Asp Leu Ile Gln Lys Gly Tyr Met Arg Ile Gln
            1025                1030                1035

Gln Phe Arg Lys Ala Asp Gly Ser Tyr Ala Ala Trp Leu Ser Arg
            1040                1045                1050

Asp Ser Ser Thr Trp Leu Thr Ala Phe Val Leu Lys Val Leu Ser
            1055                1060                1065

Leu Ala Gln Glu Gln Val Gly Gly Ser Pro Glu Lys Leu Gln Glu
            1070                1075                1080

Thr Ser Asn Trp Leu Leu Ser Gln Gln Gln Ala Asp Gly Ser Phe
            1085                1090                1095

Gln Asp Pro Cys Pro Val Leu Asp Arg Ser Met Gln Gly Gly Leu
            1100                1105                1110

Val Gly Asn Asp Glu Thr Val Ala Leu Thr Ala Phe Val Thr Ile
            1115                1120                1125

Ala Leu His His Gly Leu Ala Val Phe Gln Asp Glu Gly Ala Glu
            1130                1135                1140

Pro Leu Lys Gln Arg Val Glu Ala Ser Ile Ser Lys Ala Asn Ser
            1145                1150                1155

Phe Leu Gly Glu Lys Ala Ser Ala Gly Leu Leu Gly Ala His Ala
            1160                1165                1170

Ala Ala Ile Thr Ala Tyr Ala Leu Ser Leu Thr Lys Ala Pro Val
            1175                1180                1185

Asp Leu Leu Gly Val Ala His Asn Asn Leu Met Ala Met Ala Gln
            1190                1195                1200

Glu Thr Gly Asp Asn Leu Tyr Trp Gly Ser Val Thr Gly Ser Gln
```

```
            1205                1210                1215

Ser Asn Ala Val Ser Pro Thr Pro Ala Pro Arg Asn Pro Ser Asp
1220                1225                1230

Pro Met Pro Gln Ala Pro Ala Leu Trp Ile Glu Thr Thr Ala Tyr
1235                1240                1245

Ala Leu Leu His Leu Leu Leu His Glu Gly Lys Ala Glu Met Ala
1250                1255                1260

Asp Gln Ala Ser Ala Trp Leu Thr Arg Gln Gly Ser Phe Gln Gly
1265                1270                1275

Gly Phe Arg Ser Thr Gln Asp Thr Val Ile Ala Leu Asp Ala Leu
1280                1285                1290

Ser Ala Tyr Trp Ile Ala Ser His Thr Thr Glu Glu Arg Gly Leu
1295                1300                1305

Asn Val Thr Leu Ser Ser Thr Gly Arg Asn Gly Phe Lys Ser His
1310                1315                1320

Ala Leu Gln Leu Asn Asn Arg Gln Ile Arg Gly Leu Glu Glu Glu
1325                1330                1335

Leu Gln Phe Ser Leu Gly Ser Lys Ile Asn Val Lys Val Gly Gly
1340                1345                1350

Asn Ser Lys Gly Thr Leu Lys Val Leu Arg Thr Tyr Asn Val Leu
1355                1360                1365

Asp Met Lys Asn Thr Thr Cys Gln Asp Leu Gln Ile Glu Val Thr
1370                1375                1380

Val Lys Gly His Val Glu Tyr Thr Met Glu Ala Asn Glu Asp Tyr
1385                1390                1395

Glu Asp Tyr Glu Tyr Asp Glu Leu Pro Ala Lys Asp Asp Pro Asp
1400                1405                1410

Ala Pro Leu Gln Pro Val Thr Pro Leu Gln Leu Phe Glu Gly Arg
1415                1420                1425

Arg Asn Arg Arg Arg Glu Ala Pro Lys Val Val Glu Glu Gln
1430                1435                1440

Glu Ser Arg Val His Tyr Thr Val Cys Ile Trp Arg Asn Gly Lys
1445                1450                1455

Val Gly Leu Ser Gly Met Ala Ile Ala Asp Val Thr Leu Leu Ser
1460                1465                1470

Gly Phe His Ala Leu Arg Ala Asp Leu Glu Lys Leu Thr Ser Leu
1475                1480                1485

Ser Asp Arg Tyr Val Ser His Phe Glu Thr Glu Gly Pro His Val
1490                1495                1500

Leu Leu Tyr Phe Asp Ser Val Pro Thr Ser Arg Glu Cys Val Gly
1505                1510                1515

Phe Glu Ala Val Gln Glu Val Pro Val Gly Leu Val Gln Pro Ala
1520                1525                1530

Ser Ala Thr Leu Tyr Asp Tyr Tyr Asn Pro Glu Arg Arg Cys Ser
1535                1540                1545

Val Phe Tyr Gly Ala Pro Ser Lys Ser Arg Leu Leu Ala Thr Leu
1550                1555                1560

Cys Ser Ala Glu Val Cys Gln Cys Ala Glu Gly Lys Cys Pro Arg
1565                1570                1575

Gln Arg Arg Ala Leu Glu Arg Gly Leu Gln Asp Glu Asp Gly Tyr
1580                1585                1590

Arg Met Lys Phe Ala Cys Tyr Tyr Pro Arg Val Glu Tyr Gly Phe
1595                1600                1605
```

```
Gln Val Lys Val Leu Arg Glu Asp Ser Arg Ala Ala Phe Arg Leu
    1610            1615                1620

Phe Glu Thr Lys Ile Thr Gln Val Leu His Phe Thr Lys Asp Val
    1625            1630                1635

Lys Ala Ala Ala Asn Gln Met Arg Asn Phe Leu Val Arg Ala Ser
    1640            1645                1650

Cys Arg Leu Arg Leu Glu Pro Gly Lys Glu Tyr Leu Ile Met Gly
    1655            1660                1665

Leu Asp Gly Ala Thr Tyr Asp Leu Glu Gly His Pro Gln Tyr Leu
    1670            1675                1680

Leu Asp Ser Asn Ser Trp Ile Glu Glu Met Pro Ser Glu Arg Leu
    1685            1690                1695

Cys Arg Ser Thr Arg Gln Arg Ala Ala Cys Ala Gln Leu Asn Asp
    1700            1705                1710

Phe Leu Gln Glu Tyr Gly Thr Gln Gly Cys Gln Val
    1715            1720                1725

<210> SEQ ID NO 20
<211> LENGTH: 16
<212> TYPE: PRT
<213> ORGANISM: Homo sapiens

<400> SEQUENCE: 20

Asn Gly Phe Lys Ser His Ala Leu Gln Leu Asn Asn Arg Gln Ile Arg
1               5                   10                  15

<210> SEQ ID NO 21
<211> LENGTH: 1725
<212> TYPE: PRT
<213> ORGANISM: Homo sapiens

<400> SEQUENCE: 21

Lys Pro Arg Leu Leu Phe Ser Pro Ser Val Val His Leu Gly Val
1               5                   10                  15

Pro Leu Ser Val Gly Val Gln Leu Gln Asp Val Pro Arg Gly Gln Val
                20                  25                  30

Val Lys Gly Ser Val Phe Leu Arg Asn Pro Ser Arg Asn Asn Val Pro
                35                  40                  45

Cys Ser Pro Lys Val Asp Phe Thr Leu Ser Ser Glu Arg Asp Phe Ala
    50                  55                  60

Leu Leu Ser Leu Gln Val Pro Leu Lys Asp Ala Lys Ser Cys Gly Leu
65                  70                  75                  80

His Gln Leu Leu Arg Gly Pro Glu Val Gln Leu Val Ala His Ser Pro
                85                  90                  95

Trp Leu Lys Asp Ser Leu Ser Arg Thr Thr Asn Ile Gln Gly Ile Asn
                100                 105                 110

Leu Leu Phe Ser Ser Arg Arg Gly His Leu Phe Leu Gln Thr Asp Gln
                115                 120                 125

Pro Ile Tyr Asn Pro Gly Gln Arg Val Arg Tyr Arg Val Phe Ala Leu
        130                 135                 140

Asp Gln Lys Met Arg Pro Ser Thr Asp Thr Ile Thr Val Met Val Glu
145                 150                 155                 160

Asn Ser His Gly Leu Arg Val Arg Lys Lys Glu Val Tyr Met Pro Ser
                165                 170                 175

Ser Ile Phe Gln Asp Asp Phe Val Ile Pro Asp Ile Ser Glu Pro Gly
            180                 185                 190
```

```
Thr Trp Lys Ile Ser Ala Arg Phe Ser Asp Gly Leu Glu Ser Asn Ser
        195                 200                 205

Ser Thr Gln Phe Glu Val Lys Lys Tyr Val Leu Pro Asn Phe Glu Val
    210                 215                 220

Lys Ile Thr Pro Gly Lys Pro Tyr Ile Leu Thr Val Pro Gly His Leu
225                 230                 235                 240

Asp Glu Met Gln Leu Asp Ile Gln Ala Arg Tyr Ile Tyr Gly Lys Pro
                245                 250                 255

Val Gln Gly Val Ala Tyr Val Arg Phe Gly Leu Leu Asp Glu Asp Gly
                260                 265                 270

Lys Lys Thr Phe Phe Arg Gly Leu Glu Ser Gln Thr Lys Leu Val Asn
            275                 280                 285

Gly Gln Ser His Ile Ser Leu Ser Lys Ala Glu Phe Gln Asp Ala Leu
            290                 295                 300

Glu Lys Leu Asn Met Gly Ile Thr Asp Leu Gln Gly Leu Arg Leu Tyr
305                 310                 315                 320

Val Ala Ala Ala Ile Ile Glu Ser Pro Gly Gly Met Glu Glu Ala
                325                 330                 335

Glu Leu Thr Ser Trp Tyr Phe Val Ser Ser Pro Phe Ser Leu Asp Leu
            340                 345                 350

Ser Lys Thr Lys Arg His Leu Val Pro Gly Ala Pro Phe Leu Leu Gln
            355                 360                 365

Ala Leu Val Arg Glu Met Ser Gly Ser Pro Ala Ser Gly Ile Pro Val
    370                 375                 380

Lys Val Ser Ala Thr Val Ser Ser Pro Gly Ser Val Pro Glu Val Gln
385                 390                 395                 400

Asp Ile Gln Gln Asn Thr Asp Gly Ser Gly Gln Val Ser Ile Pro Ile
                405                 410                 415

Ile Ile Pro Gln Thr Ile Ser Glu Leu Gln Leu Ser Val Ser Ala Gly
            420                 425                 430

Ser Pro His Pro Ala Ile Ala Arg Leu Thr Val Ala Ala Pro Pro Ser
        435                 440                 445

Gly Gly Pro Gly Phe Leu Ser Ile Glu Arg Pro Asp Ser Arg Pro Pro
    450                 455                 460

Arg Val Gly Asp Thr Leu Asn Leu Asn Leu Arg Ala Val Gly Ser Gly
465                 470                 475                 480

Ala Thr Phe Ser His Tyr Tyr Tyr Met Ile Leu Ser Arg Gly Gln Ile
                485                 490                 495

Val Phe Met Asn Arg Glu Pro Lys Arg Thr Leu Thr Ser Val Ser Val
            500                 505                 510

Phe Val Asp His His Leu Ala Pro Ser Phe Tyr Phe Val Ala Phe Tyr
        515                 520                 525

Tyr His Gly Asp His Pro Val Ala Asn Ser Leu Arg Val Asp Val Gln
    530                 535                 540

Ala Gly Ala Cys Glu Gly Lys Leu Glu Leu Ser Val Asp Gly Ala Lys
545                 550                 555                 560

Gln Tyr Arg Asn Gly Glu Ser Val Lys Leu His Leu Glu Thr Asp Ser
                565                 570                 575

Leu Ala Leu Val Ala Leu Gly Ala Leu Asp Thr Ala Leu Tyr Ala Ala
            580                 585                 590

Gly Ser Lys Ser His Lys Pro Leu Asn Met Gly Lys Val Phe Glu Ala
        595                 600                 605
```

```
Met Asn Ser Tyr Asp Leu Gly Cys Gly Pro Gly Gly Asp Ser Ala
610                 615                 620

Leu Gln Val Phe Gln Ala Ala Gly Leu Ala Phe Ser Asp Gly Asp Gln
625                 630                 635                 640

Trp Thr Leu Ser Arg Lys Arg Leu Ser Cys Pro Lys Glu Lys Thr Thr
                645                 650                 655

Arg Lys Lys Arg Asn Val Asn Phe Gln Lys Ala Ile Asn Glu Lys Leu
                660                 665                 670

Gly Gln Tyr Ala Ser Pro Thr Ala Lys Arg Cys Cys Gln Asp Gly Val
            675                 680                 685

Thr Arg Leu Pro Met Met Arg Ser Cys Glu Gln Arg Ala Ala Arg Val
690                 695                 700

Gln Gln Pro Asp Cys Arg Glu Pro Phe Leu Ser Cys Cys Gln Phe Ala
705                 710                 715                 720

Glu Ser Leu Arg Lys Lys Ser Arg Asp Lys Gly Gln Ala Gly Leu Gln
                725                 730                 735

Arg Ala Leu Glu Ile Leu Gln Glu Glu Asp Leu Ile Asp Glu Asp
                740                 745                 750

Ile Pro Val Arg Ser Phe Phe Pro Glu Asn Trp Leu Trp Arg Val Glu
            755                 760                 765

Thr Val Asp Arg Phe Gln Ile Leu Thr Leu Trp Leu Pro Asp Ser Leu
770                 775                 780

Thr Thr Trp Glu Ile His Gly Leu Ser Leu Ser Lys Thr Lys Gly Leu
785                 790                 795                 800

Cys Val Ala Thr Pro Val Gln Leu Arg Val Phe Arg Glu Phe His Leu
                805                 810                 815

His Leu Arg Leu Pro Met Ser Val Arg Arg Phe Glu Gln Leu Glu Leu
            820                 825                 830

Arg Pro Val Leu Tyr Asn Tyr Leu Asp Lys Asn Leu Thr Val Ser Val
            835                 840                 845

His Val Ser Pro Val Glu Gly Leu Cys Leu Ala Gly Gly Gly Gly Leu
850                 855                 860

Ala Gln Gln Val Leu Val Pro Ala Gly Ser Ala Arg Pro Val Ala Phe
865                 870                 875                 880

Ser Val Val Pro Thr Ala Ala Ala Val Ser Leu Lys Val Val Ala
                885                 890                 895

Arg Gly Ser Phe Glu Phe Pro Val Gly Asp Ala Val Ser Lys Val Leu
            900                 905                 910

Gln Ile Glu Lys Glu Gly Ala Ile His Arg Glu Glu Leu Val Tyr Glu
            915                 920                 925

Leu Asn Pro Leu Asp His Arg Gly Arg Thr Leu Glu Ile Pro Gly Asn
930                 935                 940

Ser Asp Pro Asn Met Ile Pro Asp Gly Asp Phe Asn Ser Tyr Val Arg
945                 950                 955                 960

Val Thr Ala Ser Asp Pro Leu Asp Thr Leu Gly Ser Glu Gly Ala Leu
                965                 970                 975

Ser Pro Gly Gly Val Ala Ser Leu Leu Arg Leu Pro Arg Gly Cys Gly
            980                 985                 990

Glu Gln Thr Met Ile Tyr Leu Ala Pro Thr Leu Ala Ala Ser Arg Tyr
            995                 1000                1005

Leu Asp Lys Thr Glu Gln Trp Ser Thr Leu Pro Pro Glu Thr Lys
            1010                1015                1020

Asp His Ala Val Asp Leu Ile Gln Lys Gly Tyr Met Arg Ile Gln
```

```
                 1025                1030                1035
Gln Phe Arg Lys Ala Asp Gly Ser Tyr Ala Ala Trp Leu Ser Arg
    1040                1045                1050
Asp Ser Ser Thr Trp Leu Thr Ala Phe Val Leu Lys Val Leu Ser
    1055                1060                1065
Leu Ala Gln Glu Gln Val Gly Gly Ser Pro Glu Lys Leu Gln Glu
    1070                1075                1080
Thr Ser Asn Trp Leu Leu Ser Gln Gln Gln Ala Asp Gly Ser Phe
    1085                1090                1095
Gln Asp Leu Ser Pro Val Ile His Arg Ser Met Gln Gly Gly Leu
    1100                1105                1110
Val Gly Asn Asp Glu Thr Val Ala Leu Thr Ala Phe Val Thr Ile
    1115                1120                1125
Ala Leu His His Gly Leu Ala Val Phe Gln Asp Glu Gly Ala Glu
    1130                1135                1140
Pro Leu Lys Gln Arg Val Glu Ala Ser Ile Ser Lys Ala Asn Ser
    1145                1150                1155
Phe Leu Gly Glu Lys Ala Ser Ala Gly Leu Leu Gly Ala His Ala
    1160                1165                1170
Ala Ala Ile Thr Ala Tyr Ala Leu Ser Leu Thr Lys Ala Pro Val
    1175                1180                1185
Asp Leu Leu Gly Val Ala His Asn Asn Leu Met Ala Met Ala Gln
    1190                1195                1200
Glu Thr Gly Asp Asn Leu Tyr Trp Gly Ser Val Thr Gly Ser Gln
    1205                1210                1215
Ser Asn Ala Val Ser Pro Thr Pro Ala Pro Arg Asn Pro Ser Asp
    1220                1225                1230
Pro Met Pro Gln Ala Pro Ala Leu Trp Ile Glu Thr Thr Ala Tyr
    1235                1240                1245
Ala Leu Leu His Leu Leu Leu His Glu Gly Lys Ala Glu Met Ala
    1250                1255                1260
Asp Gln Ala Ser Ala Trp Leu Thr Arg Gln Gly Ser Phe Gln Gly
    1265                1270                1275
Gly Phe Arg Ser Thr Gln Asp Thr Val Ile Ala Leu Asp Ala Leu
    1280                1285                1290
Ser Ala Tyr Trp Ile Ala Ser His Thr Thr Glu Glu Arg Gly Leu
    1295                1300                1305
Asn Val Thr Leu Ser Ser Thr Gly Arg Asn Gly Phe Lys Ser His
    1310                1315                1320
Ala Leu Gln Leu Asn Asn Arg Gln Ile Arg Gly Leu Glu Glu Glu
    1325                1330                1335
Leu Gln Phe Ser Leu Gly Ser Lys Ile Asn Val Lys Val Gly Gly
    1340                1345                1350
Asn Ser Lys Gly Thr Leu Lys Val Leu Arg Thr Tyr Asn Val Leu
    1355                1360                1365
Asp Met Lys Asn Thr Thr Cys Gln Asp Leu Gln Ile Glu Val Thr
    1370                1375                1380
Val Lys Gly His Val Glu Tyr Thr Met Glu Ala Asn Glu Asp Tyr
    1385                1390                1395
Glu Asp Tyr Glu Tyr Asp Glu Leu Pro Ala Lys Asp Asp Pro Asp
    1400                1405                1410
Ala Pro Leu Gln Pro Val Thr Pro Leu Gln Leu Phe Glu Gly Arg
    1415                1420                1425
```

```
Arg Asn Arg Arg Arg Arg Glu Ala Pro Lys Val Val Glu Glu Gln
    1430                1435                1440

Glu Ser Arg Val His Tyr Thr Val Cys Ile Trp Arg Asn Gly Lys
    1445                1450                1455

Val Gly Leu Ser Gly Met Ala Ile Ala Asp Val Thr Leu Leu Ser
    1460                1465                1470

Gly Phe His Ala Leu Arg Ala Asp Leu Glu Lys Leu Thr Ser Leu
    1475                1480                1485

Ser Asp Arg Tyr Val Ser His Phe Glu Thr Glu Gly Pro His Val
    1490                1495                1500

Leu Leu Tyr Phe Asp Ser Val Pro Thr Ser Arg Glu Cys Val Gly
    1505                1510                1515

Phe Glu Ala Val Gln Glu Val Pro Val Gly Leu Val Gln Pro Ala
    1520                1525                1530

Ser Ala Thr Leu Tyr Asp Tyr Tyr Asn Pro Glu Arg Arg Cys Ser
    1535                1540                1545

Val Phe Tyr Gly Ala Pro Ser Lys Ser Arg Leu Leu Ala Thr Leu
    1550                1555                1560

Cys Ser Ala Glu Val Cys Gln Cys Ala Glu Gly Lys Cys Pro Arg
    1565                1570                1575

Gln Arg Arg Ala Leu Glu Arg Gly Leu Gln Asp Glu Asp Gly Tyr
    1580                1585                1590

Arg Met Lys Phe Ala Cys Tyr Tyr Pro Arg Val Glu Tyr Gly Phe
    1595                1600                1605

Gln Val Lys Val Leu Arg Glu Asp Ser Arg Ala Ala Phe Arg Leu
    1610                1615                1620

Phe Glu Thr Lys Ile Thr Gln Val Leu His Phe Thr Lys Asp Val
    1625                1630                1635

Lys Ala Ala Ala Asn Gln Met Arg Asn Phe Leu Val Arg Ala Ser
    1640                1645                1650

Cys Arg Leu Arg Leu Glu Pro Gly Lys Glu Tyr Leu Ile Met Gly
    1655                1660                1665

Leu Asp Gly Ala Thr Tyr Asp Leu Glu Gly His Pro Gln Tyr Leu
    1670                1675                1680

Leu Asp Ser Asn Ser Trp Ile Glu Glu Met Pro Ser Glu Arg Leu
    1685                1690                1695

Cys Arg Ser Thr Arg Gln Arg Ala Ala Cys Ala Gln Leu Asn Asp
    1700                1705                1710

Phe Leu Gln Glu Tyr Gly Thr Gln Gly Cys Gln Val
    1715                1720                1725

<210> SEQ ID NO 22
<211> LENGTH: 17
<212> TYPE: PRT
<213> ORGANISM: Homo sapiens

<400> SEQUENCE: 22

Ala Pro Leu Gln Pro Val Thr Pro Leu Gln Leu Phe Glu Gly Arg Arg
1               5                   10                  15

Asn

<210> SEQ ID NO 23
<211> LENGTH: 831
<212> TYPE: PRT
<213> ORGANISM: Homo sapiens
```

<400> SEQUENCE: 23

```
Gly Pro Arg Val Val Glu Arg His Gln Ser Ala Cys Lys Asp Ser Asp
1               5                   10                  15

Trp Pro Phe Cys Ser Asp Glu Asp Trp Asn Tyr Lys Cys Pro Ser Gly
            20                  25                  30

Cys Arg Met Lys Gly Leu Ile Asp Glu Val Asn Gln Asp Phe Thr Asn
        35                  40                  45

Arg Ile Asn Lys Leu Lys Asn Ser Leu Phe Glu Tyr Gln Lys Asn Asn
    50                  55                  60

Lys Asp Ser His Ser Leu Thr Thr Asn Ile Met Glu Ile Leu Arg Gly
65                  70                  75                  80

Asp Phe Ser Ser Ala Asn Asn Arg Asp Asn Thr Tyr Asn Arg Val Ser
                85                  90                  95

Glu Asp Leu Arg Ser Arg Ile Glu Val Leu Lys Arg Lys Val Ile Glu
            100                 105                 110

Lys Val Gln His Ile Gln Leu Leu Gln Lys Asn Val Arg Ala Gln Leu
        115                 120                 125

Val Asp Met Lys Arg Leu Glu Val Asp Ile Asp Ile Lys Ile Arg Ser
130                 135                 140

Cys Arg Gly Ser Cys Ser Arg Ala Leu Ala Arg Glu Val Asp Leu Lys
145                 150                 155                 160

Asp Tyr Glu Asp Gln Gln Lys Gln Leu Glu Gln Val Ile Ala Lys Asp
                165                 170                 175

Leu Leu Pro Ser Arg Asp Arg Gln His Leu Pro Leu Ile Lys Met Lys
            180                 185                 190

Pro Val Pro Asp Leu Val Pro Gly Asn Phe Lys Ser Gln Leu Gln Lys
        195                 200                 205

Val Pro Pro Glu Trp Lys Ala Leu Thr Asp Met Pro Gln Met Arg Met
210                 215                 220

Glu Leu Glu Arg Pro Gly Gly Asn Glu Ile Thr Arg Gly Gly Ser Thr
225                 230                 235                 240

Ser Tyr Gly Thr Gly Ser Glu Thr Glu Ser Pro Arg Asn Pro Ser Ser
                245                 250                 255

Ala Gly Ser Trp Asn Ser Gly Ser Ser Gly Pro Gly Ser Thr Gly Asn
            260                 265                 270

Arg Asn Pro Gly Ser Ser Gly Thr Gly Gly Thr Ala Thr Trp Lys Pro
        275                 280                 285

Gly Ser Ser Gly Pro Gly Ser Thr Gly Ser Trp Asn Ser Gly Ser Ser
290                 295                 300

Gly Thr Gly Ser Thr Gly Asn Gln Asn Pro Gly Ser Pro Arg Pro Gly
305                 310                 315                 320

Ser Thr Gly Thr Trp Asn Pro Gly Ser Ser Glu Arg Gly Ser Ala Gly
                325                 330                 335

His Trp Thr Ser Glu Ser Ser Val Ser Gly Ser Thr Gly Gln Trp His
            340                 345                 350

Ser Glu Ser Gly Ser Phe Arg Pro Asp Ser Pro Gly Ser Gly Asn Ala
        355                 360                 365

Arg Pro Asn Asn Pro Asp Trp Gly Thr Phe Glu Glu Val Ser Gly Asn
        370                 375                 380

Val Ser Pro Gly Thr Arg Arg Glu Tyr His Thr Glu Lys Leu Val Thr
385                 390                 395                 400

Ser Lys Gly Asp Lys Glu Leu Arg Thr Gly Lys Glu Lys Val Thr Ser
```

```
                    405                 410                 415
Gly Ser Thr Thr Thr Thr Arg Arg Ser Cys Ser Lys Thr Val Thr Lys
                420                 425                 430

Thr Val Ile Gly Pro Asp Gly His Lys Glu Val Thr Lys Glu Val Val
                435                 440                 445

Thr Ser Glu Asp Gly Ser Asp Cys Pro Glu Ala Met Asp Leu Gly Thr
450                 455                 460

Leu Ser Gly Ile Gly Thr Leu Asp Gly Phe Arg His Arg His Pro Asp
465                 470                 475                 480

Glu Ala Ala Phe Phe Asp Thr Ala Ser Thr Gly Lys Thr Phe Pro Gly
                485                 490                 495

Phe Phe Ser Pro Met Leu Gly Glu Phe Val Ser Glu Thr Glu Ser Arg
                500                 505                 510

Gly Ser Glu Ser Gly Ile Phe Thr Asn Thr Lys Glu Ser Ser Ser His
                515                 520                 525

His Pro Gly Ile Ala Glu Phe Pro Ser Arg Gly Lys Ser Ser Ser Tyr
                530                 535                 540

Ser Lys Gln Phe Thr Ser Ser Thr Ser Tyr Asn Arg Gly Asp Ser Thr
545                 550                 555                 560

Phe Glu Ser Lys Ser Tyr Lys Met Ala Asp Glu Ala Gly Ser Glu Ala
                565                 570                 575

Asp His Glu Gly Thr His Ser Thr Lys Arg Gly His Ala Lys Ser Arg
                580                 585                 590

Pro Val Arg Asp Cys Asp Asp Val Leu Gln Thr His Pro Ser Gly Thr
                595                 600                 605

Gln Ser Gly Ile Phe Asn Ile Lys Leu Pro Gly Ser Ser Lys Ile Phe
                610                 615                 620

Ser Val Tyr Cys Asp Gln Glu Thr Ser Leu Gly Gly Trp Leu Leu Ile
625                 630                 635                 640

Gln Gln Arg Met Asp Gly Ser Leu Asn Phe Asn Arg Thr Trp Gln Asp
                645                 650                 655

Tyr Lys Arg Gly Phe Gly Ser Leu Asn Asp Glu Gly Glu Gly Glu Phe
                660                 665                 670

Trp Leu Gly Asn Asp Tyr Leu His Leu Leu Thr Gln Arg Gly Ser Val
                675                 680                 685

Leu Arg Val Glu Leu Glu Asp Trp Ala Gly Asn Glu Ala Tyr Ala Glu
                690                 695                 700

Tyr His Phe Arg Val Gly Ser Glu Ala Glu Gly Tyr Ala Leu Gln Val
705                 710                 715                 720

Ser Ser Tyr Glu Gly Thr Ala Gly Asp Ala Leu Ile Glu Gly Ser Val
                725                 730                 735

Glu Glu Gly Ala Glu Tyr Thr Ser His Asn Asn Met Gln Phe Ser Thr
                740                 745                 750

Phe Asp Arg Asp Ala Asp Gln Trp Glu Glu Asn Cys Ala Glu Val Tyr
                755                 760                 765

Gly Gly Gly Trp Trp Tyr Asn Asn Cys Gln Ala Ala Asn Leu Asn Gly
                770                 775                 780

Ile Tyr Tyr Pro Gly Gly Ser Tyr Asp Pro Arg Asn Asn Ser Pro Tyr
785                 790                 795                 800

Glu Ile Glu Asn Gly Val Val Trp Val Ser Phe Arg Gly Ala Asp Tyr
                805                 810                 815

Ser Leu Arg Ala Val Arg Met Lys Ile Arg Pro Leu Val Thr Gln
                820                 825                 830
```

<210> SEQ ID NO 24
<211> LENGTH: 23
<212> TYPE: PRT
<213> ORGANISM: Homo sapiens

<400> SEQUENCE: 24

Ser Ser Ser Tyr Ser Lys Gln Phe Thr Ser Thr Ser Tyr Asn Arg
1               5                   10                  15

Gly Asp Ser Thr Phe Glu Ser
            20

<210> SEQ ID NO 25
<211> LENGTH: 609
<212> TYPE: PRT
<213> ORGANISM: Homo sapiens

<400> SEQUENCE: 25

Gly Pro Arg Val Val Glu Arg His Gln Ser Ala Cys Lys Asp Ser Asp
1               5                   10                  15

Trp Pro Phe Cys Ser Asp Glu Asp Trp Asn Tyr Lys Cys Pro Ser Gly
            20                  25                  30

Cys Arg Met Lys Gly Leu Ile Asp Glu Val Asn Gln Asp Phe Thr Asn
        35                  40                  45

Arg Ile Asn Lys Leu Lys Asn Ser Leu Phe Glu Tyr Gln Lys Asn Asn
    50                  55                  60

Lys Asp Ser His Ser Leu Thr Thr Asn Ile Met Glu Ile Leu Arg Gly
65                  70                  75                  80

Asp Phe Ser Ser Ala Asn Asn Arg Asp Asn Thr Tyr Asn Arg Val Ser
                85                  90                  95

Glu Asp Leu Arg Ser Arg Ile Glu Val Leu Lys Arg Lys Val Ile Glu
            100                 105                 110

Lys Val Gln His Ile Gln Leu Leu Gln Lys Asn Val Arg Ala Gln Leu
        115                 120                 125

Val Asp Met Lys Arg Leu Glu Val Asp Ile Asp Ile Lys Ile Arg Ser
    130                 135                 140

Cys Arg Gly Ser Cys Ser Arg Ala Leu Ala Arg Glu Val Asp Leu Lys
145                 150                 155                 160

Asp Tyr Glu Asp Gln Gln Lys Gln Leu Glu Gln Val Ile Ala Lys Asp
                165                 170                 175

Leu Leu Pro Ser Arg Asp Arg Gln His Leu Pro Leu Ile Lys Met Lys
            180                 185                 190

Pro Val Pro Asp Leu Val Pro Gly Asn Phe Lys Ser Gln Leu Gln Lys
        195                 200                 205

Val Pro Pro Glu Trp Lys Ala Leu Thr Asp Met Pro Gln Met Arg Met
    210                 215                 220

Glu Leu Glu Arg Pro Gly Gly Asn Glu Ile Thr Arg Gly Gly Ser Thr
225                 230                 235                 240

Ser Tyr Gly Thr Gly Ser Glu Thr Glu Ser Pro Arg Asn Pro Ser Ser
                245                 250                 255

Ala Gly Ser Trp Asn Ser Gly Ser Ser Gly Pro Gly Ser Thr Gly Asn
            260                 265                 270

Arg Asn Pro Gly Ser Ser Gly Thr Gly Gly Thr Ala Thr Trp Lys Pro
        275                 280                 285

Gly Ser Ser Gly Pro Gly Ser Thr Gly Ser Trp Asn Ser Gly Ser Ser
    290                 295                 300

Gly Thr Gly Ser Thr Gly Asn Gln Asn Pro Gly Ser Pro Arg Pro Gly
305                 310                 315                 320

Ser Thr Gly Thr Trp Asn Pro Gly Ser Ser Glu Arg Gly Ser Ala Gly
            325                 330                 335

His Trp Thr Ser Glu Ser Ser Val Ser Gly Ser Thr Gly Gln Trp His
            340                 345                 350

Ser Glu Ser Gly Ser Phe Arg Pro Asp Ser Pro Gly Ser Gly Asn Ala
            355                 360                 365

Arg Pro Asn Asn Pro Asp Trp Gly Thr Phe Glu Glu Val Ser Gly Asn
370                 375                 380

Val Ser Pro Gly Thr Arg Arg Glu Tyr His Thr Glu Lys Leu Val Thr
385                 390                 395                 400

Ser Lys Gly Asp Lys Glu Leu Arg Thr Gly Lys Glu Lys Val Thr Ser
            405                 410                 415

Gly Ser Thr Thr Thr Arg Arg Ser Cys Ser Lys Thr Val Thr Lys
            420                 425                 430

Thr Val Ile Gly Pro Asp Gly His Lys Glu Val Thr Lys Glu Val Val
            435                 440                 445

Thr Ser Glu Asp Gly Ser Asp Cys Pro Glu Ala Met Asp Leu Gly Thr
450                 455                 460

Leu Ser Gly Ile Gly Thr Leu Asp Gly Phe Arg His Arg His Pro Asp
465                 470                 475                 480

Glu Ala Ala Phe Phe Asp Thr Ala Ser Thr Gly Lys Thr Phe Pro Gly
            485                 490                 495

Phe Phe Ser Pro Met Leu Gly Glu Phe Val Ser Glu Thr Glu Ser Arg
            500                 505                 510

Gly Ser Glu Ser Gly Ile Phe Thr Asn Thr Lys Glu Ser Ser Ser His
            515                 520                 525

His Pro Gly Ile Ala Glu Phe Pro Ser Arg Gly Lys Ser Ser Ser Tyr
            530                 535                 540

Ser Lys Gln Phe Thr Ser Ser Thr Ser Tyr Asn Arg Gly Asp Ser Thr
545                 550                 555                 560

Phe Glu Ser Lys Ser Tyr Lys Met Ala Asp Gly Ala Gly Ser Glu Ala
            565                 570                 575

Asp His Glu Gly Thr His Ser Thr Lys Arg Gly His Ala Lys Ser Arg
            580                 585                 590

Pro Val Arg Gly Ile His Thr Ser Pro Leu Gly Lys Pro Ser Leu Ser
            595                 600                 605

Pro

<210> SEQ ID NO 26
<211> LENGTH: 25
<212> TYPE: PRT
<213> ORGANISM: Homo sapiens

<400> SEQUENCE: 26

Ser Ser Ser Tyr Ser Lys Gln Phe Thr Ser Ser Thr Ser Tyr Asn Arg
1               5                   10                  15

Gly Asp Ser Thr Phe Glu Ser Lys Ser
            20                  25

<210> SEQ ID NO 27
<211> LENGTH: 26
<212> TYPE: PRT
<213> ORGANISM: Homo sapiens -continued

```
<400> SEQUENCE: 27

Ser Ser Ser Tyr Ser Lys Gln Phe Thr Ser Thr Ser Tyr Asn Arg
1               5                   10                  15

Gly Asp Ser Thr Phe Glu Ser Lys Ser Tyr
            20              25
```

BIOMARKERS FOR COGNITIVE IMPAIRMENT AND METHODS FOR DETECTING COGNITIVE IMPAIRMENT USING SUCH BIOMARKERS

CROSS-REFERENCE TO RELATED APPLICATIONS

This application is a Continuation of application Ser. No. 15/639,735, filed on Jun. 30, 2017, which is a Continuation of application Ser. No. 15/467,646, filed on Mar. 23, 2017 (now abandoned), which is a Continuation of application Ser. No. 14/582,778, filed on Dec. 24, 2014 (now abandoned), which is a Continuation of application Ser. No. 13/995,682, filed on Sep. 3, 2013 (now abandoned), which was filed as PCT International Application No. PCT/JP2011/007150 on Dec. 21, 2011, which claims the benefit under 35 U.S.C. § 119(a) to Patent Application No. 2010-285726, filed in Japan on Dec. 22, 2010, all of which are hereby expressly incorporated by reference into the present application.

FIELD OF THE INVENTION

The present invention relates to novel biomarkers for mild cognitive impairment or cognitive impairment including Alzheimer disease, and methods for detecting cognitive impairment using such biomarkers.

BACKGROUND OF THE INVENTION

The commonly used means to differentiate between normal and non-normal states of a human subject using his or her biological materials are mainly those which have been used in the field of diagnostics. Most frequently used are those methods which target biomarkers in blood. It has been practiced in this field to comparatively measure the amount of a specific protein or a peptide that is less than 10,000 in molecular weight or, in the case of enzyme protein, enzyme activities in samples from normal (healthy) subjects and those from diseased individuals to help diagnosis. Here, prior to testing real samples, measurements are done on a fixed number each of samples from healthy controls and patients with certain disease with respect to the amount (s) or activity (activities) of single or multiple specific proteins or peptides and the ranges of abnormal and normal values are respectively determined. The sample to be evaluated is then analyzed by the same method and the resultant value is judged with respect to whether it is in normal or abnormal range.

In the actual measurements, the amount(s) of specified protein(s) or peptide(s) in test samples, as such or after dilution, are determined by the use of enzyme-linked immunosorbent assay (ELISA) which uses a primary, or secondary, antibody labeled with an enzyme reacting with a substrate that yields a color upon reaction, chemiluminescent immunoassay (CLIA), radioimmunoassay (RIA) which uses a primary, or secondary, antibody labeled with a radioisotope, and, if the protein is an enzyme, the measurement of the activity of the enzyme by adding its substrate and determining the intensity of produced color, etc. These antibody-based methods are called as enzyme-, fluorescence- or radioisotope-labeled methods, respectively. In addition, there is a method where an enzyme reaction product derived from the corresponding substrate is determined by high performance liquid chromatography (HPLC). In further addition, there is a method where HPLC is combined with mass spectrometer, called LC-MS/MS, and there is a method called selected reaction monitoring (SRM)/multiple reaction monitoring (MRM) that utilizes LC-MS/MS. In another method to determine the concentration in a sample, it is appropriately pretreated, and separation of proteins or peptides is attained by 2-dimensional polyacrylamide gel electrophoresis (2D-PAGE), and target protein or peptide is determined by silver staining, Coomassie blue staining or immunological staining (Western blotting) that uses an antibody to target protein or peptide. In still further addition, there is a method which utilizes mass spectrometry to determine the amount of target protein or peptide in samples fractionated by column chromatography. Instead of column chromatography, protein chips and magnetic beads may also be utilized for purpose of pretreatment.

Furthermore, these inventors have developed an immunoMS method, where target protein or peptide is captured by beads (including magnetic ones) with linked antibody to the protein or peptide, eluted from the beads, and determined by mass spectrometry. Further, intact proteins have been reported to be analyzed by mass spectrometry using above-mentioned methods after digestion with trypsin etc. (Patent Document 1). Here, intact target proteins are selected either by fractionation or by adsorption to an adsorbant specific to them and then determined by mass spectrometry.

Number of patients suffered from cognitive impairment like Alzheimer disease is increasing rapidly along with increasing of old-age population in Japan. It is estimated that number of patients is 1.3 million in 1995 and it will be 1.9 million in 2005 and will reach to about 3.0 million in 2020. It is reported that 60-90% of cognitive impairment is Alzheimer disease. As manifestation of Alzheimer disease is not only loss of memory but several disturbance in daily life, increase of patients of this disease is becoming an important social issue to be solved. In Japan, Donepezil-hydrochloride, anti-acetylcholine esterase inhibitor has been available for medical treatment for Alzheimer disease since 1999, and it let progress of cognitive impairment in these patients be 'slow-down' efficiently, if the patient is diagnosed at early stage. Thus, in medication of Alzheimer disease, most important issue is 'early diagnosis' to treat the patients effectively by drug available at present and new coining drug.

Followings are major criteria for diagnosis of Alzheimer disease described in DSM-IV, which is published by American Psychiatric Association.

A. The development of multiple cognitive deficits manifested by both
  (1) memory impairment (impaired ability to learn new information or to recall previously learned information)
  (2) one of the following cognitive disturbances:
    a) aphasia (language disturbance)
    b) apraxia (impaired ability to carry out motor activities despite intact motor function)
    c) agnosia (failure to recognize or identify objects despite intact sensory function)
    d) disturbance in executive functioning (i.e., planning, organizing, sequencing, abstracting)
B. The cognitive deficits in Criteria A 1 and A2 each cause significant impairment in social or occupational functioning and represent a significant decline from a previous level of functioning. (Non-patent reference 1)

There are several types of neurological disorders related to Alzheimer disease (AD). As cognitive dysfunction appears gradually in dementia including AD, there is a disease status of pre-stage of dementia. This stage is called as mild cognitive impairment (MCI). In United States, 10% MCI develops to AD within 1 year, and 50% of MCI develops to AD within 4 years. MCI is defined as a condition characterized by newly acquired cognitive decline to an extent that is beyond that expected for age or educational background, yet not causing significant functional impairment, and not showing disturbance in daily life. Frontotemporal dementia (frontotemporal lobar degeneration) (FTD) shows loss of personal awareness, loss of social awareness, hyperorality, and stereotyped, perseverative behavior. These clinical characteristics are different from AD. FTD includes Pick's disease, which is characterized by microscopically Pick bodies usually found in limbic, paralimbic, and ventral temporal lobe cortex. Dementia with Lewy bodies (DLB) is characterized by progressive disease and psychiatric symptoms include anxiety, depression, hallucinations (usually visual) and delusions (false beliefs). DLB is thought to be the second most common subtype and 10-30% of dementia is DLB. The symptoms of DLB are caused by the build-up of Lewy bodies. FTD and DLB belong to demented neurological disease as they also lose of memory, their ability to solve problems and maintain emotional control. (Non-patent reference 1)

In description in present patent, cognitive impairment includes AD, MCI and the demented neurological disease.

The screening tests for dementia widely used are the Hasegawa Dementia Scale-revised (HDS-R) and Mini-Mental State Examination (MMSE). In these screening tests, inspector asks several questions and evaluates level of cognitive impairment of each subject by scores. HDS-R is revised version of HDS published in 1991, in HDS-R, test consists of 9 questions to analyses orientation, remembrance, calculation, retain and recall ability, and common sense. Full score is 30 and a person whose score is less than 23 is suspected as dementia. MMSE has been developed in United States to screen and diagnose dementia, and analyses global cognitive function, with items assessing orientation, word recall, attention and calculation, language abilities, and visuospatial (drawing) ability. This test consists of 11 questions, and full score is 30 and a person who has score less than 23 is suspected as dementia. The results of HDS-R and MMSE coincide with each other. Both are used for screening, not for diagnosis and not for staging of disease progression. (Non-patent reference 1)

Neuroimaging test for dementia are Computed tomography (CT) and Magnetic resonance imaging (MRI) which evaluate morphological changes like brain atrophy and ventricular dilation and single-photon emission computed tomography (SPECT) which analyses regional cerebral blood flow and PET which shows brain metabolism by measurement of consumption of oxygen and sugar. SPECT and PET, nuclear imaging technologies, can identify neuronal dysfunction at preclinical stage. However, these neuroimaging cannot be widely used in hospitals because they need special facilities to perform nuclear imaging, and neuroimaging may not be objective test as imaging diagnosis is completely depend on the skill of physician who analyses the mages.

Thus, methods for screening and diagnosis of dementia including AD that are available at present is dependent on tests lacking objectivity and is dependent on expensive instruments, and so it is very difficult to use these tests for screening of early stage-cognitive impairment. If we get blood (serum/plasma) biomarker for cognitive impairment which enables us objective test using specimens we can easily obtain, we can identify cognitive impairment at early stage (preclinical stage) by blood test using such biomarker. Present patent provides novel biomarkers and a novel and potent diagnostic method for cognitive impairment by using such biomarkers and biomarkers described here.

CITATION LIST

Patent Document

Patent Document 1. JP-A-2004-333274
Patent Document 2, JP-A-2006-308533

Non-Patent Document

Non-Patent Document 1, "The better understanding of Alzheimer's disease.," edited by Imaharu Nakano and HIdehiro Mizusawa., Nagai Shoten Co., Ltd., 2004 (in Japanese)
Non-Patent Document 2, Benkirane, N. et al., J. Biol. Chem. Vol. 268, 26279-26285, 1993

SUMMARY OF THE INVENTION

Technical Problem

The present invention aims to present methods to detect mild cognitive impairment or cognitive impairment including Alzheimer disease by using a protein or its partial peptide that differs in presence or absence, or in quantity between non-cognitive impairment subjects (including healthy people, the human subjects that may be affected with any disease and unaffected with psychiatry disease including cognitive impairment. These human subjects are allowed to match the age and gender of patient with cognitive impairment. And, these human subjects are called non-demented control, hereinafter abbreviated to NDC.) and patients with cognitive impairment and further aims to present biomarkers comprising said proteins and said partial peptides to be used to detect mild cognitive impairment or cognitive impairment including Alzheimer disease.

Solution to Problem

These inventors investigated to find out means to detect cognitive impairment and found a peptide capable of detecting mild cognitive impairment or cognitive impairment including Alzheimer disease in the serum. Said peptides found in the present invention are those with significance as a biomarker to detecting in the case of serum not only other biological materials such as blood, plasma, cerebrospinal fluid, and urine. Simultaneously, protein or peptide is the origin of these peptides (hereinafter referred to as intact proteins or peptides) also has significance as biomarkers.

Specifically, these inventors found that a biomarker comprising at least one protein or peptide selected from the group consisting of Complement C3 consisting of amino acid sequence expressed by SEQ ID NO: 1, Transcription factor AP-2 gamma consisting of amino acid sequence expressed by SEQ ID NO: 3, Synapsin-3 consisting of amino acid sequence expressed by SEQ ID NC): 5, Oxytocin receptor consisting of amino acid sequence expressed by SEQ ID NO: 7, Inter-alpha-trypsin inhibitor heavy chain H5-like protein consisting of amino acid sequence expressed by SEQ ID NO: 9, E3 ubiquitin-protein ligase HERC2 consisting of amino acid sequence expressed by SEQ ID NO: 11, Prothrombin consisting of amino acid sequence expressed by SEQ ID NO: 13. Transthyretin consisting of amino acid sequence expressed by SEQ ID NO: 15, Tumor necrosis factor receptor superfamily member 16 consisting of amino acid sequence expressed by SEQ ID NO: 17, Complement C4-A consisting of amino acid sequence expressed by SEQ ID NO: 19, Complement C4-B consisting of amino acid sequence expressed by SEQ ID NO: 21, Fibrinogen alpha chain (isoform 1) consisting of amino acid sequence expressed by—SEQ ID NO: 23, and Fibrinogen alpha chain (isoform 2) consisting of amino acid sequence expressed by SEQ ID NO: 25; or a biomarker comprising protein fragment or peptide of not less than 5 amino acid residues arising from at least one protein or peptide selected from the group consisting of them, could be used as biomarkers to detect cognitive impairment.

Furthermore, these inventors found that a biomarker comprising from the group consisting of Complement C3-derived peptide CO3 consisting of amino acid sequence expressed by SEQ ID NO: 2, Transcription factor AP-2 gamma-derived peptide AP2C consisting of amino acid sequence expressed by SEQ ID NO: 4, Synapsin-3-derived peptide SYN3 consisting of amino acid sequence expressed by SEQ ID NO: 6, Oxytocin receptor-derived peptide OXYR consisting of amino acid sequence expressed by SEQ ID NO: 8, Inter-alpha-trypsin inhibitor heavy chain H5-like protein-derived peptide ITH5L consisting of amino acid sequence expressed by SEQ ID NO: 10, E3 ubiquitin-protein ligase HERC2-derived peptide HERC2 consisting of amino acid sequence expressed by SEQ NO: 12, Prothrombin-derived peptide THRB consisting of amino acid sequence expressed by SEQ ID NO: 14, Transthyretin-derived peptide TTHY consisting of amino acid sequence expressed by SEQ ID NO: 16, Tumor necrosis factor receptor superfamily; member 16-derived peptide TNR16 consisting of amino acid sequence expressed by SEQ ID NO: 18, Complement C4-derived peptide CO4-1 consisting of amino acid sequence expressed by SEQ ID NO: 20, Complement C4-derived peptide CO4-2 consisting of amino acid sequence expressed by SEQ ID NO: 22. Fibrinogen alpha chain-derived peptide FIBA-1 consisting of amino acid sequence expressed by SEQ ID NO: 24, Fibrinogen alpha chain-derived peptide FIBA-2 consisting of amino acid sequence expressed by SEQ ID NO: 26, and Fibrinogen alpha chain-derived peptide FIBA-3 consisting of amino acid sequence expressed by SEQ ID NO: 27 could be used as biomarkers to detect cognitive impairment.

These inventors brought the present invention to perfection by further succeeding in determining simultaneously these many proteins and its partial peptides by using two-dimensional high performance liquid chromatography-MALDI TOF-MS method (mass spectrometry) and immunoMS method.

The features of the present invention are shown below.

[1] A biomarker for detection of cognitive impairment comprising protein fragment or peptide of not less than 5 amino acid residues arising from at least one protein or peptide selected from the group consisting of Complement C3 consisting of amino acid sequence expressed by SEQ ID NO: 1, Transcription factor AP-2 gamma consisting of amino acid sequence expressed by SEQ ID NO: 3, Synapsin-3 consisting of amino acid sequence expressed by SEQ ID NO: 5, Oxytocin receptor consisting of amino acid sequence expressed by SEQ ID NO: 7, Inter-alpha-trypsin inhibitor heavy chain H5-like protein consisting of amino acid sequence expressed by SEQ ID NO: 9, E3 ubiquitin-protein ligase HERC2 consisting of amino acid sequence expressed by SEQ ID NO: 11, Prothrombin consisting of amino acid sequence expressed by SEQ ID NC): 13, Transthyretin consisting of amino acid sequence expressed by SEQ ID NO: 15. Tumor necrosis factor receptor superfamily member 16 consisting of amino acid sequence expressed by SEQ ID NO: 17, Complement C4-A consisting of amino acid sequence expressed by SEQ ID NO: 19, Complement C4-B consisting of amino acid sequence expressed by SEQ II) NO: 21, Fibrinogen alpha chain (isoform 1) consisting of amino acid sequence expressed by SEQ ID NO: 23, and Fibrinogen alpha chain (isoform 2) consisting of amino acid sequence expressed by SEQ ID NO: 25, or a biomarker for detection of cognitive impairment comprising at least one protein or peptide selected from the group consisting of them.

[2] A biomarker for detection of cognitive impairment comprising the peptide selected from the group consisting of Complement C3-derived peptide CO3 consisting of amino acid sequence expressed by SEQ ID NO: 2, Transcription factor AP-2 gamma-derived peptide AP2C consisting of amino acid sequence expressed by SEQ ID NO: 4, Synapsin-3-derived peptide SYN3 consisting of amino acid sequence expressed by-SEQ ID NO: 6, Oxytocin receptor-derived peptide OXYR consisting of amino acid sequence expressed by SEQ ID NO: 8, Inter-alpha-trypsin inhibitor heavy chain H5-like protein-derived peptide ITH5L consisting of amino acid sequence expressed by SEQ ID NO: 10, E3 ubiquitin-protein ligase HERC2-derived peptide HERC2 consisting of amino acid sequence expressed by SEQ ID NO: 12, Pro-thrombin-derived peptide THRB consisting of amino acid sequence expressed by SEQ ID NO: 14, Transthyretin-derived peptide TTHY consisting of amino acid sequence expressed by SEQ ID NO: 16, Tumor necrosis factor receptor superfamily member 16-derived peptide TNR16 consisting of amino acid sequence expressed by SEQ ID NO: 18, Complement C4-derived peptide CO4-1 consisting of amino acid sequence expressed by SEQ ID NO: 20, Complement C4-derived peptide CO4-2 consisting of amino acid sequence expressed by SEQ ID NO: 22, Fibrinogen alpha chain-derived peptide FIBA-1 consisting of amino acid sequence expressed by SEQ ID NO: 24, Fibrinogen alpha chain-derived peptide FIBA-2 consisting of amino acid sequence expressed by SEQ ID NO: 26, and Fibrinogen alpha chain-derived peptide FIBA-3 consisting of amino acid sequence expressed by SEQ ID NO: 27, or a biomarker for detection of cognitive impairment comprising at least one protein or peptide selected from the group consisting of them.

[3] A biomarker of cognitive impairment comprising the peptides selected from the group consisting of amino acid sequence expressed by SEQ ID NOS: 2, 4, 6, 8, 10, 12, 14, 16, 18, 20, 22, 24, 26, and 27 that is appeared or increased in biological material of patients of cognitive impairment as compared to biological material of subjects not suffering from psychiatry disease.

[4] A biomarker of Alzheimer disease comprising the peptides selected from the group consisting of amino acid sequence expressed by SEQ ID NOS: 2, 4, 6, 8, 10, 12, 14, 16, 18, 20, 22, 24, 26, and 27 that is appeared or increased in biological material of patients of Alzheimer disease as compared to biological material of subjects not suffering from psychiatry disease.

[5] A biomarker of mild cognitive impairment comprising the peptides selected from the group consisting of amino acid sequence expressed by SEQ NOS: 2, 4, 6, 8, 10, 12, 14, 16, 18, 20, 22, 24, 26, and 27 that is appeared or increased in biological material of patients of mild cognitive impairment as compared to biological material of subjects not suffering from psychiatry disease.

[6] Method for detection of cognitive impairment involving determination in biological material of at least one biomarker for cognitive impairment described in any of [1] to [5].

[7] Method for detection of psychiatry disease described in [6] wherein detection is made either by immunoblot procedure, Western blotting, enzyme-, fluorescence-, or radioisotope-labeled antibody method, mass spectrometry, immunoMS method or surface plasmon resonance method.

[8] A kit for detection of cognitive impairment to determine at least one biomarker described in any of [1] to [5].

[9] A kit for detection of psychiatry disease containing antibody or aptamer to at least one biomarker described in any of [1] to [5].

Advantageous Effect of the Invention

According to the present invention, it is possible to diagnose the subject such as suffering from mild cognitive impairment or cognitive impairment including Alzheimer's disease, when to increase or appear compared to the biological sample of subjects not suffering from psychiatry disease by determining amount of at least one biomarker comprising protein fragment or peptide of not less than 5 amino acid residues arising from at least one protein or peptide selected from the group consisting of Complement C3 consisting of amino acid sequence expressed by SEQ ID NO: 1, Transcription factor AP-2 gamma consisting of amino acid sequence expressed by SEQ ID NO: 3, Synapsin-3 consisting of amino acid sequence expressed by SEQ ID NO: 5, Oxytocin receptor consisting of amino acid sequence expressed by SEQ ID NO: 7, Inter-alpha-trypsin inhibitor heavy chain H5-like protein consisting of amino acid sequence expressed by SEQ ID NO: 9, E3 ubiquitin-protein ligase HERC2 consisting of amino acid sequence expressed by SEQ ID NO: 11, Prothrombin consisting of amino acid sequence expressed by SEQ ID NO: 13, Transthyretin consisting of amino acid sequence expressed by SEQ ID NO: 15, Tumor necrosis factor receptor superfamily member 16 consisting of amino acid sequence expressed by SEQ ID NO: 17, Complement C4-A consisting of amino acid sequence expressed by SEQ ID NO: 19, Complement C4-B consisting of amino acid sequence expressed by SEQ ID NO: 21, Fibrinogen alpha chain (isoform 1) consisting of amino acid sequence expressed by SEQ ID NO: 23, and Fibrinogen alpha chain (isoform 2) consisting of amino acid sequence expressed by SEQ ID NO: 25.

In addition, according to the present invention, it is possible to diagnose the subject such as suffering from mild cognitive impairment or cognitive impairment including Alzheimer's disease, when to increase or appear compared to the biological sample of subjects not suffering from psychiatry disease by determining kind or amount at least one peptide selected from the group consisting of Complement C3-derived peptide CO3 consisting of amino acid sequence expressed by SEQ ID NO: 2, Transcription factor AP-2 gamma-derived peptide AP2C consisting of amino acid sequence expressed by SEQ ID NO: 4, Synapsin-3-derived peptide SYN3 consisting of amino acid sequence expressed by SEQ ID NO: 6, Oxytocin receptor-derived peptide OXYR consisting of amino acid sequence expressed by SEQ ID NO: 8, Inter-alpha-trypsin inhibitor heavy chain H5-like protein-derived peptide ITH5L consisting of amino acid sequence expressed by SEQ ID NO: 10, E3 ubiquitin-protein ligase HERC2-derived peptide HERC2 consisting of amino acid sequence expressed by SEQ ID NO: 12, Prothrombin-derived peptide THRB consisting of amino acid sequence expressed by SEQ ID NO: 14, Transthyretin-derived peptide TTHY consisting of amino acid sequence expressed by SEQ ID NO: 16, Tumor necrosis factor receptor superfamily member 16-derived peptide TNR16 consisting of amino acid sequence expressed by SEQ ID NO: 18, Complement C4-derived peptide CO4-1 consisting of amino acid sequence expressed by SEQ ID NO: 20, Complement C4-derived peptide CO4-2 consisting of amino acid sequence expressed by SEQ ID NO: 22, Fibrinogen alpha chain-derived peptide FIBA-1 consisting of amino acid sequence expressed by SEQ ID NO: 24, Fibrinogen alpha chain-derived peptide FIBA-2 consisting of amino acid sequence expressed by SEQ ID NO: 26, and Fibrinogen alpha chain-derived peptide FIBA-3 consisting of amino acid sequence expressed by SEQ ID NO: 27.

The present invention provides a diagnostic system that is high in both accuracy and specificity. The present invention enables highly accurate diagnosis of cognitive impairment in which there have been no specific test methods for such biological materials as blood. Furthermore, the biomarkers disclosed in the present invention are highly useful in judgment of drug efficacy.

BRIEF DESCRIPTION OF DRAWINGS

FIG. 2 shows the comparison between NDC and cognitive impairment (AD, MCI, DLB and FTD) related to CO3.

FIG. 3A) shows the ROC curve of the comparison of AD vs. NDC. FIG. 3B) shows the ROC curve of the comparison of MCI vs. NDC.

In FIG. 4 top, it was shown the amino acid sequence of CO3, and it was shown y-ions and b-ions that appear in the MS/MS spectrum.

DESCRIPTION OF EMBODIMENTS

Figure 1:
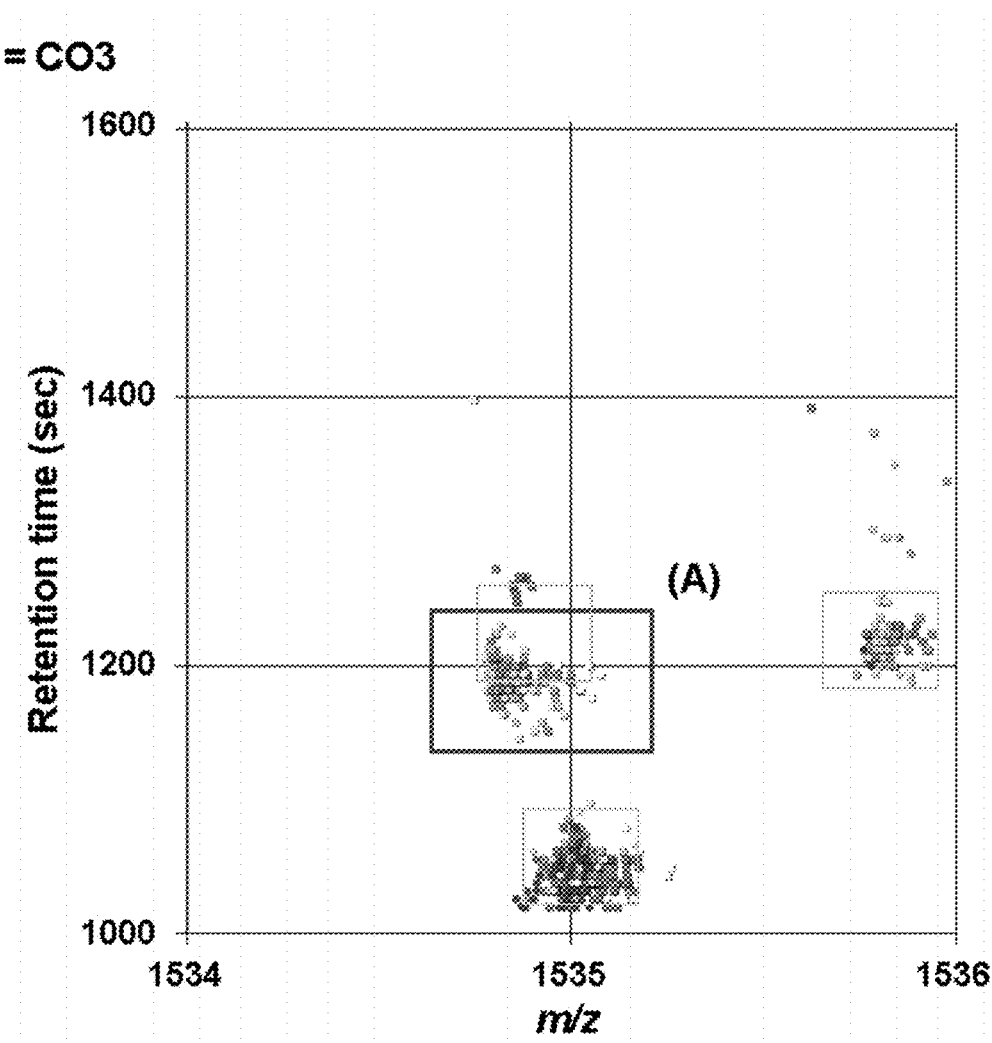
FIG. 1 illustrates the cluster map of Marker A. The dots within the rectangle indicated by (A) are m/z and retention time of the mass peak of Marker A detected from the serum of the individual subject using reverse phase chromatography. The dots in a cluster can be regarded as the same retention time and the same m/z in the error range, and the dots in a cluster are defined to be derived from the same peptide.

The present invention is a method for determining the kind and the amount of intact protein and/or its partial peptide when test subject is suffering from cognitive impairment as well as for diagnosing whether test subject is suffering from cognitive impairment. A peptide is generally said to be a chemical entity, made by polymerizing a number of amino acids, of less than 10,000 in molecular weight or by polymerizing several to less than about 50 amino acid residues. While in the present invention a partial peptide of an intact protein can be used as a biomarker for detection of cognitive impairment, such partial peptide is defined as a peptide of less than 10,000 in molecular weight consisting of a part of the amino acid sequence of the intact protein. Such peptide may arise as a partial peptide during the expression by transcription followed by synthesis by translation before maturing into an intact protein or as a peptide produced by enzyme digestion in the body after the intact protein has been synthesized. It is possible that, when the body is in abnormal state suffering from such disease as cognitive impairment, the mechanism for protein synthesis and regulation is de-regulated. In other words, the present invention is also a method for determining if test subject is in normal state or is suffering from cognitive impairment by using the degree of protein synthesis and/or protein digestion as an indicator. The detection of cognitive impairment in the present invention means evaluation and differentiation, i.e., diagnosis of test subject as to whether the subject is suffering from cognitive impairment. The present invention can also include the evaluation of patient's risk of suffering from more serious cognitive impairment.

Specifically, in the method of the present invention, the examples of intact protein that can be used as a cognitive impairment include Complement C3 consisting of amino acid sequence expressed by SEQ ID NO: 1, Transcription factor AP-2 gamma consisting of amino acid sequence expressed by SEQ ID NO: 3, Synapsin-3 consisting of amino acid sequence expressed by SEQ ID NO: 5, Oxytocin receptor consisting of amino acid sequence expressed by SEQ ID NO: 7, Inter-alpha-trypsin inhibitor heavy chain H5-like protein consisting of amino acid sequence expressed by SEQ ID NO: 9, E3 ubiquitin-protein ligase HERC2 consisting of amino acid sequence expressed by SEQ ID NO: 11, Prothrombin consisting of amino acid sequence expressed by SEQ ID NO: 13, Transthyretin consisting of amino acid sequence expressed by SEQ ID NO: 15, Tumor necrosis factor receptor superfamily member 16 consisting of amino acid sequence expressed by SEQ ID NO: 17, Complement C4-A consisting of amino acid sequence expressed by SEQ ID NO: 19, Complement C4-B consisting of amino acid sequence expressed by SEQ ID NO: 21, Fibrinogen alpha chain (isoform 1) consisting of amino acid sequence expressed by SEQ ID NO: 23, and Fibrinogen alpha chain (isoform 2) consisting of amino acid sequence expressed by SEQ ID NO: 25, and further, the peptide fragments that comprise of partial peptides of not less than 5 amino acid residues of these intact proteins can be used as same purpose.

Still further, an example of biomarkers for cognitive impairment of the present invention includes the partial peptides consisting of amino acid sequence expressed by SEQ ID NO: 2 of Complement C3-derived peptide CO3, SEQ ID NO: 4 of Transcription factor AP-2 gamma-derived peptide AP2C, SEQ ID NO: 6 of Synapsin-3-derived peptide SYN3, SEQ NO: 8 of Oxytocin receptor-derived peptide OXYR, SEQ ID NO: 10 of Inter-alpha-trypsin inhibitor heavy chain H5-like protein-derived peptide ITH5L, SEQ ID NO: 12 of E3 ubiquitin-protein ligase HERC2-derived peptide HERC2, SEQ ID NO: 14 of Prothrombin-derived peptide THRB, SEQ ID NO: 16 of Transthyretin-derived peptide TTHY, SEQ ID NO: 18 of Tumor necrosis factor receptor superfamily member 16-derived peptide TNR16, SEQ ID NO: 20 of Complement C4-derived peptide CO4-1, SEQ ID NO: 22 of Complement C4-derived peptide CO4-2, SEQ ID NO: 24 of Fibrinogen alpha chain-derived peptide FIBA-1, SEQ ID NO: 26 of Fibrinogen alpha chain-derived peptide FIBA-2, and SEQ ID NO: 27 of Fibrinogen alpha chain-derived peptide FIBA-3. In the present invention, proteins and peptides consisting of amino acid sequences derived from SEQ ID NOS: 1 through 27 by deletion, exchange, and/or addition of one or a few amino acids can be used as biomarkers and are included in the present invention. "One or a few" herein means "one or three," "one or two," or "one." Furthermore, the partial peptides that can be used as biomarkers in the present invention include those peptide fragments consisting of not less than 5 amino acid residues arising respectively from SEQ ID NOS: 1 through 27. The basis for the limitation of peptide fragments consisting of not less than 5 amino acid residues is in the description below in Non-patent Document 2. The document reported that an antibody obtained by using the peptide IRGERA as immunogen, which was the C-terminus (130-135) of histone H3, recognized the peptide IKGERA derived by exchange of K for R and the peptide CGGGERA which was derived by deletion of IR followed by addition of CGG. This demonstrates that the immunogenicity (antigenicity) is recognized by a peptide of not less than 4 amino acid residues. In order to expand this finding to other peptides than the C-terminus of histone H3, the number of amino acid residue is defined as not less than 5 instead of 4 in the present invention. To make such a low molecular weight peptide as the subject of the present invention is important when the method of detection and differentiation uses immunological means including immunoblot, ELISA and immunoMS.

It is to be noted that there are cases where a sugar chain or sugar chains have been added to an intact protein or its partial peptide to form glycated entities. Proteins and partial peptides in glycated form can also be used as biomarkers for detection of cognitive impairment.

It is also to be noted that, in the present invention, biomarker can be quantified or its presence or absence can be determined qualitatively.

Two-dimensional electrophoresis (2-DE) or 2-dimensional chromatography (2-DC) can be used in the present invention to separate biomarkers in biological materials including serum. Known chromatographic methods can be selected from ion-exchange chromatography, reverse-phase chromatography and gel-filtration chromatography. It is also possible to make quantification with the SRM/MRM method in LC-MS/MS technology. Furthermore, the immunoMS method which these inventors have developed, where target protein or peptide is captured by beads (including magnetic ones) with antibody linked to the protein or peptide, eluted from the beads, and determined by mass spectrometry enables convenient determination of presence or absence or the amount of target protein, protein fragment or peptide without the use of 2-DE or chromatography.

It is possible with the use of the method disclosed in the present invention to evaluate at the stage of mild of cognitive dysfunction in test subject and therefore it can be useful in prophylactic medicine. Further, when psychotherapy and/or drug therapy is given to patients with cognitive impairment, it is reflected in the amount of proteins and partial peptides in biological materials such as serum if the progression of the disorder has been inhibited. Therefore, by measuring these proteins and partial peptides, it is possible to evaluate and determine therapeutic effect.

The kind and amount of a protein in biological materials can be determined by various methods. If target protein (including protein fragment and partial peptide) has been characterized and when an antibody (primary antibody) to it has already been obtained, the following methods can be used:

1. Immunoblot

This is one of the simplest methods. Test serum in a fixed amount (about 1 microliter) after stepwise dilution is dropped onto an appropriate membrane such as of nitrocellulose and dried in air. The membrane is treated with a blocking solution containing a protein such as BSA, washed, reacted with primary antibody, and washed. Thereafter, the membrane is reacted with labeled secondary antibody to detect the primary antibody. The membrane is washed and the label is visualized to measure its density.

2. Western Blotting

After separation with one-dimensional or two-dimensional electrophoresis involving isoelectric focusing or SDS-PAGE, proteins are transferred onto such an appropriate membrane as of PVDF and their amounts are determined, as in above-mentioned immunoblot, using primary antibody and labeled secondary antibody.

3. ELISA

Antibody to protein or its partial peptide is fixed to such a plate as a chemically modified microtiter plate. Appropriate amounts of samples after stepwise dilution are applied to the plate and incubated. Proteins and peptides not captured are removed by washing. Next, the plate is incubated with secondary antibody labeled with fluorescent or chemiluminescent substance or enzyme. After addition of respective substrate, fluorescence, chemiluminescence or visible light due to enzyme reaction is measured for evaluation and judgment.

Additional examples of methods are illustrated below (see Patent Document 2) but the invention is not limited by these examples.

4. Methods that Use Microarray (Microchip)

A microarray is a general term for devices where solidified materials with affinity for target substances are arrayed on solid support (plate). In the present invention, antibodies or aptamer to proteins and partial peptides are arrayed. A sample of biological material is placed on the microarray for fixation of target proteins or partial peptides and the microarray is then incubated with secondary antibody labeled with fluorescent or chemiluminescent substance or enzyme. After addition of respective substrate, fluorescence, chemiluminescence or visible light due to enzyme reaction is measured.

5. Mass Spectrometry

In mass spectrometry, for example, antibody to a specified protein or partial peptide is attached to chemically modified microbeads or plate (protein chip). The microbeads could be magnetic beads. There are no requirements for the material of the plate. The antibody to be used could be (1) an antibody which recognizes the full length form of the specified protein only, (2) an antibody which recognizes a partial peptide only, (3) all of antibodies which recognizes both the specified protein and its partial peptide, or a combination of (1) and (2), (1) and (3), or (2) and (3). Samples after stepwise dilution with original solvent or buffer are added to the microbeads or plate carrying antibody or antibodies and incubated. Those proteins and partial peptides not captured are removed by washing. The protein or partial peptide captured by microbeads or plate is eluted, and analyzed by mass spectrometry with MALDI-TOF-MS, SELDI-TOF-MS, etc. Measurements are made with respect to the mass and intensity of the peak due to the protein, protein fragment or partial peptide. Prior to the measurements a fixed amount of substance serving as the internal standard is added to the original biological material and the intensity of its peak is also measured. The concentration of the target in the original biological material can be calculated from the ratio of peak intensity of the target to the peak intensity of the internal standard. This is called immunoMS method. Further, it is possible to make quantification, after the sample is diluted with original solvent or buffer, or after part of proteins are removed, by separation with HPLC followed by mass spectrometry with electrospray ionization (ESI) method. Therein the SRM/MRM method can be utilized for absolute quantification with the use of an isotope-labeled internal standard peptide.

Furthermore, in addition to the above-mentioned methods, it is possible to analyze proteins and partial peptides by using 2-DE, surface plasmon resonance, etc.

The present invention includes the method to detect cognitive impairment from the presence or absence or amount of the above-mentioned biomarker after applying biological material obtained from test subject to 2-DE or surface plasmon resonance.

EXAMPLES

Discovery of a marker peptide for detection of cognitive impairment using two-dimensional liquid chromatography-mass spectrometry (2D-LC-MALDI TOF-MS).
(1) Serum Samples, Followings, the characters before the parenthesis are an abbreviation.

A sera obtained from 40 AD (Alzheimer's disease), 35MCI (mild cognitive impairment), 13 DLB (Dementia with Lewy bodies), 7 FTD (frontotemporal lobar degeneration), and 21 NDC (subjects not suffering from psychiatry disease) were used.
(2) Methods After 475 µl of 0.1% trifluoroacetic acid (TFA) were added in each of 25 µl of sera, samples were boiled for 15 min at 100 degrees. Subsequently, in order to recover peptides of molecular weight of 10,000 or less, ultrafiltration were performed by using YM-10 filter unit (Millipore Corp.). Then the analysis using 2D-LC-MALDI TOF-MS were performed as follows. In other words, recovering samples were fractionated to 382 fractions per sample by using two-dimensional HPLC (SCX cation exchange column at one-dimension and. C18 reverse-phase column at two-dimension). The samples were fractionated into two fractions by SCX cation exchange column, namely, SCX 1 fraction is through fraction, SCX 2 fraction is the fraction that eluted with 100% salt solution. Two fractions that were fractionated by SCX, respectively, were fractionated 191 fractions by C18 reverse phase column chromatography. It was eluted with 6 seconds in one fraction, and the retention times were calculated by multiplying the number of minus 1 from number of eluted fractions to 6 seconds. All fractionated samples were spotted on MALDI target plate (MTP AnchorChip™ 600/384 plate, BRUKER DALTONICS) for MALDI TOF/TOF mass spectrometer (ultraflex TOF/TOF, BRUKER DALTONICS) using a spotting robot (AccuSpot, SHIMADZU) that is connected online, and matrix solution (alpha-cyano-hydroxycinnamic acid, CHCA) were mixed and crystallized. After mounting MALDI target plate into ultraflex TOF/TOF, the mass and the peak area of the mass were measured automatically in reflection mode by irradiating to crystallized sample by laser. Peak area was normalized with 250 fmole of per each well of bradykinin 1-7 fragment that was added into matrix solution in advance. In other words, the area value was calculated dividing the peak area of specific mass in sample by the peak area obtained from bradykinin1-7 fragment. This area value is corresponding in 25 µl of sample serum. Detection of difference in abundance of peptides in serum between groups (called differential analysis) was performed using multi-group statistical analysis software Pamassum™ (MCBI) developed by us. Peptide that was observed to difference in abundance was directly determined amino acid sequence in MS/MS analysis by ultraflex TOF/TOF, and intact proteins or peptides of their origin were identified.
(3) Results The following shows the result of differential analysis by Pamassum software for data of serum individual subjects obtained using 2D-LC MALDI TOP-MS. FIG. 1 shows the result that was obtained from sample that was applied to 2D-LC-MALDI TOF-MS. Sample was fractionated into 2 fractions by SCX cation exchange column in the first dimension, then first fractions from SCX column (SCX 1) were fractionated into 191 fractions by C18 reverse-phase column. Mass spectra of 191 fractions were obtained by MALDI TOF-MS measuring. As the horizontal axis is the m/z and the vertical axis is the fractions of reverse-phase column chromatography, FIG. 1 was visualized by Parnassum software developed by present inventors. The dots in FIG. 1 shows respectively TOF-MS peak derived from the individual subject. The sections that dots are gathered can be regarded as the same retention time and the same m/z in the error range, and the dots in the sections are defined to be derived from the same peptide. These sections are referred to as clusters. Section (A) of FIG. 1 shows cluster of Marker A.

Figure 2:
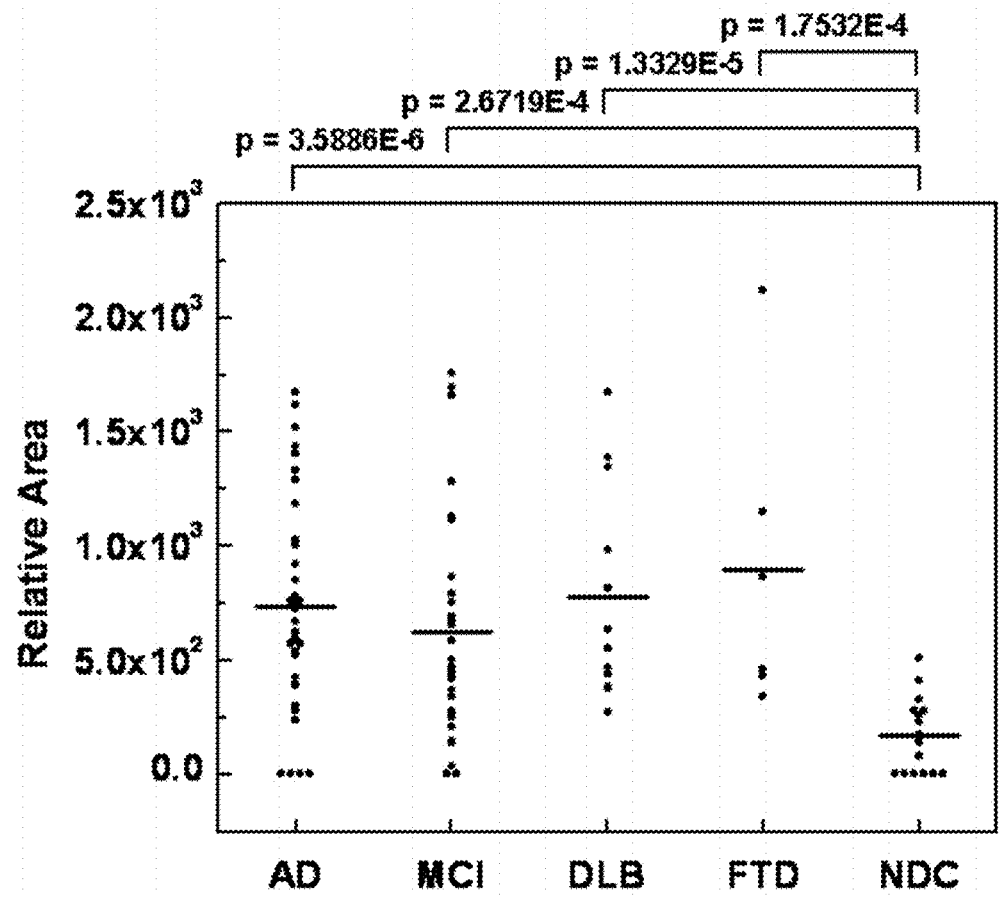
FIG. 2 illustrates the results of differential analysis in the case of Marker A. As shown in the amino acid sequences resulting of MS/MS analysis in FIG. 4, Marker A is Complement C3-derived peptides CO3.
Figure 4:
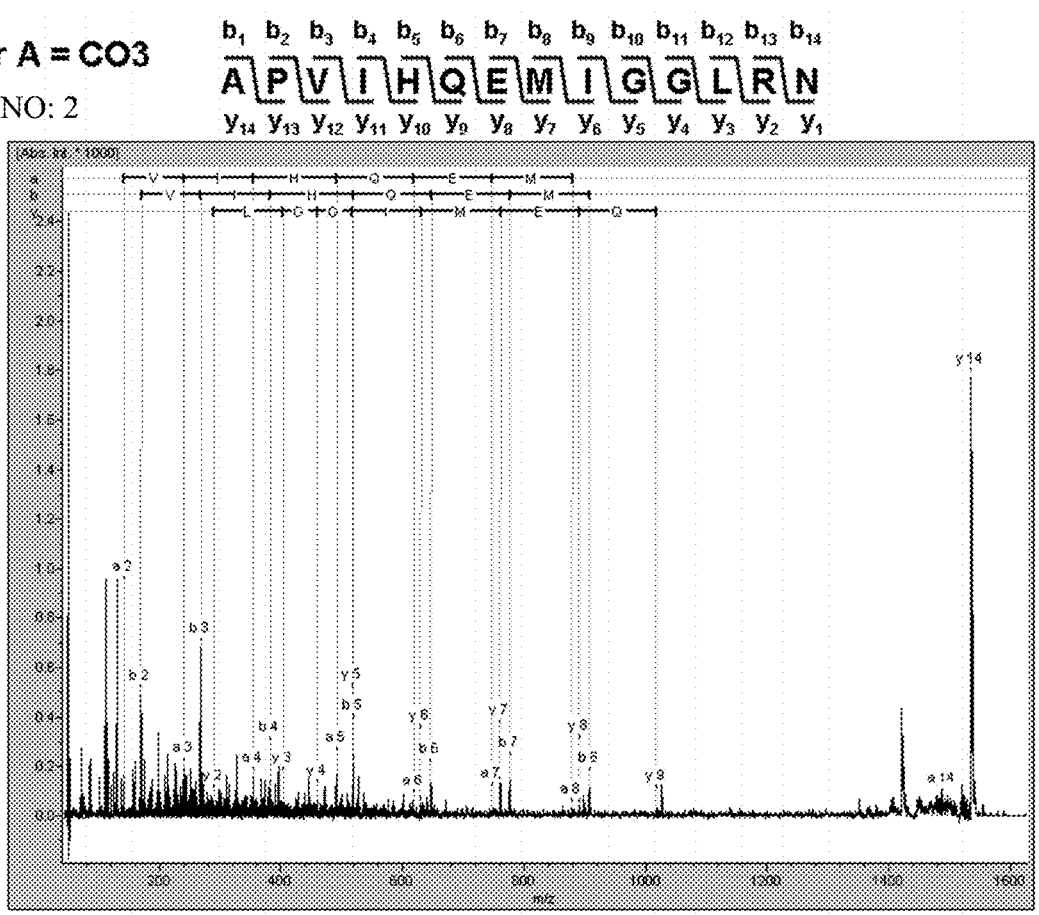
FIG. 4 illustrates the MS/MS spectrum of CO3 by TOF/TOF mass spectrometer.

FIG. 2 shows the results of differential analysis in the case of Marker A. As shown in FIG. 4, Marker A is Complement C3-derived peptides CO3. FIG. 2 shows the comparison between subjects not suffering from psychiatry disease (NDC) and cognitive impairment (AD, MCI, DLB and FTD) related to CO3. In the results of t-test, area values of cognitive impairment (AD, MCI, DLB and FTD) were significantly higher than NDC (p<0. 05).

Figure 3:
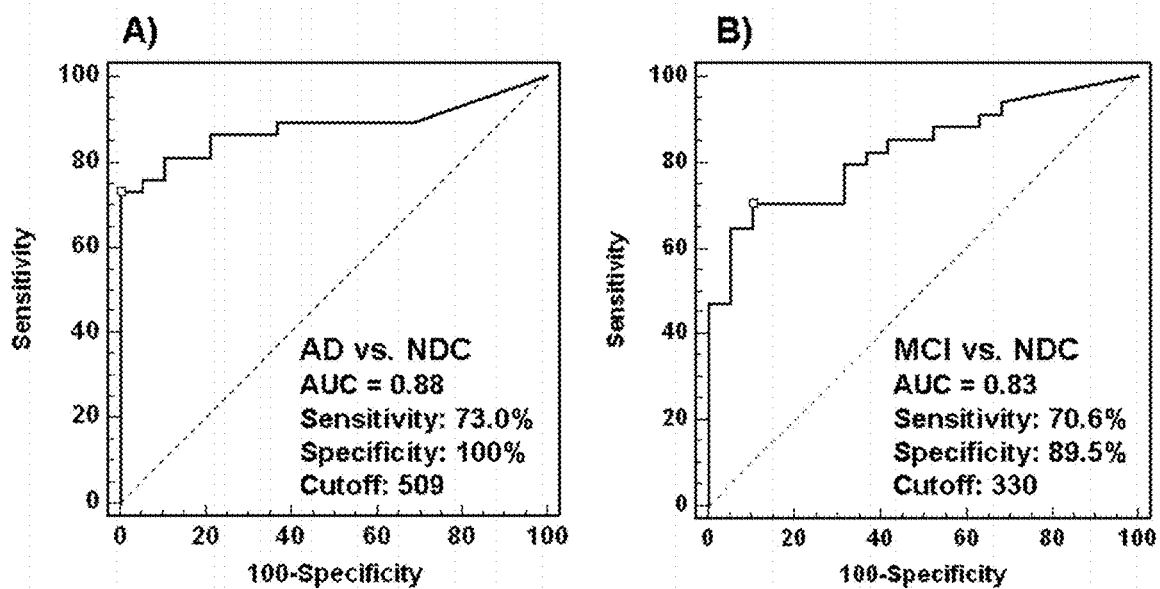
FIG. 3 illustrates the ROC curves of CO3 expressed by SEQ ID NO: 2. Definition of the ROC curve, see the section on the results of Example.

From the results of FIG. 2, in order to evaluate the extent to Which the Marker A is useful as biomarker, the analysis by receiver operating characteristic (ROC) curve was performed. A) and B) in FIG. 3 shows respectively the ROC curve of the comparison of AD vs. NDC and MCI vs. NDC. If the area value (hereinafter referred to as the AUC value) of under the ROC curve is close to 1, the usefulness as biomarker of Marker A will be higher. In A) and B) of FIG. 3, the typical values of sensitivity and specificity are the values of the point (open square in the figure) of the coordinate on ROC curve that the distance is minimized when a straight line was drawn to ROC curve from the point of 100% on y-axis. The value of cut-off giving this point becomes a useful threshold to distinguish between the different groups, and the values of sensitivity and specificity at that time (i.e., above the typical values) becomes an indicator of the usefulness of biomarkers together with AUC values. In A) of FIG. 3, as typical values in AD vs. NDC, the sensitivity was 73.0%, the specificity was 100%, and the AUC value was 0.88. In B) of FIG. 3, as typical values in MCI vs. NDC, the sensitivity was 70.6%, the specificity was 89.5%, and the AUC value was 0.83.

Thus, it was revealed that Marker A was useful to distinguish AD and MCI with NDC. In particular, since MCI is the state of previous stage of AD, Marker A is considered to be an extremely useful marker to detect MCI for early diagnosis of potential subjects to migrate to AD.

FIG. 4, for Marker A, illustrates the results of MS/MS spectrum using ultraflex TOF/TOF. The signals that show y-ions and b-ions have enough appeared, and the amino acid sequence could be readily identified. Mascot search was performed on this result and the protein of origin or the peptide (hereinafter referred to as intact proteins or peptides) is Complement C3, and the detected peptide was found that the sequence is APVIHQEMIGGLRN (SEQ ID NO: 2). CO3 of entry name of Swiss-Prot against Complement C3 will use as an abbreviation of the peptide name. Followings, for peptides other than CO3, entry name will use as peptide name, similarly.

Including the Marker A, the peptides that have difference in abundance between the groups in serum were measured MS./MS spectra using ultraflex TOF/TOF, and in addition to determining the amino acid sequence, the results identified intact proteins or peptides were shown below. For peptides other than Marker A, the signals that show y-ions and b-ions has enough appeared, and the amino acid sequence could be readily identified. The following amino acid sequence that shows a set of two sequences, the first sequence shows the amino acid sequence of intact proteins, and the second sequence shows the amino acid sequence of peptide detected by 2D-LC MALDI TOF-MS. The peptide comprising of the underlined portion in the first sequence correspond to the sequence of peptide detected by 2D-LC MALDI TOF-MS. The amino acid sequence starting at 0001 in the sequence shows the sequence of the N-terminus side.

(1) Complement C3-Derived Peptide CO3

CO3 shown as SEQ ID NO: 2 had formed a cluster by clustering using Pamassum software.

As shown in FIG. 2, area values of cognitive impairment (AD, MCI, DLB and FTD) were significantly higher than NDC (t-test, p<0.05). Thus, it was revealed that CO3 shown as SEQ ID NO: 2 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See FIGS. 3A), 3B) and Table 1).

```
                    Intact protein/peptide

0001 SPMYSIITPN ILRLESEETM VLEAHDAQGD VPVTVTVHDF PGKKLVLSSE

0051 KTVITPATNH MGNVTFFIPA NREFKSEKGR NKFVTVQAIT GTQVVEKVVL

0101 VSLQSGYLFI QTDKTIYTPG STVLYRIFTV NHKLLPVGRT VMVNIENPEG

0151 IPVKQDSLSS QNQLGVLPLS WDIPELVNMG QWKIRAYYEN SPQQVFSTEF

0201 EVKEYVLPSF EVIVEPTEKF YYIYNEKGLE VTITARFLYG KKVEGTAFVI

0251 FGIQDGEQRI SLPESLKRIP IEDGSGEVVL SRKVLLDGVQ NPRAEDINGK

0301 SLYVSATVIL HSGSDMVQAE RSGIPIVTSP YQIHFTKTPK YFKPGMPFDL

0351 MVFVTNPDGS PAYRVPVAVQ GEDTVQSLTQ GDGVAKLS1N THPSQKPLSI

0401 TVRTKKQELS EAEQATRTMQ ALPYSTVGNS NNYLHLSVLR TELRPGETLN

0451 VNFLLRMDRA HEAKIRYYTY LIMNKGRLLK AGRQVREPGQ DINVLPLSIT

0501 TDFIPSFRLV AYYTLIGASG QREVVADSVW VDVKDSCVGS INVKSGQSED

0551 RQPVPGQQMT LKIEGDHGAR VVLVAVDKGV FVLNKKNKLT QSKIWDVVEK

0601 ADIGCTPGSG KDYAGVFSDA GLTFTSSSGQ QTAQRAELQC PQPAARRRRS

0651 VQLTEKRMDK VGKYPKELRK CCEDGMRENP MRFSCQRRTR FISLGEACKK

0701 VFLDCCNYIT ELRRQHARAS HIGLARSNLD EDIIAEENIV SRSEPPESWL

0751 WNVEDLKEPP KNGISTKLMN IFLKDSITTW EILAVSMSDK KGICVADPFE

0801 VTVMQDFFID LRLPYSVVRN EQVEIRAVLY NYRQNQELKV RVELLHNPAF

0851 CSLATTKRRH QQTVTIPPKS SLSVPYVIVP LKTGLQEVEV KAAVYHHFIS

0901 DGVRKSLKVV PEGIRMNKTV AVRTLDPERL GREGVQKEDI PPADLSDQVP

0951 DTESETRILL QGTPVAQMTE DAVDAERLKH LIVTPSGCGE QNMIGMTPTV

1001 IAVHYLDETE QWEKTGLEKR QGALELIKKG YTQQLAFRQP SSAFAAINKR

1051 APSTWLTAYV VKVFSLAVNI IAIDSQVICG AVKWHILEKQ KPDGVFQEDA

1101 PVIHQEMIGG LRNNNEKDMA LTAFVLISLQ EAKDICEEQV NSLPGSITKA

1151 GDFLEANYMN LQRSYTVAIA GYALAQMGRL KGPLLNKFLT TAKDKNRWED

1201 PGKQINNVEA TSYALLALLQ LKDFDFVPPV VRWLNEQRYY GGGYGSTQAT

1251 FMVFQALAQY QKDAPDHQEL NLDVSLQLPS RSSKITHRIH WESASLLRSE

1301 ETKENEGFTV TAEGKGQGTL SVVTMYHAKA KDQLTCNKFD LKVTIKPAPE

1351 TEKRPQDAKN TMILEICTRY RGDQDATMSI LDISMMTGFA PDTDDLKQLA

1401 NGVDRYISKY ELDKAFSDRN TLIIYLDKVS HSEDDCLAFK VEQYFNVELI
```

| Intact protein/peptide |
|---|
| 1451 QPGAVKVYAY YNLEESCTRF YHPEKEDGKL NKLCRDELCR CAEENCFIQK |
| 1501 SDDKVTLEER LDKACEPGVD YVYKTRINKV QLSNDFDEYI MAIEQTIKSG |
| 1551 SDEVQVGQQR TFISPIKCRE ALKLEEKKHY LMWGLSSDFW GEKPNLSYII |
| 1601 GKDTWVEHWP EEDECQDEEN QKQCQDLGAF TESMVVFGCP N (SEQ ID NO: 1) |

Complement C3-Derived Peptide CO3

APVIHQEMIGGLRN (SEQ ID NO: 2)

(2) Transcription Factor AP-2 Gamma-Derived Peptide AP2C

Figure 5:
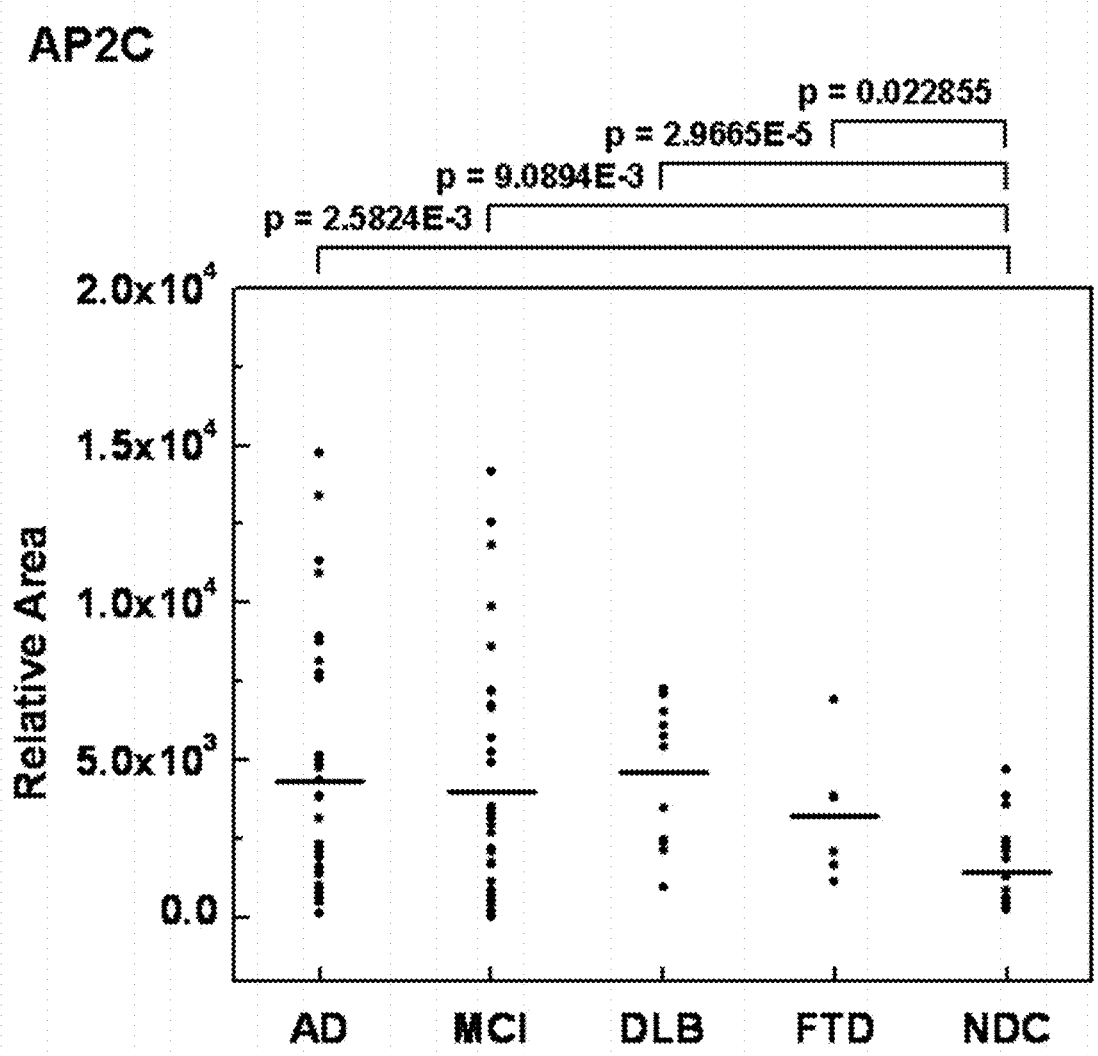
FIG. 5 illustrates the results of differential analysis of AP2C expressed by SEQ ID NO: 4. This figure shows a comparison between cognitive impairment patients (AD, MCI, DLB, FTD) and subjects not suffering from psychiatry disease (NDC).

For AP2C shown as SEQ ID NO: 4, area values of cognitive impairment (AD, MCI, DLB and FTD) were significantly higher than NDC. (t-test, $p<0.05$) (see FIG. 5)

Thus, it was revealed that AP2C shown as SEQ ID NO: 4 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

| Intact protein/peptide |
|---|
| 0001 MLWKIIDNVK YEEDCEDRHD GSSNGNPRVP HISSAGQHLY SPAPPLSHIG |
| 0051 VAEYQPPPYF PPPYQQLAYS QSADPYSHLG EAYAAAINPL HQPAPTGSQQ |
| 0101 QAWPGRQSQE GAGLPSHHGR PAGLLPHLSG LEAGAVSARR DAYRRSDLLL |
| 0151 PHAHALDAAG LAENLGLHDM PHQMDEVQNV DSQHLLLHDQ TVIRKGPISM |
| 0201 TKNPLNLPCQ KELVGAVMNP TEVFCSVPGR LSLISSISKY KVTVAEVQRR |
| 0251 LSPPECLNAS LLGGVLRRAK SKNGGRSLRE KLDKIGLNLP AGRRKAAHVT |
| 0301 LLTSLVEGEA VELARDFAYV CEAEFPSKPV AEYLTRPHLG GRNEMAARKN |
| 0351 MLLAAQQLCK EFTELLSQDR TPHGTSRLAP VLETNIQNCL SHFSLITHGE |
| 0401 GSQAICAAVS ALQNYIKEAL IVIDKSYMNP GDQSPADSNK TLEKMEKHRK (SEQ ID NO: 3) |

Transcription Factor AP-2 Gamma-Derived Peptide AP2C

PGRQSQEGAGLPSHHG (SEQ ID NO: 4)

(3) Synapsin-3-Derived Peptide SYN3

Figure 6:
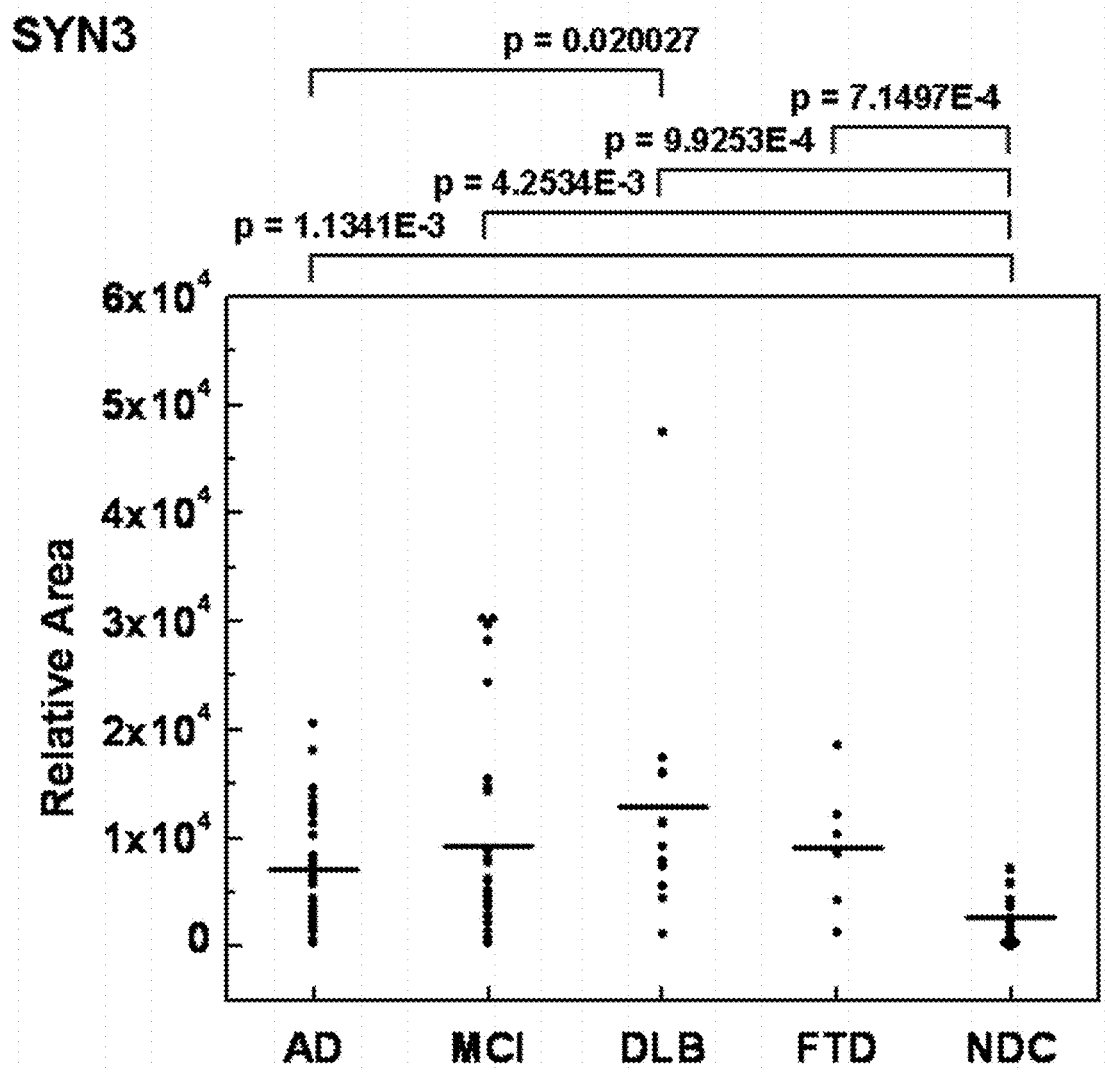
FIG. 6 illustrates the results of differential analysis of SYN3 expressed by SEQ ID NO: 6, This figure shows a comparison between cognitive impairment patients (AD, MCI, DLB, FTD) and subjects not suffering from psychiatry disease (NDC).

For SYN3 shown as SEQ ID NO: 6, area values of cognitive impairment (AD, MCI, DLB and FTD) were significantly higher than NDC. (t-test, $p<0.05$) (see FIG. 6)

Thus, it was revealed that SYN3 shown as SEQ ID NO: 6 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

| Intact protein/peptide |
|---|
| 0001 MNFLRRRLSD SSFMANLPNG YMTDLQRPDS STSSPASPAM ERRHPQPLAA |
| 0051 SFSSPGSSLF SSLSSAMKQA PQATSGLMEP PGPSTPIVQR PRILLVIDDA |
| 0101 HTDWSKYFHG KKVNGETEIR VEQAEFSELN LAAYVTGGCM VDMQVVRNGT |

-continued

| Intact protein/peptide |
|---|
| 0151 KVVSRSFKPD FILVRQHAYS MALGEDYRSL VIGLQYGGLP AVNSLYSVYN |
| 0201 FCSKPWVFSQ LIKIFHSLGP EKFPLVEQTF FPNHKPMVTA PHFPVVVKLG |
| 0251 HAHAGMGKIK VENQLDFQDI TSVVAMAKTY ATTEAFIDSK YDIRIQKIGS |
| 0301 NYKAYMRISI SGNWKANIGS AMLEQVAMTE RYRLWVDSCS <u>EMFGGLDICA</u> |
| 0351 <u>VKAVHSKDGR</u> DYTIEVMDSS MPLIGEHVEE DRQLMADLVV SKMSQLPMPG |
| 0401 GTAPSPLRPW APQIKSAKSP GQAQLGPQLG QPQPRPPPQG GPRQAQSPQP |
| 0451 QRSGSPSQQR ISPQGQQPLS PQSGSPQQQR SPGSPQLSRA SSGSSPNQAS |
| 0501 KPGAITASQP RPPVQGRSTS QQGEESKKPA PPHPHLNKSQ SITNSISTSD |
| 0551 TSQRGTPSED EAKAETIRNL RKSFASLFSD (SEQ ID NO: 5) |

Synapsin-3-Derived Peptide SYN3

(SEQ ID NO: 6)
EMFGGLDICAVKAVHSK (4) Oxytocin Receptor-Derived Peptide OXYR

Figure 7:
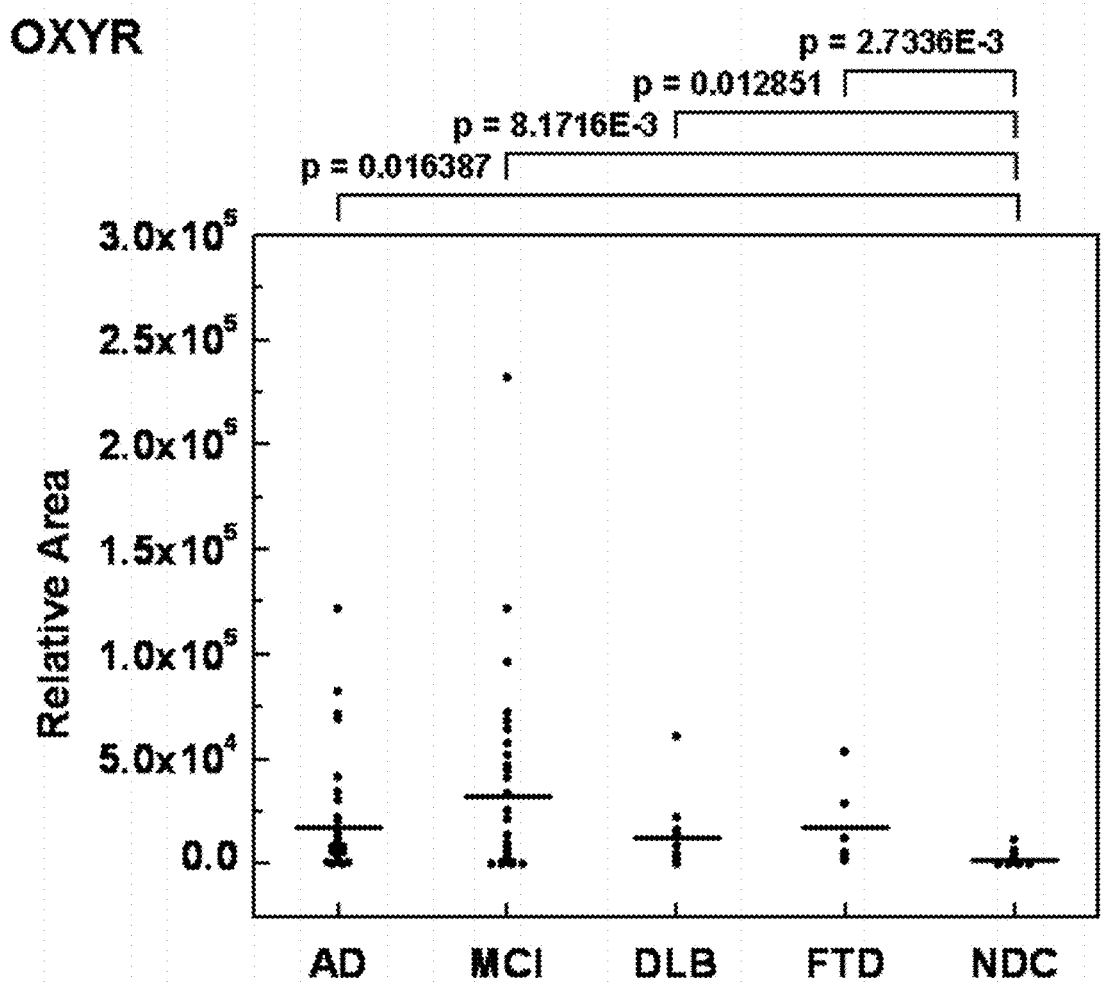
FIG. 7 illustrates the results of differential analysis of OXYR expressed by SEQ ID NO: 8. This figure shows a comparison between cognitive impairment patients (AD, MCI, DLB, FTD) and subjects not suffering from psychiatry disease (NDC).

For OXYR shown as SEQ ID NO: 8, area values of cognitive impairment (AD, MCI, DLB and FTD) were significantly higher than NDC. (t-test, $p<0.05$) (see FIG. 7) Thus, it was revealed that OXYR shown as SEQ ID NO: 8 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

| Intact protein/peptide |
|---|
| 0001 MEGALAANWS AEAANAS<u>AAP PGAEGNRT</u>AG PPRRNEALAR VEVAVLCLIL |
| 0051 LLALSGNACV LLALRTTRQK HSRLFFFMKH LSIADINVAV FQVLPQLLWD |
| 0101 ITFRFYGPDL LCRLVKYLQV VGMFASTYLL LLMSLDRCLA ICQPLRSLRR |
| 0151 RTDRLAVIAT WLGCLVASAP QVHIFSLREV ADGVFDCWAV FIQPWGPKAY |
| 0201 ITWITLAVYI VPVIVLAACY GLISFKIWQN LRLKTAAAAA AEAPEGAAAG |
| 0251 DGGRVALARV SSVKLISKAK IRTVKMTFII VLAFIVCWTP FFFVQMWSVW |
| 0301 DANAPKEASA FIIVMLLASL NSCCNPWIYM LFTGHLFHEL VQRFLCCSAS |
| 0351 YLKGRRLGET SASKKSNSSS EVISHRSSSQ RSCSQPSTA (SEQ ID NO: 7) |

Figure 8:
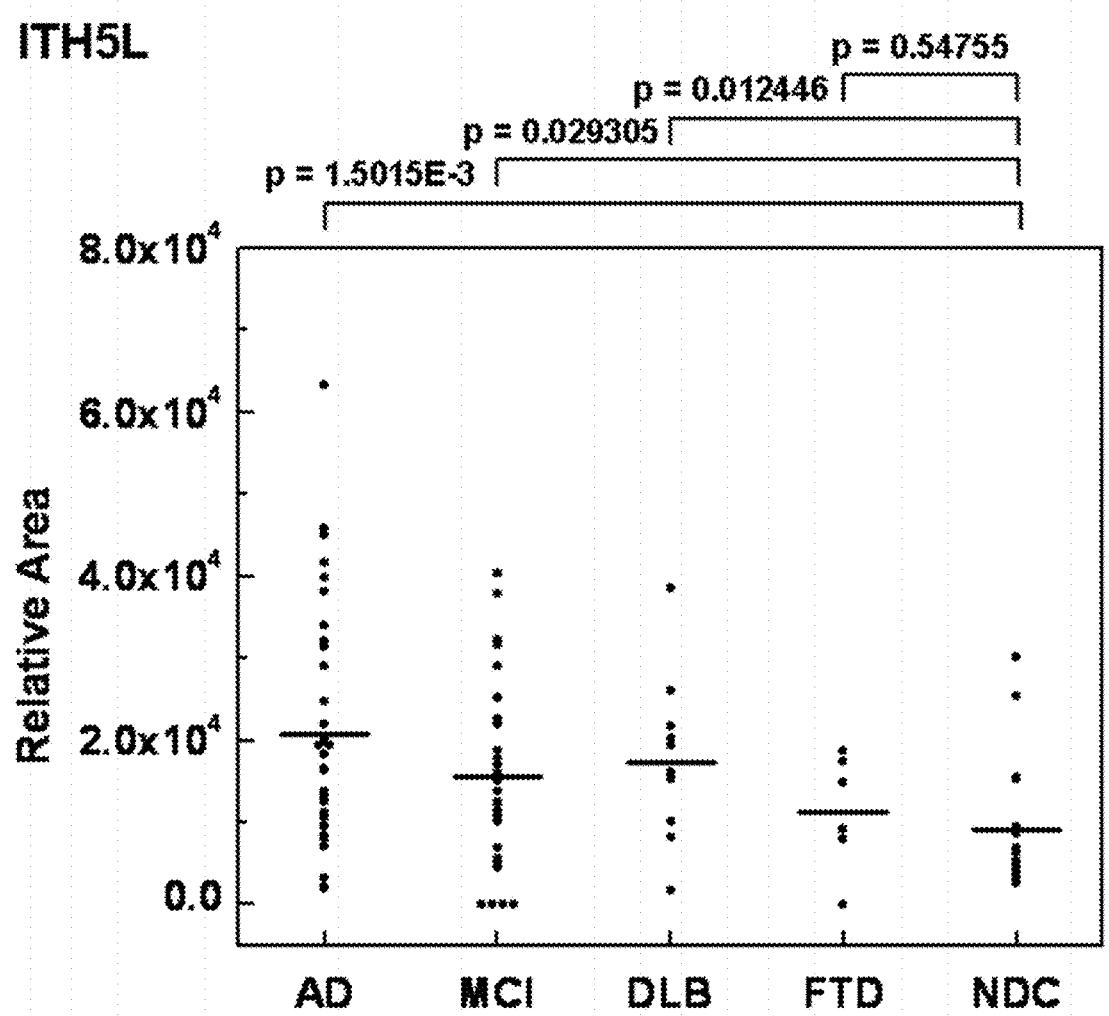
FIG. 8 illustrates the results of differential analysis of ITH5L expressed by SEQ ID NO: 10. This figure shows a comparison between cognitive impairment patients (AD, MCI, DLB, FTD) and subjects not suffering from psychiatry disease (NDC).

Oxytocin Receptor-Derived Peptide OXYR (SEQ ID NO: 8)
AAPPGAEGNRT (5) Inter-Alpha-Trypsin Inhibitor Heavy Chain H5-Like Protein-Derived Peptide ITH5L For ITH5L shown as SEQ ID NO: 10, area values of cognitive impairment (AD, MCI and DLB) were significantly higher than NDC, (t-test, $p<0.05$) (see FIG. 8)

Thus, it was revealed that ITH5L shown as SEQ ID NO: 10 was useful to distinguish patient of cognitive impairment (AD, MCI and DLB) with subjects not suffering from psychiatry disease (NDC). According to the analysis by receiver operating characteristic (ROC) curve, CO3 was clearly useful to distinguish AD and MCI with NDC. (See Table 1)

```
                    Intact protein/peptide

0001 GPPVPASSST KLLMTSYSMR STVVSRYAHT LVTSVLFNPH AEAHEAIFDL

0051 DLPHLAFISN FTMTINNKVY IAEVKEKHQA KKIYEEAHQQ GKTAAHVGIR

0101 DRESEKERIS TSLAAGTEVT FSLAYEELLQ RHQGQYQLVV SLRPGQINKR

0151 LSIEVTVSER TGISYVHIPP LRFGRLKINA HASEVDSPPS TRIERGETCV

0201 R1TYCPTLQD QSSISGSGIM ADELVQYDVV MEDIIGDVQI YDDYFIHYEA

0251 PRGLPPMEKN VVEVIDVSSS MFGTKMEQTK TAMNVILSDL QANDYFNIIS

0301 ESDIVNVWKA GGSIQATIQN VHSAKDYLHC MEADGWTDVN SALLAAASVL

0351 NHSNQEPGRG PSVGRIPLII FLTDGEPTAG VTTPSVILSN VRQALGHRVS

0401 LESLAFGDDA DFTLLRRLSL ENRGIARRIY EDTDAALQLK GINEEISMPL

0451 LADVRLNYLG GLVGASPWAV FPNYEGGSEL VVAGQVQPGK QELGIBLAAR

0501 GPKDQLLVAH HSEGATNNSQ KAFGCPGEPA INVAHFIRRL WAYVTIGELL

0551 DAHFQARDTT TRHLLAAKVL NLSLEYNEVT PLTSLVMVQP KQASEEIRRQ

0601 TSTSAGPDTI MPSSSSRHGL GVSTAQPAIN PKVISPKSRP VKPKFYLSST

0651 TTASTKKMLS SKELEPLGES PHTLSMPTYP KAKIPAQQDS GTLAQPTLRT

0701 KPTILYPSNS GTLLPLKPGS LSHQNPDILP TNSRIQVPPV KPGIPASPKA

0751 DTVKCVTPLH SKPGAPSHPQ LGAUFSQAPK GLPQSRPGVS TLQVPKIPLH

0801 TRPRVPAPKT RNNMPHLGPG ILLSKTPKIL LSLKPSAPPH QISTSISLSK

0851 PETPNPHMPQ TPLPPRPDRP RPPLPESLST FPNTISSSTG PSSTTTTSVL

0901 GEPLPMPFTP TLPPGRFWHQ YDLLPGPQRT RQVLGPSRPG VPTMSLLNSS

0951 RPTPEGSPPN LPILLPSSIL PEAISLLLLP EELELLSESM VESKFVESLN

1001 PPAFYTFLTP DEDGSPNWDG NSEEILGGAG GSMESQGSSV GLAKGTLPSI

1051 FTESSSVDGD PHFVIQIPHS EEKICFTLNG HPGDLLQLIE DPKAGLHVSG

1101 KULGAPPRPG HKDQTRTYFQ IITVTIDKPR AYTLIISRSS ISLRGEGTLR

1151 LSWDQPALLK RPQLELYVAA AARLTLRLGP YLEFLVLRHR YRHPSTLQLP

1201 HLGFYVANGS GLSRSARGLI GQFQHADIRL VTGPMGPCLR RHHGPDVPVI

1251 LGKRLLKDSP RLLPRWASCW LVKRSHVELL LGHPYISYVL (SEQ ID NO: 9)
```

Inter-Alpha-Trypsin Inhibitor Heavy Chain H5-Like Protein-Derived Peptide ITH5L (SEQ ID NO: 10)
RVSLFSLAFGDDAD (6) E3 Ubiquitin-Protein Ligase HERC2-Derived Peptide HERC2

Figure 9:
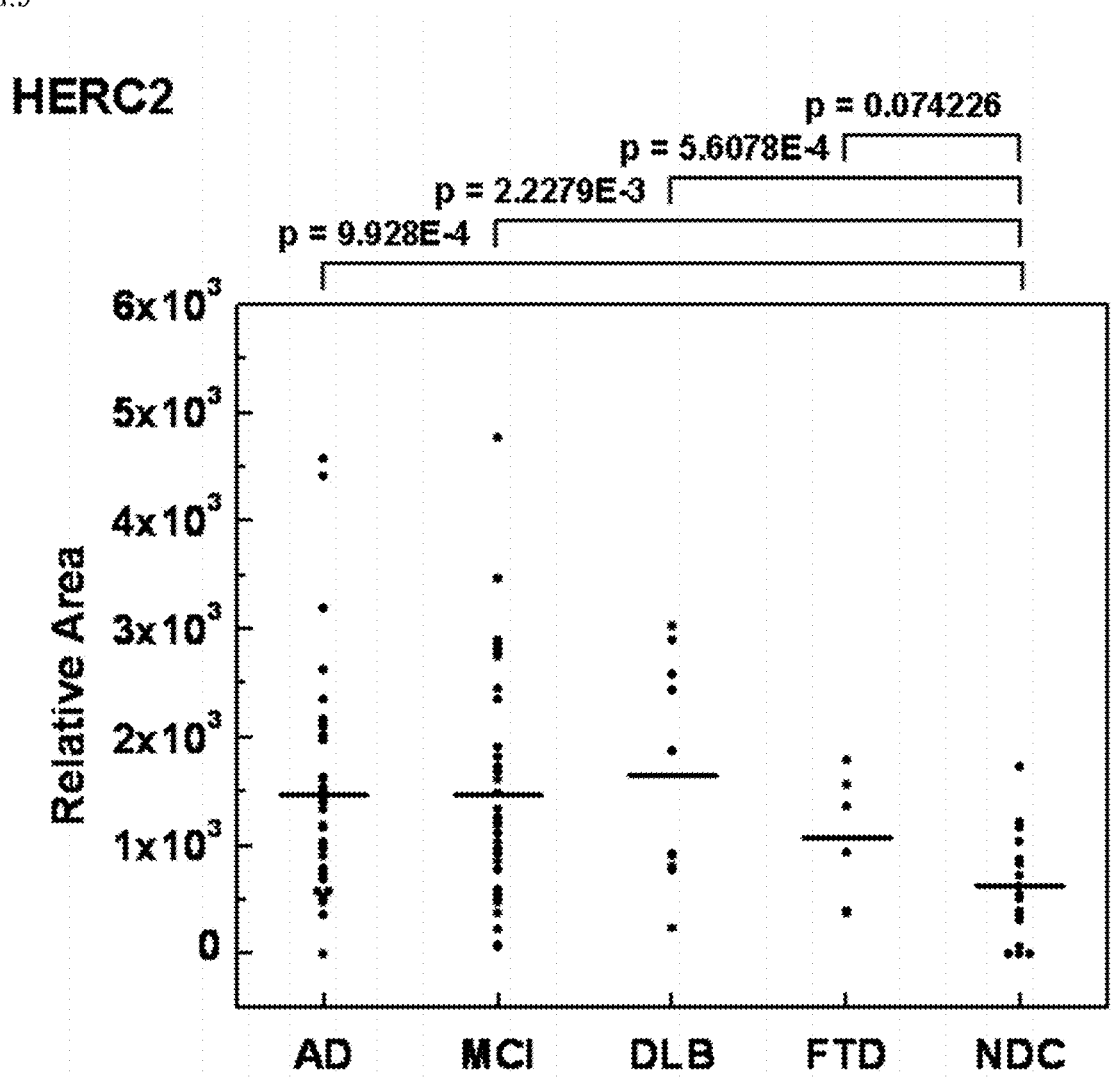
FIG. 9 illustrates the results of differential analysis of HERC2 expressed by SEQ ID NO: 12. This figure shows a comparison between cognitive impairment patients (AD, MCI, DLB, FTD) and subjects not suffering from psychiatry disease (NDC).

For HERC2 shown as SEQ ID NO: 12, area values of cognitive impairment (AD, MCI and DLB) were significantly higher than NDC. (t-test, $p<0.05$) (see FIG. 9)

Thus, it was revealed that HERC2 shown as SEQ ID NO: 12 was useful to distinguish patient of cognitive impairment (AD, MCI and DLB) with subjects not suffering from psychiatry disease (NDC). According to the analysis by receiver operating characteristic (ROC) curve, CO3 was clearly useful to distinguish AD and MCI with NDC. (See Table 1)

```
                   Intact protein / peptide

0001    MPSESFCLAA QARLDSKWLK TDIQLAFTRD GLCGLWNEMV KDGEIVYTGT

0051    ESTQNGELPP RKDDSVEPSG TKKEDLNDKE KKDEEETPAP IYRAKSILDS

0101    WVWGKQPDVN ELKECLSVUV KEQQALAVQS AITILSALRL KQRLVILERY

0151    FIALNRIVFQ ENVKVKWKSS GISLPPVDKK SSRPAGKGVE GLARVGSRAA
```

| Intact protein / peptide |
|---|
| 0201 LSFAFAFLRR AWRSGEDADL CSELLQESLD ALRALPEASL FDESTVSSVW |
| 0251 LEVVERATRF LRSVVTGDVH GTPATKGPGS IPLQDQHLAL AILLELAVQR |
| 0301 GTLSQMLSAI LLLLQLWDSG AQETDNERSA QGTSAPLLPL LQRFQSIICR |
| 0351 KDAPHSEGDM HLLSGPLSPN ESFLRYLTLP QDNELAIDLR QTAVVMAHL |
| 0401 DRLATPCMPP LCSSPTSHKG SLQEVIGWGL IGWKYYANVI GPIQCEGLAN |
| 0451 LGVTQIACAE KRFLILSRNG RVYTQAYNSD TLAPQLVQGL ASRNIVKIAA |
| 0501 HSDGHHYLAL AATGEVYSWG CGDGGRLGHG DTVPLEEPKV ISAFSGKQAG |
| 0551 KHVVHIACGS TYSAAITAEG ELYTWGRGNY GRLGHGSSED EAIPMINAGL |
| 0601 KGLKYIDVAC GSGDAQTLAV TENGQVWSWG DGDYGKLGRG GSDGCKTPKL |
| 0651 IEKLQDLDVV KVRCGSQFSI ALTKDGQVYS WGKGDNQRLG HGTEEHVRYP |
| 0701 KLLEGLQGKK VIDVAAGSTH CLALTEDSEV HSWGSNDQCQ HFDTLRVTKP |
| 0751 EPAALPGLDT KHIVGIACGP AQSFAWSSCS EWSIGLRVPF VVDICSMIFE |
| 0801 QLDLLLRQVS EGMDGSADWP PPQEKECVAV ATLNLLRLQL HAAISHQVDP |
| 0851 EFLGLGLGSI LLNSLKQTVV TLASSAGVLS TVQSAAQAVL QSGWSVLLPT |
| 0901 AEERARALSA LLPCAVSGNE VNISPGRRFM IDLLVGSLMA DGGLESALHA |
| 0951 AITAEIQDIE AKKEAQKEKE IDEQEANAST FHRSRTPLDK DLINTGICES |
| 1001 SGKQCLPLVQ LIQQLLRNIA SQTVARLKDV ARRISSCLDF EQHSRERSAS |
| 1051 LDLLLRFQRL LISKLYPGES IGQTSDISSP ELMGVGSLLK KYTALLCTHI |
| 1101 GDILPVAASI ASTSWRHFAE VAYIVEGDFT GVLLPEINVS IVIILSKNAG |
| 1151 LMQEAGAVPL LGGLLEHLDR FNHLAPGKER DDHEELAWPG IMESFFTGQN |
| 1201 CRNNEEVTLI RKADLENHNK DGGFWTVIDG KVYDIKDFQT QSLTGNSILA |
| 1251 QFAGEDPVVA LEAALQFEDT RESMHAFCVG QYLEPDQEIV TIPDLGSLSS |
| 1301 PLIDTERNLG LLLGLHASYL AMSTPLSPVE IECAKWLQSS IFSGGLQTSQ |
| 1351 IHYSYNEEKD EDHCSSPGGT PASKSRLCSH RRALGDHSQA FLQAIADNNI |
| 1401 QDHNVKDFLC QIERYCRQCH LTTPIMFPPE HPVEEVGRLL LCCLLKHEDL |
| 1451 GHVALSLVHA GALGIEQVKH RTLPKSVVDV CRVVYQAKCS LIKTHQEQGR |
| 1501 SYKEVCAPVI ERLRFLFNEL RPAVCNDLSI MSKFKLLSSL PRWRRIAQKI |
| 1551 IRERRKKRVP KKPESTDDEEIKIGNEESDLE EACILPHSPI NVDKRPIALK |
| 1601 SPKDKWQPLL STVTGVHKYK WLKQNVQGLY PQSPLLSTIA EFALKEEPVD |
| 1651 VEKMRKCLLK QLERAEVRLE GIDTILKLAS KNFLLPSVQY AMFCGWQRLI |
| 1701 PEGIDIGEPL TDCLKDVDLI PPENRMLLEV TFGKLYAWAV QNIRNVLMDA |
| 1751 SAKFKELGIQ PVPLQTITNE NPSGPSLGTI PQARFLINML SMLTLQHGAN |
| 1801 NLDLLLNSGM LAIXQTALRL IGPSCDNVEE DMNASAQGAS ATVLEETRKE |
| 1851 TAPVQLPVSG PELAAMMKIG TRVMRGVDWK WGDQDGPPPG LGRVIGELGE |
| 1901 DGWIRVQWDT GSTNSYRMGK EGKYDLKLAE LPAAAQPSAE DSDTEDDSEA |
| 1951 EQTERNIHPT AMMFTSTINL LQTLCLSAGV HAEIMQSEAT KTLCGLLRML |
| 2001 VESGTIDKTS SPNRIVYREQ HRSWCTLGFV RSIALTPQVC GALSSPQWIT |
| 2051 LLMKVVEGHA PFIATSLQRQ ILAVHLLQAV LPSWDKTEIU RDMKCLVEKL |

-continued

| | Intact protein / peptide |
|---|---|
| 2101 | FDFLGSLLTT CSSDVPLLRE STLRRRRVRP QASLTATHSS TLAEEVVALL |
| 2151 | RTLHSLTQWN GLINKYINSQ LRSITHSFVG RPSEGAQLED YFPDSENPEV |
| 2201 | GGLMAVLAVI GGIDGRLRLG GQVMHDEFGE GTVTRITPKG KITVQRSDMR |
| 2251 | TCRVCPLNQL KPLPAVAFNV NNLPFTEPML SVWAQLVNLA GSKLEKHKIK |
| 2301 | KSTKQAFAGQ VDLDLLRCQQ LKLYILKAGR ALLSHQDKIR QILSQPAVQE |
| 2351 | TGTVHTDDGA VVSPDLGDMS PEGPQPPMIL LQQLLASAFQ PSPVKAIFDK |
| 2401 | QELEAAALAV CQCLAVESTH PSSPGFEDCS SSEATTPVAV QUIRPARVKR |
| 2451 | RKQSPVPALP IVVQLMEMGF SRRNIEFAIK SLTGASGNAS SLPGVEALVG |
| 2501 | WLLDHSDIQV TELSDADTVS DEYSDEEVVE DVDDAAYSMS TGAVVTESQT |
| 2551 | YKKRADFLSN DDYAVYVREN IQVGMMVRCC RAYEEVCEGD VGKVIKLDRD |
| 2601 | GLHDLNVQCD WQQKGGTYWV RYIHVELIGY PPPSSSSHIK IGDKVRVKAS |
| 2651 | VTTPKYKWGS VTHQSVGVVK MS ANGKINI VDFPQQSHWT GLLSEMELVP |
| 2701 | SLHPGVTCDG CQMFPINGSR FKCRNCDDFD FCETCFKTKK HNTRHTFGRI |
| 2751 | NEPGQSAVFC GRSGKQLKRC HSSQPGMLLD SWSRMVKSLN VSSSVNQASR |
| 2801 | LIDGSEPCWQ SSGSQGKHWI RLEIFPDVLV HRLKMIVDPA DSSYMPSINV |
| 2851 | VSGGNSLNNL IELKTININP SDTTVPLLND CTEYHRYIEI AIKQCRSSGI |
| 2901 | DCKIHGLILL GRIRAEEEDL AAVPFLASDN EEEEDEKGNS GSLIRKKAAG |
| 2951 | LESAATIRTK VFVWGLNDKD QLGGLKGSKI KVPSFSETLS ALNVVQVAGG |
| 3001 | SKSLFAVTVE GKVYACGEAT NGRLGLGISS GIVPIPRQII ALSSYVVKKV |
| 3051 | AVHSGGRHAr ALTVDGKVFS WGEGDDGKLG HFSRMNCDKP RLIEALKTKR |
| 3101 | IRDIACGSSH SAALTSSGEL YTWGLGEYGR LGHGDNITQL KPKMVKVLLG |
| 3151 | HRVIQVACGS RDAQTLALTD EGLVFSWGDG DFGKLGRGGS EGCNIPQNIE |
| 3201 | RLNGQGVCQI ECGAQFSLAL TKSGVVWTWG KGDYFRLGHG SDVHVRKPQV |
| 3251 | VEGLRGKKIV HVAVGALHCL AVTDSGQVYA WGDNDHGQQG NGTTTVNRKP |
| 3301 | TINQGLEGQK ITRVACGSSH SVAWTTVDVA TPSVHEPVLF QTARDPLGAS |
| 3351 | YLGVPSDADS SAASNKISGA SNSKPNRPSL AKILLSLDGN LAKQQALSHI |
| 3401 | LTALQIMYAR DAVVGALMPA AMIAPVECPS FSSAAPSDAS AMASPMNGEE |
| 3451 | CMLAVDIEDR LSPNPWQEKR EIVSSEDAVT PSAVTPSAPS ASARPFIPVT |
| 3501 | DDLGAASIIA ETMTKTKEDV ESQNKAAGPE PQALDEFTSL LIADDTRVVV |
| 3551 | DLLKLSVCSR AGDRGRDVLS AVLSGMGTAY PQVADMLLEL CVTELEDVAT |
| 3601 | DSQSGRLSSQ PVVVESSHPY TDDTSTSGTV KIPGAEGLRV EFDRQCSTER |
| 3651 | RHDPLTVMDG VNRIVSVRSG REWSDWSSEL RIPGDELKWK FISDGSVNGW |
| 3701 | GWRFTVYPIM PAAGPKELLS DRCVLSCPSM DIVTCLLDFR LNLASNRSIV |
| 3751 | PRLAASLAAC AQLSALAASH RMWALQRLRK LLTTEFGQSI NINRLLGEND |
| 3801 | GETRALSFTG SALAALVKGL PEALQRQFEY EDPIVRGGKQ LLHSPFFKVL |
| 3851 | VALACDLELD TLPCCAETHK WAWFRRYCMA SRVAVALDKR TPLPRLFLDE |
| 3901 | VAKKIRELMA DSENMDVLHE SHDIFKREQD EQLVQWMNRR PDDWTLSAGG |
| 3951 | SGTIYGWGHN HRGQLGGIEG AKVKATTPCE ALATLRPVQL IGGEQTLFAV |
| 4001 | TADGKLYAIG YGAGGRLGIG GIESVSTPTL LESIQHVFIK KVAVNSGGKH |

| | Intact protein / peptide |
|---|---|
| 4051 | CLALSSEGEV YSWGEAEDGK LGHGNRSPCD RPRVIESLRG IEVVDVAAGG |
| 4101 | AHSACVTAAG DLYTWGKGRY GRLGHSDSED QLKPKLVEAL QGHRVVDIAC |
| 4151 | GSGDAQTLCL TDDDTVWSWG DGDYGKLGRG GSDGCKATMK IDSITGLGVV |
| 4201 | KVECGSQFSV ALTKSGAVYT WGKGDYHRLG HGSDDHVRRP RQVQGLQGKK |
| 4251 | VIAIATGSLH CVCCTEDGEV YTWGDNDEGQ LGDGTTNAIQ RPRLVAALQG |
| 4301 | KKNNRVACGS AHTLAWSTSK PASAGKLPAQ VPMEYNHLQE IPIIALRNRL |
| 4351 | LLIEHLSELF CPCIPMFDLE GSLDETGLGP SVGFDTLRGI LISQGKEAAF |
| 4401 | RKVVQATMVR DRQHGPVVEL NRIQVKRSRS KGGLAGPDGT KSVFGQMCAK |
| 4451 | MSSFGPDSLL LPHRVWKVKF VGESVDDCGG GYSESTAEIC EELQNGLTPL |
| 4501 | LIVTPNGRDE SGANRDCYLL SPAARAPVHS SMFRFLGVLL GIAIRTGSPL |
| 4551 | SLNLAEPVWK QLAGMSLTIA DLSEVDKDFI PGLMYIRDNE AFSEEFEAMS |
| 4601 | LPFTVPSASG QDIQLSSKHT HITLDNRAEY VRLAINYRLH EFDEQVAAVR |
| 4651 | EGMARVVPVP LUSLFTGYEL ETMVCGSPDI PLHLLKSVAT YKGIEPSASL |
| 4701 | IQWFWEVMES FSNTERSITL RFVWGRTRLP RTIADFRGRD FVIQVLDKYN |
| 4751 | PPDHELPESY TCFFLLKLPR YSCKQVLEEK LKYAIHFCKS IDTDDYARIA |
| 4801 | LIGEPAADDS SDDSDNEDVD SFASDSTQDY LTGH (SEQ ID NO: 11) |

E3 Ubiquitin-Protein Ligase HERC2-Derived Peptide HERC2

KLAELPAAAQPSAEDSD (SEQ ID NO: 12)

(7) Prothrombin-Derived Peptide THRB

Figure 10:
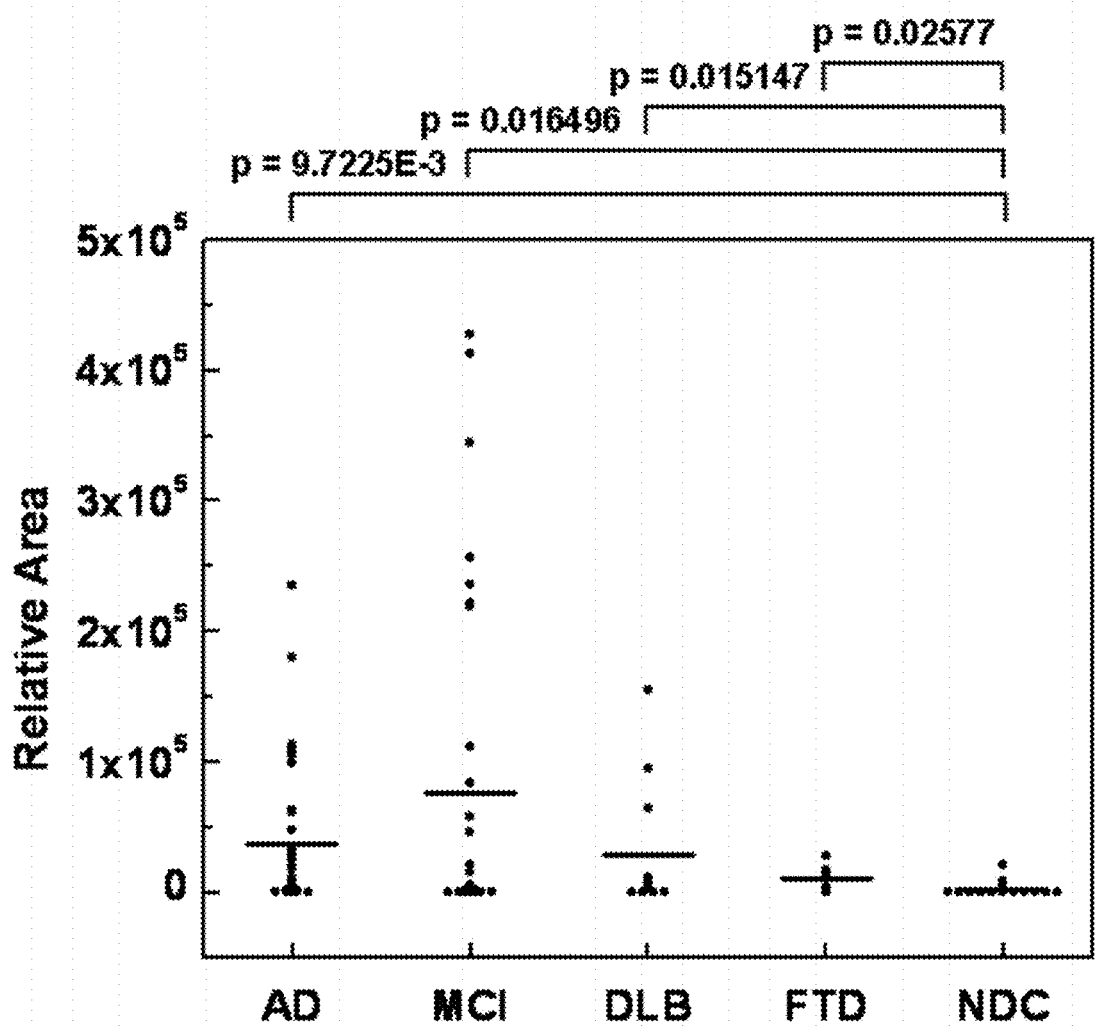
FIG. 10 illustrates the results of differential analysis of THRB expressed by SEQ ID NO: 14. This figure shows a comparison between cognitive impairment patients (AD, MCI, DLB, FTD) and subjects not suffering from psychiatry disease (NDC).

For THRB shown as SEQ ID NO: 14, area values of cognitive impairment (AD, MCI, DLB and FTD) were significantly higher than NDC. (t-test, $p<0.05$) (see FIG. 10)

Thus, it was revealed that THRB shown as SEQ ID NO: 14 was useful to distinguish patient of cognitive impairment (AD, MCI, DIM and FTD) with subjects not suffering from psychiatry disease (NDC). According to the analysis by receiver operating characteristic (ROC) curve, CO3 was clearly useful to distinguish AD and MCI with NDC. (See Table 1)

| | Intact protein/peptide |
|---|---|
| 0001 | ANTFLEEVRK GNLERECVEE TCSYEEAFEA LESSTAIDVF WAKYTACETA |
| 0051 | RTPRDKLAAC LEGNCAEGLG TNYRGHVNIT RSGIECQLWR SRYPHKPEIN |
| 0101 | STTIVGADLQ ENFCRNPDSS TTGPWCYTTD PTVRRQECSI PVCGQDQVTV |
| 0151 | AMTPRSEGSS VNLSPPLEQC VPDRGQQYQG RLAVTTHGLP CLAWASAQAK |
| 0201 | ALSKHQDFNS AVQLVENFCR NPDGDEEGVW CYVAGKPGDF GYCDLNYCEE |
| 0251 | AVEEETGDGL DEDSDRAIEG RTATSEYQTF FNPRTFGSGE ADCGLRPLFE |
| 0301 | KKSLEDKTER ELLESYIDGR IVEGSDAEIG MSPWQVMLFR KSPQELLCGA |
| 0351 | SLISDRWVLT AAHCLLYPPW DKNFTENDLL VRIGKHSRTR YERNIEKISM |
| 0401 | LEKIYIHPRY NWRENLDRDI ALMKLKKPVA FSDYIHPVCL PDRETAASLL |
| 0451 | QAGYKGRVTG WGNIKETWTA NVGKGQPSVL QVVNLPIVER PVCKDSTRIR |
| 0501 | ITDNMFCAGY KPDEGKRGDA CEGDSGGPFV MKSPFNNRWY QMGIVSWGEG |
| 0551 | CDRDGKYGFY THVFRLKKWI QKVIDQFGE (SEQ ID NO: 13) |

Figure 11:
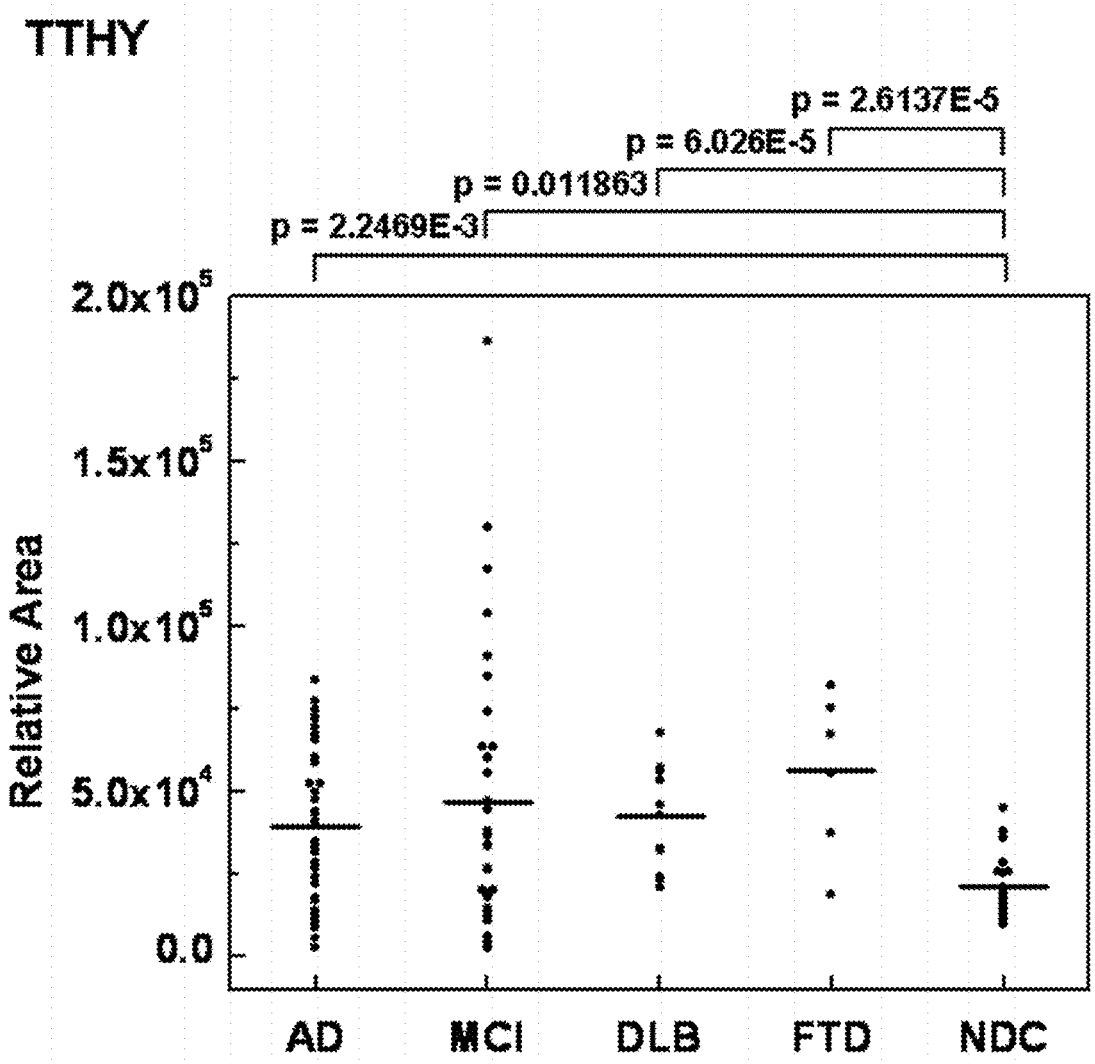
FIG. 11 illustrates the results of differential analysis of TTHY expressed by SEQ ID NO: 16. This figure shows a comparison between cognitive impairment patients (AD, MCI, DLB, FTD) and subjects not suffering from psychiatry disease (NDC).

Prothrombin-Derived Peptide THRB (SEQ ID NO: 14)
TATSEYQTFFNPRTFGSGEAD (8) Transthyretin-Derived Peptide TTHY For TTHY shown as SEQ ID NO: 16, area values of cognitive impairment (AD, MCI, DLB and FTD) were significantly higher than NDC. (t-test, p<0.05) (see FIG. 11)

Thus, it was revealed that TTHY shown as SEQ ID NO: 16 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

```
                  Intact protein/peptide

0001    GPTGTGESKC PLMVKVLDAV RGSPAINVAV HVFRKAADDT WEPFASGKTS

0051    ESGELHGLTT EEEFVEGIYK VEIDTKSYWK ALGISPFHEH AEVVFIANDS

0101    GPRRYTIAAL LSPYSYSTTA VVTNPKE (SEQ ID NO: 15)
```

Transthyretin-Derived Peptide TTHY (SEQ ID NO: 16)
AVRGSPAINVAVHVFRKAAD (9) Tumor Necrosis Factor Receptor Superfamily Member 16-Derived Peptide TNR16

Figure 12:
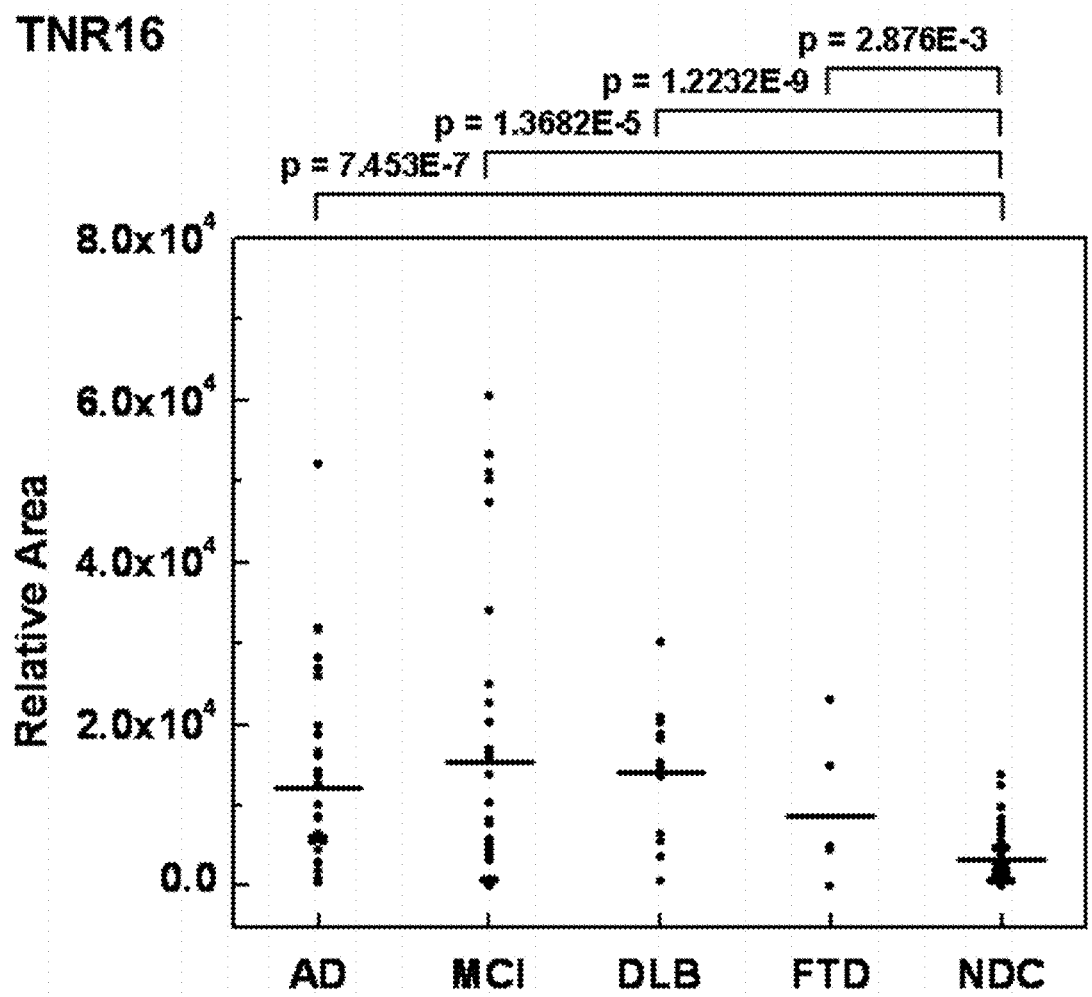
FIG. 12 illustrates the results of differential analysis of TNR16 expressed by SEQ ID NO: 18. This figure shows a comparison between cognitive impairment patients (AD, MCI, DLB, FTD) and subjects not suffering from psychiatry disease (NDC).

For TNR16 shown as SEQ ID NO: 18, area values of cognitive impairment (AD, MCI, DLB and FTD) were significantly higher than NDC. (t-test, p<0.05) (see FIG. 12)

Thus, it was revealed that TNR16 shown as SEQ ID NO: 18 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

Tumor Necrosis Factor Receptor Superfamily Member 16-Derived Peptide TNR16

(SEQ ID NO: 18)
QTASGQALKGDGGLYS

(10) Complement C4-A-Derived Peptide CO4-1

Figure 13:
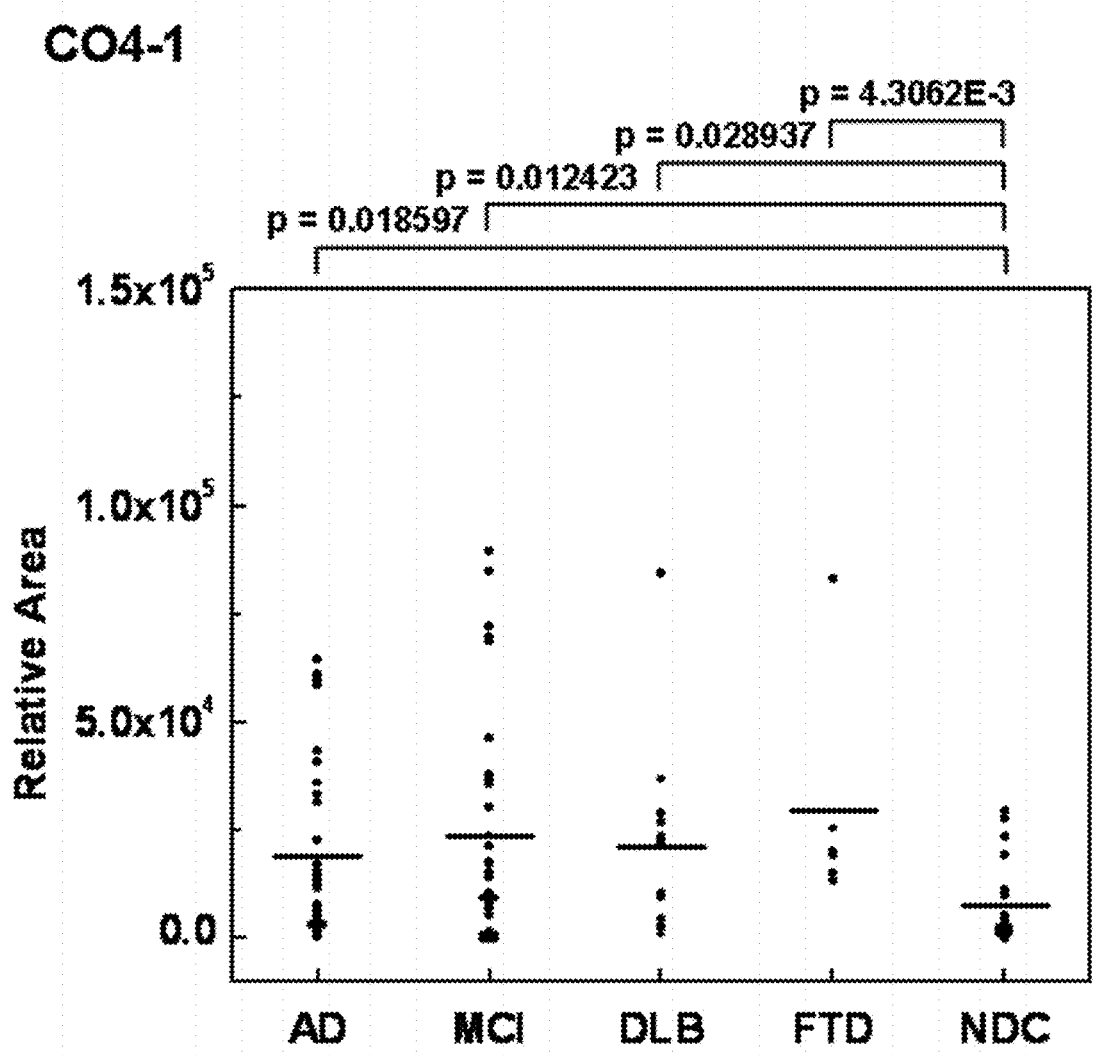
FIG. 13 illustrates the results of differential analysis of CO4-1 expressed by SEQ ID NO: 20. This figure shows a comparison between cognitive impairment patients (AD, MCI, DLB, FTD) and subjects not suffering from psychiatry disease (NDC).

For CO4-1 shown as SEQ ID NO: 20. area values of cognitive impairment (AD, MCI, DLB and FTD) were significantly higher than NDC. (t-test, p<0.05) (see FIG. 13)

Thus, it was revealed that CO4-1 shown as SEQ ID NO: 20 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

After Biosynthesis, Complement C4-A protein is divided into C4 beta chain, Complement C4-A alpha chain and. Complement C4 gamma chain by processing.

SEQ ID NO: 19 is amino acid sequence of intact Complement C4-A protein containing all of these processed peptides.

```
                  Intact protein/peptide

0001    KEACPTGLYT HSGECCKACN LGEGVAQPCG ANQTVCEPCL DSVTFSDVVS

0051    ATEPCKPCTE CVGLQSMSAP CVEADDAVCR CAYGYYQDET TGRCEACRVC

0101    EAGSGLVFSC QDKQNTVCEE CPDGTYSDEA NHVDPCLPCT VCEDTERQLR

0151    ECTRWADAEC EEIPGRWITR STPPEGSDST APSTQEPEAP PEQDLIASTV

0201    AGVVTTVMGS SQPVVTRGTT DNLIPVYCSI LAAVVVGLVA YIAFKRWNSC

0251    KQNKQGANSR PVNQTPPPEG EKLHSDSGIS VDSQSLHDQQ PHTQTASGQA

0301    LKGDGGLYSS LPPAKREEVE KLINGSAGDT WRHLAGELGY QPEHIDSFTH

0351    EACPVRALLA SWATQDSATL DALLAALRRI QRADIXESLC SESTAISPV (SEQ
        ID NO: 17)
```

```
Intact protein/peptide
                                                         (SEQ ID NO: 19)
0001  KPRLLLFSPS VVHLGVPLSV GVQLQDVPRG QVVKGSVFLR NPSRNNVPCS

0051  PKVDFTLSSE RDFALLSLQV PLKDAKSCGL HQLLRGPEVQ LVAHSPWLKD

0101  SLSRTTNIQG INLLFSSRRG HLFLQTDQPI YNPGQVRYR VFALDQKMRP

0151  STDTITVMVE NSHGLRVRKK EVYMPSSIFQ DDFVIPDISE PGTWKISARF

0201  SDGLESNSST QFEVKKYVLP NFEVKITPGK PYILTVPGHL DEMQLDIQAR

0251  YIYGKPVQGV AYVRFGLLDE DGKKTFFRGL ESQTKLVNGQ SHISLSKAEF

0301  QDALEKLNMG ITDLQGLRLY VAAAIIESPG GEMEEAELTS WYFVSSPFSI

0351  DLSKTKRHKV PGAPFLLQAL VREMSGSPAS GIPVKVSATV SSPGSVPEVQ

0401  DIQQNTDGSG QVSIPIIIPQ TISELQLSVS AGSPHPAIAR LTVAAPPSGG

0451  PGFLSIERPD SRPPRVGDTL NLNLRAVGSG ATFSHYYYMI LSRGQIVFMN

0501  REPKRTLTSV SVFVDHHLAP SFYFVAFYYH GDHPVANSLR VDVQAGACEG

0551  KLELSVDGAK QYRNGESVKL HLETDSLALV ALGALDTALY AAGSKSHKPL

0601  NMGKVFEAMN SYDLGCGPGG GDSALQVFQA AGLAFSDGDQ WTLSRKRLSC

0651  PKEKTTRKKR NVNTQKAINE KLGQYASPTA KRCCQDGVTR LPMMRSCEQR

0701  AARVQQPDCR EPFLSCCQFA ESLRKKSRDK GQAGLQRALE ILQEEDLIDE

0751  DDIPVRSFFP ENWLWRVETV DRFQILTLWL PDSLTTWEIH GLSLSKTKGL

0801  CVATPVQLRV FREFHLHLRL PMSVRRFEQL ELRPVLYNYL DKNITVSVHV

0851  SPVEGLCLAG GGGLAQQVLV PAGSARPVAF SVVPTAAAAV SLKVVARGSF

0901  EFPVGDAVSK VLQIEKEGAI HREELVYELN PLDHRGRTLE IPGNSDPNMI

0951  PDGDFNSYVR VTASDPLDTL GSEGALSPGG VASLLRLPRG CGEQTMIYLA

1001  PTLAASRYLD KTEQWSTLPP ETKDHAVDLI QKGYMRIQQF RKADGSYAAW

1051  LSRDSSTWLT AFVLKVLSLA QEQVGGSPEK LQETSNWLLS QQQADGSFQD

1101  PCPVLDRSMQ GGLVGNDETV ALTAFVTIAL HHGLAVFQDE GAEPLKQRVE

1151  ASISKANSFL GEKASAGLLG AHAAAITAYA LSLTKAPVDL LGVAHNNLMA

1201  MAQETGDNLY WGSVTGSQSN AVSPTPAPRN PSDPMPQAPA LWIETTAYAL

1251  LHLLLHEGKA EMADQASAWL TRQGSFQGGF RSTQDTVIAL DALSAYWIAS

1301  HTTEERGLNV TLSSTGRNGF KSHALQLNNR QIRGLEEELQ FSLGSKINVK

1351  VGGNSKGTLK VLRTYNVLDM KNTTCQDLQI EVTVKGHVEY TMEANEDYED

1401  YEYDELPAKD DPDAPLQPVT PLQLFEGRRN RRREAPKVV EEQESRVHYT

1451  VCIWRNGKVG LSGMAIADVT LLSGFHALRA DLEKLTSLSD RYVSHFETEG

1501  PHYLLYFDSV PTSRECVGFE AVQEVPVGLV QPASATLYDY YNPERRCSVF

1551  YGAPSKSRLL ATLCSAEVCQ CAEGKCPRQR RALERGLQDE DGYRMKFACY

1601  YPRVEYGFQV KVLREDSRAA FRLFETKITQ VLHFTKDVKA AANQMRNFLV

1651  RASCRLRLEP GKEYLIMGLD GATYDLEGHP QYLLDSNSWI EEMPSERLCR

1701  STRQRAACAQ LNDFLQEYGT QGCQV
```

Complement C4-Derived Peptide CO4-1

NGFKSHALQLNNRQIR (SEQ ID NO: 20)

(11) Complement C4-B-derived peptide CO4-1

From the results of MS/MS analysis and MASCOT database search, A sequence of CO4-1 peptide as shown SEQ ID NO: 20 is an amino acid sequence present in the part of topological region that is common to Complement C4-A protein (SEQ ID NO: 19) and Complement C4-B protein. After Biosynthesis, Complement C4-B protein is divided into C4 beta chain, Complement C4-B alpha chain and Complement C4 gamma chain by processing.

SEQ ID NO: 21 is amino acid sequence of intact Complement C4-B protein containing all of these processed peptides.

```
Intact protein/peptide
                                              (SEQ ID NO: 21)
0001   KPRLLLFSPS VVHLGVPLSV GVQLQDVPRG QVVKGSVFLR NPSRNNVPCS
0051   PKVDFTLSSE RDFALLSLQV PLKDAKSCGL HQLLRGPEVQ LVAHSPWLKD
0101   SLSRTTNIQG INLLFSSRRG HLFLQTDQPI YNPGQRVRYR VFALDQKMRP
0151   STDTITVMVE NSHGLRVRKK EVYMPSSIFQ DDFVIPDISE PGTWKISARF
0201   SDGLESNSST QFEVKKYVLP NFEVKITPGK PYILTVPGHL DEMQLDIQAR
0251   YIYGKPVQGV AYVRFGLLDE DGKKTFFRGL ESQTKLVNGQ SHISLSKAEF
0301   QDALEKLNMG ITDLQGLRLY VAAAIIESPG GEMEEAELTS WYFVSSPFSL
0351   DLSKTKRHLV PGAPFLLQAL VREMSGSPAS GIPVKVSAFV SSPGSVPEVQ
0401   DIQQNTDGSG QVSIPIIIPQ TISELQLSVS AGSPHPAIAR LTVAAPPSGG
0451   PGFLSIERPD SRPPRVGDTL NLNLRAVGSG ATFSHYYYMI LSRGQIVFMN
0501   REPKRTLTSV SVFVDHHLAP SFYFVAFYYH GDHPVANSLR VDVQAGACEG
0551   KLELSVDGAK QYRNGESVKL HLETDSLALV ALGALDTALY AAGSKSHKPL
0601   NMGKVFEAMN SYDLGCGPGG GDSALQVFQA AGLAFSDGDQ WTLSRKRLSC
0651   PKEKTTRKKR NVNFQKAINE KLGQYASPTA KRCCQDGVTR LPMMRSCEQR
0701   AARVQQPDCR EPFLSCCQFA ESLRKKSRDK GQAGLQRALE ILQEEDLIDE
0751   DDIPVRSFTP ENWLWRVETV DRFQILTLWL PDSLTTWEIH GLSLSKTKGL
0801   CVATPVQLRV FRETHLFHRL PMSVRRFEQL ELRPVLYNYL DKNLTVSVHV
0851   SPVEGLCLAG GGGLAQQVLV PAGSARPVAF SVVPTAAAAV SLKVVARGSF
0901   EFPVGDAVSK VLQIEKEGAI HREELVYELN PLDHRGRTLE IPGNSDPNMI
0951   PDGDFNSYVR VTASDPLDTL GSEGALSPGG VASLLRLPRG CGEQTMIYLA
1001   PTLAASRYLD KTEQWSTLPP ETKDHAVDLI QKGYMRIQQF RKADGSYAAW
1051   LSRDSSTWLT AFVLKVLSLA QEQVGGSPEK LQETSNWLLS QQQADGSFQD
1101   LSPVIHRSMQ GGLVGNDETV ALTAFVTIAL HHGLAVFQDE GAEPLKQRVE
1151   ASISKANSFL GEKASAGLLG AHAAAITAYA LSLTKAPVDL LGVAHNNLMA
1201   MAQETGDNLY WGSVTGSQSN AVSPTPAPRN PSDPMPQAPA LWIETTAYAL
1251   LHLLLHEGKA EMADQASAWL TRQGSFQGGF RSTQDTVIAL DALSAYWIAS
1301   HTTEERGLNV TLSSTGRNGF KSHALQLNNR QIRGLEEELQ FSLGSKINVK
1351   VGGNSKGTLK VLRTYNVLDM KNTTCQDLQI EVTVKGHVEY TMEANEDYED
1401   YEYDELPAKD DPDAPLQPVT PLQLFEGRRN RRRREAPKVV EEQESRVHYT
1451   VCIWRNGKVG LSGMAIADVF LLSGFHALRA DLEKLTSLSD RYVSHFETEG
1501   PHVLLYFDSV PTSRECVGFE AVQEVPVGLV QPASATLYDY YNPERRCSVF
1551   YGAPSKSRLL ATLCSAEVCQ CAEGKCPRQR RALERGLQDE DGYRMKFACY
```

```
1601  YPRVEYGFQV  KVLREDSRAA  FRLFETKITQ  VLHFTKDVKA  AANQMRNFLV

1651  RASCRLRLEP  GKEYLIMGLD  GATYDLEGHP  QYLLDSNSWI  EEMPSERLCR

1701  STRQRAACAQ  LNDFLQEYGT  QGCQV
```

Just in Case, Following Shows the Sequence of CO4-1.

Complement C4-Derived Peptide CO4-1

```
                                        (SEQ ID NO: 20)
                    NGFKSHALQLNNRQIR
```

(12) Complement C4-A-Derived Peptide CO4-2

Figure 14:
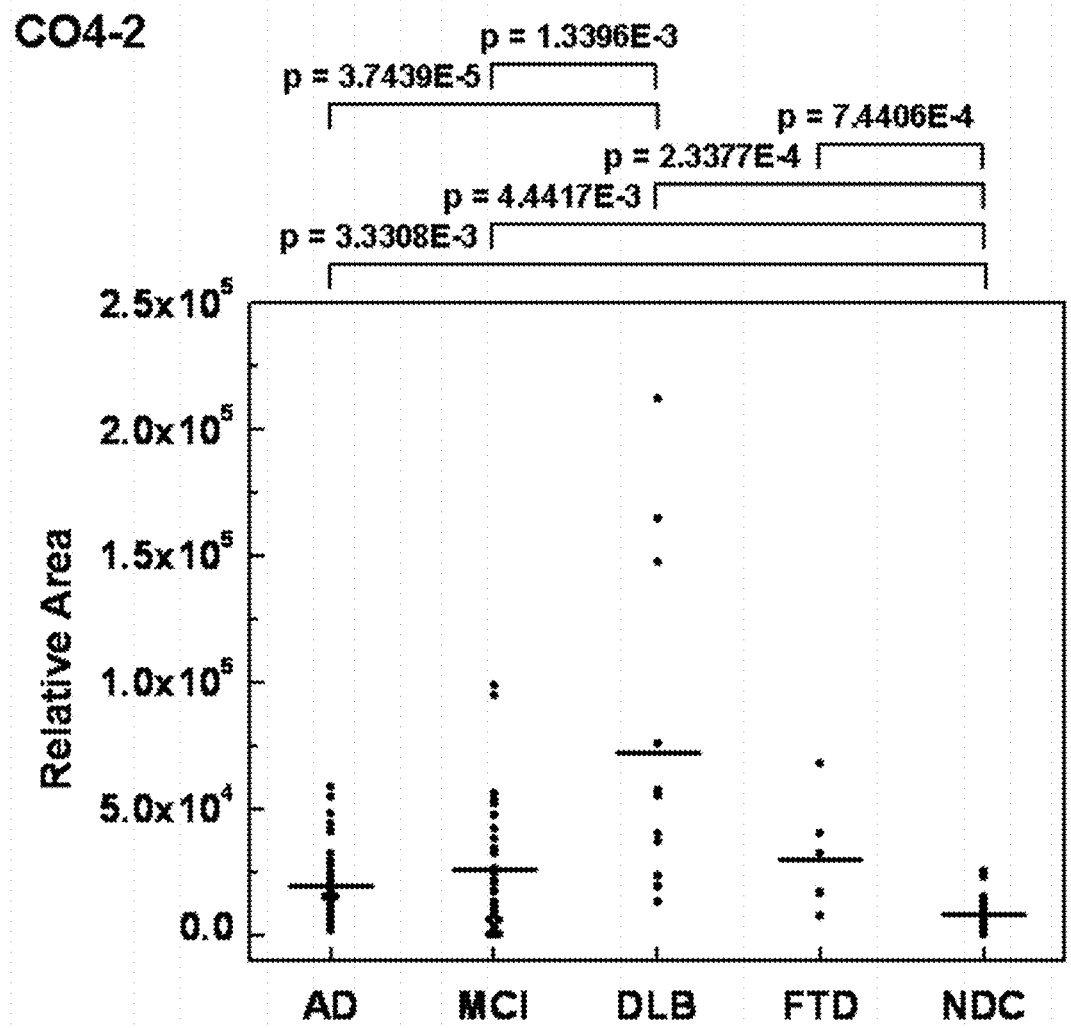
FIG. 14 illustrates the results of differential analysis of CO4-2 expressed by SEQ ID NO: 22. This figure shows a comparison between cognitive impairment patients (AD, MCI, DLB, FTD) and subjects not suffering from psychiatry disease (NDC).

For CO4-2 shown as SEQ ID NO: 22, area values of cognitive impairment (AD, MCI, DLB and FTD) were significantly higher than NDC. (t-test, $p<0.05$) (see FIG. 14)

Thus, it was revealed that CO4-2 shown as SEQ ID NO: 22 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1) After Biosynthesis, Complement C4-A protein is divided into C4 beta chain, Complement C4-A alpha chain and Complement C4 gamma chain by processing.

SEQ ID NO: 19 is amino acid sequence of intact Complement C4-A protein containing all of these processed peptides.

```
Intact protein/peptide
                                        (SEQ ID NO: 19)
0001  KPRLLLFSPS  VVHLGVPLSV  GVQLQDVPRG  QVVKGSVFLR  NPSRNNVPCS

0051  PKVDFTLSSE  RDFALLSLQV  PLKDAKSCGL  HQLLRGPEVQ  LVAHSPWLKD

0101  SLSRTTNIQG  INLLFSSRRG  HLFLQTDQPI  YNPGQRVRYR  VFALDQKMRP

0151  STDTITVMVE  NSHGLRVRKK  EVYMPSSIFQ  DDFVIPDISE  PGTWKISARF

0201  SDGLESNSST  QFEVKKYVLP  NFEVKITPGK  PYILTVPGHL  DEMQLDIQAR

0251  YIYGKPVQGV  AYVRFGLLDE  DGKKTFFRGL  ESQTKLVNGQ  SHISLSKAEF

0301  QDALEKLNMG  ITDLQGLRLY  VAAAIIESPG  GEMEEAELTS  WYFVSSPFSL

0351  DLSKTKRHLV  PGAPFLLQAL  VREMSGSPAS  GIPVKVSATN  SSPGSVPEVQ

0401  DIQQNTDGSG  QVSIPIIIPQ  TISELQLSVS  AGSPHPAIAR  LTVAAPPSGG

0451  PGFLSIERPD  SRPPRVGDTL  NLNLRAVGSG  ATFSHYYYMI  LSRGQIVFMN

0501  REPKRTLTSV  SVFVDHHLAP  SFYFVAFYYH  GDHPVANSLR  VDVQAGACEG

0551  KLELSVDGAK  QYRNGESVKL  HLETDSLALV  ALGALDTALY  AAGSKSHKPL

0601  NMGKVFEAMN  SYDLGCGPGG  GDSALQVFQA  AGLAFSDGDQ  WTLSRKRLSC

0651  PKEKTTRKKR  NVNFQKAINE  KLGQYASPTA  KRCCQDGVTR  LPMMRSCEQR

0701  AARVQQPDCR  EPFLSCCQFA  ESLRKKSRDK  GQAGLQRALE  ILQEEDLIDE

0751  DDIPVRSFFP  ENWLWRVETV  DRFQILTLWL  PDSLTTWEIH  GLSLSKTKGL

0801  CVATPVQLRV  FREFHLHLRL  PMSVRRFEQL  ELRPVLYNYL  DKNLTVSVHV

0851  SPVEGLCLAG  GGGLAQQVLV  PAGSARPVAF  SVVPTAAAAV  SLKVVARGSF

0901  EFPVGDAVSK  VLQIEKEGAI  HREELVYELN  PLDHRGRTLE  IPGNSDPNMI

0951  PDGDFNSYVR  VTASDPLDTL  GSEGALSPGG  VASILRLPRG  CGEQTMIYLA

1001  PTLAASRYLD  KTEQWSTLPP  ETKDHAVDLI  QKGYMRIQQF  RKADGSYAAW

1051  LSRDSSTWLT  AFVLKVLSLA  QEQVGGSPEK  LQETSNWLLS  QQQADGSFQD

1101  PCPVLDRSMQ  GGLVGNDETV  ALTAFVTIAL  HHGLAVFQDE  GAEPLKQRVE

1151  ASISKANSFL  GEKASAGLLG  AHAAAITAYA  LSLTKAPVDL  LGVAHNNLMA

1201  MAQETGDNLY  WGSVTGSQSN  AVSPTPAPRN  PSDPMPQAPA  LWIETTAYAL

1251  LHLLLHEGKA  EMADQASAWL  TRQGSFQGGF  RSTQDTVIAL  DAISAYWIAS

1301  HTTEERGLNV  TLSSTGRNGF  KSHALQLNNR  QIRGLEEELQ  FSLGSKINVK
```

```
1351  VGGNSKGTLK  VLRTYNVLDM  KNTTCQDLQI  EVTVKGHVEY  TMEANEDYED

1401  YEYDELPAKD  DPDAPLQPVT  PLQLFEGRRN  RRRREAPKVV  EEQESRVHYT

1451  VCIWRNGKVG  LSGMAIADVT  LLSGFHALRA  DLEKLTSLSD  RYVSHFETEG

1501  PHVLLYFDSV  PTSRECVGFE  AVQEVPVGLN  QPASATLYDY  YNPERRCSVF

1551  YGAPSKSRLL  ATLCSAEVCQ  CAEGKCPRQR  RALERGLQDE  DGYRMKFACY

1601  YPRVEYGFQV  KVLREDSRAA  FRLFETKITQ  VLHFTKDVKA  AANQMRNFLV

1651  RASCRLRLEP  GKEYLIMGLD  GATYDLEGHP  QYLLDSNSWI  EEMPSERLCR

1701  STRQRAACAQ  LNDFLQEYGT  QGCQV
```

Complement C4-Derived Peptide CO4-2

```
                                                  (SEQ ID NO: 22)
APLQPVTPLQLFEGRRN
```

(13) Complement C4-B-Derived Peptide CO4-2

From the results of MS/MS analysis and MASCOT database search. A sequence of CO4-2 peptide as shown SEQ ID NO: 22 is an amino acid sequence present in the part of topological region that is common to Complement C4-A protein (SEQ ID NO: 19) and Complement C4-B protein. After Biosynthesis, Complement C4-B protein is divided into C4 beta chain, Complement C4-B alpha chain and Complement C4 gamma chain by processing. SEQ ID NO: 21 is amino acid sequence of intact Complement C4-B protein containing all of these processed peptides.

```
Intact protein/peptide
                                                  (SEQ ID NO: 21)
0001  KPRLLLFSPS  VVHLGVPLSV  GVQLQDVPRG  QVVKGSVFLR  NPSRNNVPCS

0051  PKVDFTLSSE  RDFALLSLQV  PLKDAKSCGL  HQLLRGPEVQ  LVAHSPWLKD

0101  SLSRTTNIQG  INLLFSSRRG  HLFLQTDQPI  YNPGQRVRYR  VFALDQKMRP

0151  STDTITVMVE  NSHGLRVRKK  EVYMPSSIFQ  DDFVIPDISE  PGTWKISARF

0201  SDGLESNSST  QFEVKKYVIT  NFEVKITPGK  PYILTVPGHL  DEMQLDIQAR

0251  YIYGKPVQGV  AYVRFGLLDE  DGKKTFFRGL  ESQTKLVNGQ  SHISLSKAEF

0301  QDALEKLNMG  ITDLQGLRLY  VAAAIIESPG  GEMEEAELTS  WYFVSSPFSL

0351  DLSKTKRHLV  PGAPFLLQAL  VREMSGSPAS  GIPVKVSATV  SSPGSVPEVQ

0401  DIQQNTDGSG  QVSIPIIIPQ  TISELQLSVS  AGSPHPAIAR  LTVAAPPSGG

0451  PGFLSIERPD  SRPPRVGDTL  NLNLRAVGSG  ATFSHYYYMI  LSRGQIVFMN

0501  REPKRTLTSV  SVFVDHHLAP  SFYFVAFYYH  GDHPVANSLR  VDVQAGACEG

0551  KLELSVDGAK  QYRNGESVKL  HLETDSLALV  ALGALDTALY  AAGSKSHKPL

0601  NMGKVFEAMN  SYDLGCGPGG  GDSALQVFQA  AGLAFSDGDQ  WTLSRKRLSC

0651  PKEKTTRKKR  NVNFQKAINE  KLGQYASPTA  KRCCQDGVTR  LPMMRSCEQR

0701  AARVQQPDCR  EPFLSCCQFA  ESLRKKSRDK  GQAGLQRALE  ILQEEDLIDE

0751  DDIPVRSFFP  ENWLWRVETV  DRFQILTLWL  PDSLTTWEIH  GLSLSKTKGL

0801  CVATPVQLRV  FREFHLHLRL  PMSVRRFEQL  ELRPVLYNYL  DKNLTVSVHV

0851  SPVEGLCLAG  GGGLAQQVLV  PAGSARPVAF  SVVPTAAAAV  SLKVVARGSF

0901  EFPVGDAVSK  VLQIEKEGAI  HREELVYELN  PLDHRGRTLE  IPGNSDPNMI

0951  PDGDFNSYVR  VTASDPLDTL  GSEGALSPGG  VASLLRLPRG  CGEQTMIYLA

1001  PTLAASRYLD  KTEQWSTLPP  ETKDHAVDLI  QKGYMRIQQF  RKADGSYAAW

1051  LSRDSSTWLT  AFVLKVLSLA  QEQVGGSPEK  LQETSNWLLS  QQQADGSFQD

1101  LSPVIHRSMQ  GGLVGNDETV  ALTAFVTIAL  HHGLAVFQDE  GAEPLKQRVE

1151  ASISKANSFL  GEKASAGLLG  AHAAAITAYA  LSLTKAPVDL  LGVAHNNLMA

1201  MAQETGDNLY  WGSVTGSQSN  AVSPTAPRN  PSDPMPQAPA  LWIETTAYAL
```

```
1251  LHLLLHEGKA  EMADQASAWL  TRQGSFQGGF  RSTQDTVIAL  DALSAYWIAS

1301  HTTEERGLNV  TLSSTGRNGF  KSHALQLNNR  QIRGLEEELQ  FSLGSKINVK

1351  VGGNSKGTLK  VLRTYNVLDM  KNTTCQDLQI  EVTVKGHVEY  TMEANEDYED

1401  YEYDELPAKD  DPDAPLQPVT  PLQLFEGRRN  RRRREAPKVV  EEQESRVHYT

1451  VCIWRNGKVG  LSGMAIADVT  LLSGFHALRA  DLEKLTSLSD  RYVSHFETEG

1501  PHVLLYFDSV  PTSRECVGFE  AVQEVPVGLV  QPASATLYDY  YNPERRCSVF

1551  YGAPSKSRLL  ATLCSAEVCQ  CAEGKCPRQR  RALERGLQDE  DGYRMKFACY

1601  YPRVEYGFQV  KVLREDSRAA  FRLFETKITQ  VLHFTKDVKAAANQMRNFLV

1651  RASCRLRLEP  GKEYLIMGLD  GATYDLEGHP  QYLLDSNSWI  EEMPSERLCR

1701  STRQRAACAQ  LNDFLQEYGT  QGCQV
```

Just in case, following shows the sequence of CO4-2.
Complement C4-Derived Peptide CO4-2

(SEQ ID NO: 22)
APLQPVTPLQLFEGRRN

(14) Fibrinogen Alpha Chain (Isoform 1)-Derived Peptide FIBA-1

Figure 15:
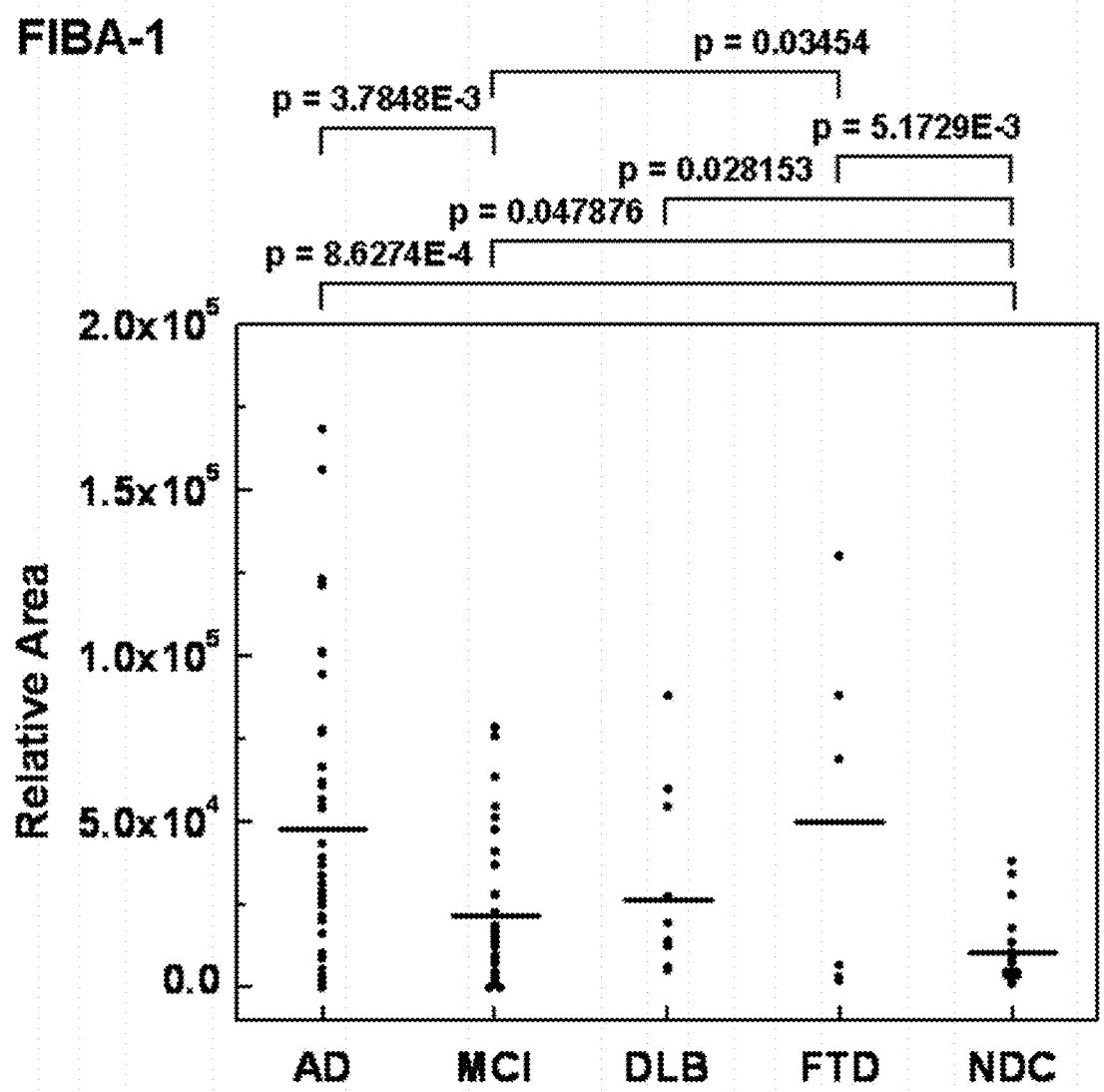
FIG. 15 illustrates the results of differential analysis of FIBA-1 expressed by SEQ ID NO: 24. This figure shows a comparison between cognitive impairment patients (AD, MCI, DLB, FTD) and subjects not suffering from psychiatry disease (NDC).

For FIBA-1 shown as SEQ ID NO: 24, area values of cognitive impairment (AD, MCI, DLB and FTD) were significantly higher than NDC. (t-test, $p<0.05$) (see FIG. 15)

Thus, it was revealed that FIBA-1 shown as SEQ ID NO: 24 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

```
Intact protein/peptide
                                                    (SEQ ID NO: 23)
0001  GPRVVERHQS  ACKDSDWPFC  SDEDWNYKCP  SGCRMKGLID  EVNQDFTNRI

0051  NKLKNSLFEY  QKNNKDSHSL  TTNIMEILRG  DFSSANNRDN  TYNRVSEDLR

0101  SRIEVLKRKV  IEKVQHIQLL  QKNVRAQLVD  MKRLEVDIDI  KIRSCRGSCS

0151  RALAREVDLK  DYEDQQKQLE  QVIAKDLLPS  RDRQHLPLIK  MKPVPDINPG

0201  NFKSQLQKVP  PEWKALTDMP  QMRMELERPG  GNEITRGGST  SYGTGSETES

0251  PRNPSSAGSW  NSGSSGPGST  GNRNPGSSGT  GGTATWKPGS  SGPGSTGSWN

0301  SGSSGTGSTG  NQNPGSPRPG  STGTWNPGSS  ERGSAGHWTS  ESSVSGSTGQ

0351  WHSESGSFRP  DSPGSGNARP  NNPDWGTFEE  VSGNVSPGTR  REYHTEKLVT

0401  SKGDKELRTG  KEKVTSGSTT  TTRRSCSKTV  TKTVIGPDGH  KEVTKEVVTS

0451  EDGSDCPEAM  DLGTLSGIGT  LDGFRHRHPD  EAAFFDTAST  GKTFPGFFSP

0501  MLGEFVSETE  SRGSESGIFT  NTKESSSHHP  GIAEFPSRGK  SSSYSKQFTS

0551  STSYNRGDST  FESKSYKMAD  EAGSEADHEG  THSTKRGHAK  SRPVRDCDDV

0601  LQTHPSGTQS  GIFNIKLPGS  SKIFSVYCDQ  ETSLGGWLLI  QQRMDGSLNF

0651  NRTWQDYKRG  FGSLNDEGEG  EFWLGNDYLH  LLTQRGSVLR  VELEDWAGNE

0701  AYAEYHFRVG  SEAEGYALQV  SSYEGTAGDA  LIEGSVEEGA  EYTSHNNMQF

0751  STFDRDADQW  EENCAEVYGG  GWWYNNCQAA  NLNGIYYPGG  SYDPRNNSPY

0801  EIENGVVWVS  FRGADYSLRA  VRMKIRPLVT  Q
```

Fibrinogen Alpha Chain-Derived Peptide FIBA-1

```
                                              (SEQ ID NO: 24)
              SSSYSKQFTSSTSYNRGDSTFES
```

(15) Fibrinogen Alpha Chain (Isoform 2)-Derived Peptide FIBA-1

From the results of MS/MS analysis and MASCOT database search, A sequence of FIBA-1 peptide as shown SEQ ID NO: 24 is an amino acid sequence present in the part of topological region that is common to Fibrinogen alpha chain (isoform 1) (SEQ ID NO: 23) and Fibrinogen alpha chain isoform 2). Followings, as SEQ ID NO: 25, an amino acid sequence of intact protein of Fibrinogen alpha chain (isoform 2) were shown,

```
Intact protein/peptide
                                                       (SEQ ID NO: 25)
0001    GPRVVERHQS  ACKDSDWPFC  SDEDWNYKCP  SGCRMKGLID  EVNQDFTNRI

0051    NKLKNSLFEY  QKNNKDSHSL  TTNIMEILRG  DFSSANNRDN  TYNRVSEDLR

0101    SRIEVLKRKV  IEKVQHIQLL  QKNVRAQLVD  MKRLEVDIDI  KIRSCRGSCS

0151    RALAREVDLK  DYEDQQKQLE  QVIAKDLLPS  RDRQHLPLIK  MKPVPDLVPG

0201    NFKSQLQKVP  PEWKALTDMP  QMRMELERPG  GNETTRGGST  SYGTGSETES

0251    PRNPSSAGSW  NSGSSGPGST  GNRNPGSSGT  GGTATWKPGS  SGPGSTGSWN

0301    SGSSGTGSTG  NQNPGSPRPG  STGTWNPGSS  ERGSAGHWTS  ESSVSGSTGQ

0351    WHSESGSFRP  DSPGSGNARP  NNPDWGTFEE  VSGNVSPGTR  REYHTEKLVT

0401    SKGDKELRTG  KEKVTSGSTT  TTRRSCSKTV  TKTVIGPDGH  KEVTKEVVTS

0451    EDGSDCPEAM  DLGTLSGIGT  LDGFRHRHPD  EAAFFDTAST  GKTFPGFFSP

0501    MLGEFVSETE  SRGSESGIFT  NTKESSSHHP  GIAEFPSRGK  SSSYSKQFTS

0551    STSYNRGDST  FESKSYKMAD  EAGSEADHEG  THSTKRGHAK  SRPVRGIHTS

0601    PLGKPSLSP
```

Just in case, following shows the sequence of FIBA-1.
Fibrinogen Alpha Chain-Derived Peptide FIBA-1

```
                                              (SEQ ID NO: 24)
              SSSYSKQFTSSTSYNRGDSTFES
```

(16) Fibrinogen Alpha Chain (Isoform 1)-Derived Peptide FIBA-2

Figure 16:
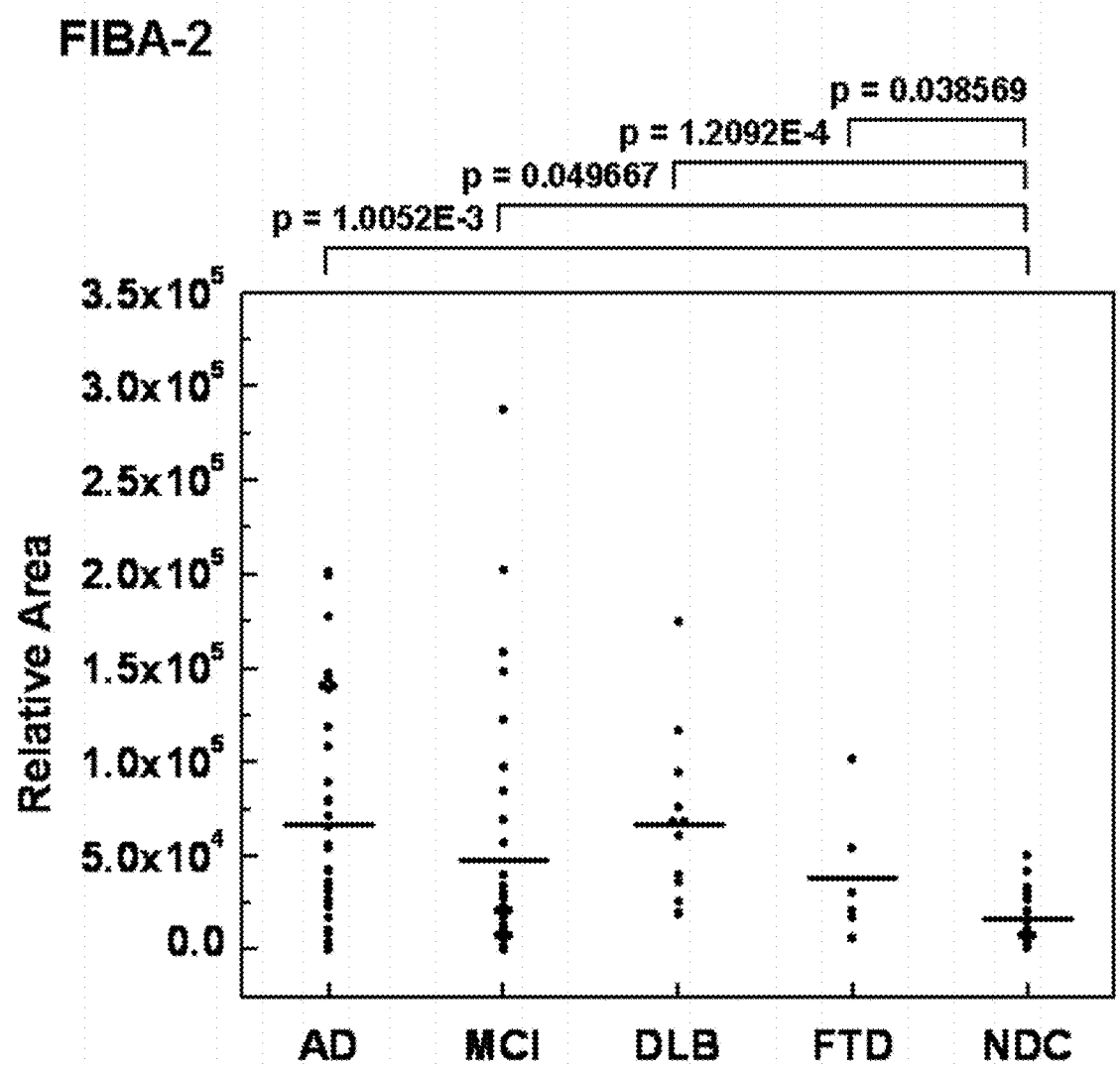
FIG. 16 illustrates the results of differential analysis of FIBA-2 expressed by SEQ ID NO: 26. This figure shows a comparison between cognitive impairment patients (AD, MCI, DLB, FTD) and subjects not suffering from psychiatry disease (NDC).

For FIBA-2 shown as SEQ ID NO: 26, area values of cognitive impairment (AD, MCI, DLB and FTD) were significantly higher than NDC. (t-test, $p<0.05$) (see FIG. 16)

Thus, it was revealed that FIBA-2 shown as SEQ ID NO: 26 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

```
Intact protein/peptide
                                                       (SEQ ID NO: 23)
0001    GPRVVERHQS  ACKDSDWPFC  SDEDWNYKCP  SGCRMKGLID  EVNQDFTNRI

0051    NKLKNSLFEY  QKNNKDSHSL  TTNIMEILRG  DFSSANNRDN  TYNRVSEDLR

0101    SRIEVLKRKV  IEKVQHIQLL  QKNVRAQLVD  MKRLEVDIDI  KIRSCRGSCS

0151    RALAREVDLK  DYEDQQKQLE  QVIAKDLLPS  RDRQHLPLIK  MKPVPDLVPG

0201    NFKSQLQKVP  PEWKALTDMP  QMRMELERPG  GNETTRGGST  SYGTGSETES

0251    PRNPSSAGSW  NSGSSGPGST  GNRNPGSSGT  GGTATWKPGS  SGPGSTGSWN

0301    SGSSGTGSTG  NQNPGSPRPG  STGTWNPGSS  ERGSAGHWTS  ESSVSGSTGQ

0351    WHSESGSFRP  DSPGSGNARP  NNPDWGTFEE  VSGNVSPGTR  REYHTEKLVT

0401    SKGDKELRTG  KEKVTSGSTT  TTRRSCSKTV  TKTVIGPDGH  KEVTKEVVTS
```

```
0451   EDGSDCPEAM DLGTLSGIGT LDGFRHRHPD EAAFFDTAST GKTFPGFFSP

0501   MLGEFVSETE SRGSESGIFT NTKESSSHHP GIAEFPSRGK SSSYSKQFTS

0551   STSYNRGDST FESKSYKMAD EAGSEADHEG THSTKRGHAK SRPVRDCDDV

0601   LQTHPSGTQS GIFNIKLPGS SKIFSVYCDQ ETSLGGWLLI QQRMDGSLNF

0651   NRTWQDYKRG FGSLNDEGEG EFWLGNDYLH LLTQRGSVLR VELEDWAGNE

0701   AYAEYHFRVG SEAEGYALQV SSYEGTAGDA LIEGSVEEGA EYTSHNNMQF

0751   STFDRDADQW EENCAEVYGG GWWYNNCQAA NLNGIYYPGG SYDPRNNSPY

0801   EIENGVVWVS FRGADYSLRA VRMKIRPLVT Q
```

Fibrinogen Alpha Chain-Derived Peptide FIBA-2

(SEQ ID NO: 26)
SSSYSKQFTSSTSYNRGDSTFESKS

(17) Fibrinogen Alpha Chain (Isoform 2)-Derived Peptide FIBA-2

From the results of MS/MS analysis and MASCOT database search, A sequence of FIBA-2 peptide as shown SEQ ID NO: 26 is an amino acid sequence present in the part of topological region that is common to Fibrinogen alpha chain (isoform 1) (SEQ ID NO: 23) and Fibrinogen alpha chain (isoform 2). Followings, as SEQ ID NO: 25, an amino acid sequence of intact protein of Fibrinogen alpha chain (isoform 2) were shown.

```
Intact protein/peptide
                                                     (SEQ ID NO: 25)
0001   GPRVVERHQS ACKDSDWPFC SDEDWNYKCP SGCRMKGLID EVNQDFTNRI

0051   NKLKNSLFEY QKNNKDSHSL TTNIMEILRG DFSSANNRDN TYNRVSEDLR

0101   SRIEVLKRKV IEKVQHIQLL QKNVRAQLVD MKRLEVDIDI KIRSCRGSCS

0151   RALAREVDLK DYEDQQKQLE QVIAKDLLPS RDRQHLPLIK MKPVPDLVPG

0201   NFKSQLQKVP PEWKALTDMP QMRMELERPG GNEITRGGST SYGTGSETES

0251   PRNPSSAGSW NSGSSGPGST GNRNPGSSGT GGTATWKPGS SGPGSTGSWN

0301   SGSSGTGSTG NQNPGSPRPG STGTWNPGSS ERGSAGHWTS ESSVSGSTGQ

0351   WHSESGSFRP DSPGSGNARP NNPDWGIFEE VSGNYSPGTR REYHTEKLVT

0401   SKGDKELRTG KEKVTSGSTT TTRRSCSKTV TKTVIGPDGH KEVTKEVVTS

0451   EDGSDCPEAM DLGTLSGIGT LDGFRHRHPD EAAFFDTAST GKTFPGFFSP

0501   MLGEFVSETE SRGSESGIFT NTKESSSHHP GIAEFPSRGK SSSYSKQFTS

0551   STSYNRGDST FESKSYKMAD EAGSEADHEG THSTKRGHAK SRPVRGIHTS

0601   PLGKPSLSP
```

Just in case, following shows the sequence of FIBA-2.
Fibrinogen Alpha Chain-Derived Peptide FIBA-2

(SEQ ID NO: 26)
SSSYSKQFTSSTSYNRGDSTFESKS

(18) Fibrinogen Alpha Chain (Isoform 1)-Derived Peptide FIBA-3

Figure 17:
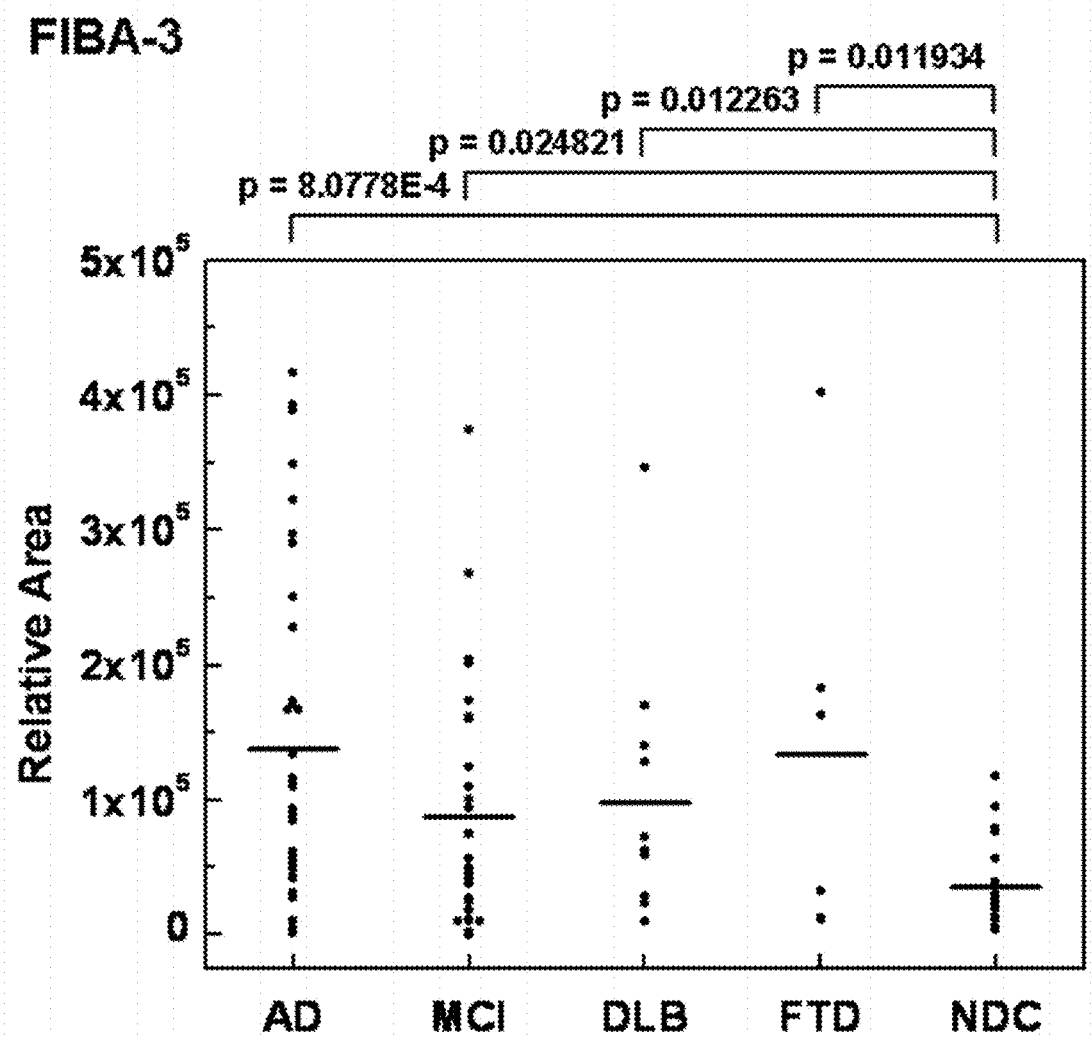
FIG. 17 illustrates the results of differential analysis of FIBA-3 expressed by SEQ ID NO: 27. This figure shows a comparison between cognitive impairment patients (AD, MCI, DLB, FTD) and subjects not suffering from psychiatry disease (NDC).

For FIBA-3 shown as SEQ ID NO: 27, area values of cognitive impairment (AD, MCI, DLB and FTD) were significantly higher than NDC. (t-test, $p<0.05$) (see FIG. 17)

Thus, it was revealed that FMA-3 shown as SEQ ID NO: 27 was useful to distinguish patient of cognitive impairment (AD, MCI, DLB and FTD) with subjects not suffering from psychiatry disease (NDC). According to the analysis by receiver operating characteristic (ROC) curve, CO3 was clearly useful to distinguish AD and MCI with NDC. (See Table 1)

Intact protein/peptide (SEQ ID NO: 23)
```
0001  GPRVVERHQS ACKDSDWPFC SDEDWNYKCP SGCRMKGLID EVNQDFTNRI
0051  NKLKNSLFEY QKNNKDSHSL TTNIMEILRG DFSSANNRDN TYNRVSEDLR
0101  SRIEVLKRKV IEKVQHIQLL QKNVRAQLVD MKRLEVDIDI KIRSCRGSCS
0151  RALAREVDLK DYEDQQKQLE QVIAKDLLPS RDRQHLPLIK MKPVPDLVPG
0201  NFKSQLQKVP PEWKALTDMP QMRMELERPG GNEITRGGST SYGTGSETES
0251  PRNPSSAGSW NSGSSGPGST GNRNPGSSGT GGTATWKPGS SGPGSTGSWN
0301  SGSSGTGSTG NQNPGSPRPG STGTWNPGSS ERGSAGHWTS ESSVSGSTGQ
0351  WHSESGSFRP DSPGSGNARP NNPDWGTFEE VSGNVSPGTR REYHTEKLVT
0401  SKGDKELRTG KEKVTSGSTT TTRRSCSKTV TKTVIGPDGH KEVTKEVVTS
0451  EDGSDCPEAM DLGTLSGIGT LDGFRHRHPD EAAFFDTAST GKTFPGFFSP
0501  MLGEFVSETE SRGSESGIFT NTKESSSHHP GIAEFPSRGK SSSYSKQFTS
0551  STSYNRGDST FESKSYKMAD EAGSEADHEG THSTKRGHAK SRPVRDCDDV
0601  LQTHPSGTQS GIFNIKLPGS SKIFSVYCDQ ETSLGGWLLI QQRMDGSLNF
0651  NRTWQDYKRG FGSLNDEGEG EFWLGNDYLH LLTQRGSVLR VELEDWAGNE
0701  AYAEYHFRVG SEAEGYALQV SSYEGTAGDA LIEGSVEEGA EYTSHNNMQF
0751  STFDRDADQW EENCAEVYGG GWWYNNCQAA NLNGIYYPGG SYDPRNNSPY
0801  EIENGVVWVS FRGADYSLRA VRMKIRPLVT Q
```

Fibrinogen Alpha Chain-Derived Peptide FIBA-3

(SEQ ID NO: 27)
SSSYSKQFTSSTSYNRGDSTFESKSY

(19) Fibrinogen Alpha Chain (Isoform 2)-Derived Peptide FIBA-3

From the results of MS/MS analysis and MASCOT database search, A sequence of FIBA-3 peptide as shown SEQ ID NO: 27 is an amino acid sequence present in the part of topological region that is common to Fibrinogen alpha chain (isoform 1) (SEQ ID NO: 23) and Fibrinogen alpha chain (isoform 2). Followings, as SEQ ID NO: 25, an amino acid sequence of intact protein of Fibrinogen alpha chain (isoform 2) were shown.

Intact protein/peptide (SEQ ID NO: 25)
```
0001  GPRVVERHQS ACKDSDWPFC SDEDWNYKCP SGCRMKGLID EVNQDFTNRI
0051  NKLKNSLFEY QKNNKDSHSL TTNIMEILRG DFSSANNRDN TYNRVSEDLR
0101  SRIEVLKRKV IEKVQHIQLL QKNVRAQLVD MKRLEVDIDI KIRSCRGSCS
0151  RALAREVDLK DYEDQQKQLE QVIAKDLLPS RDRQHLPLIK MKPVPDLVPG
0201  NFKSQLQKVP PEWKALTDMP QMRMELERPG GNEITRGGST SYGTGSETES
0251  PRNPSSAGSW NSGSSGPGST GNRNPGSSGT GGTATWKPGS SGPGSTGSWN
0301  SGSSGTGSTG NQNPGSPRPG STGTWNPGSS ERGSAGHWTS ESSVSGSTGQ
0351  WHSESGSFRP DSPGSGNARP NNPDWGTFEE VSGNVSPGTR REYHTEKLVT
0401  SKGDKELRTG KEKVTSGSTT TTRRSCSKTV TKTVIGPDGH KEVIKEVVTS
0451  EDGSDCPEAM DLGTLSGIGT LDGFRHRHPD EAAFFDTAST GKTFPGFFSP
0501  MLGEFVSETE SRGSESGIFT NTKESSSHHP GIAEFPSRGK SSSYSKQFTS
0551  STSYNRGDST FESKSYKMAD EAGSEADHEG THSTKRGHAK SRPVRGIHTS
0601  PLGKPSLSP
```

Just in case, following shows the sequence of FIBA-3.
Fibrinogen Alpha Chain-Derived Peptide FIBA-3

(SEQ ID NO: 27)
SSSYSKQFTSSTSYNRGDSTFESKSY

TABLE 1

| Marker Peptide | | AD vs. NDC | MCI vs. NDC |
|---|---|---|---|
| Sequence No. | Sequence name | AUC value | AUC value |
| 2 | CO3 | 0.88 | 0.83 |
| 4 | AP2C | 0.78 | 0.70 |
| 6 | SYN3 | 0.77 | 0.77 |
| 8 | OXYR | 0.81 | 0.77 |
| 10 | ITH5L | 0.79 | 0.70 |
| 12 | HERC2 | 0.76 | 0.73 |
| 14 | THRB | 0.85 | 0.79 |
| 16 | TTHY | 0.73 | 0.69 |
| 18 | TNR16 | 0.75 | 0.74 |
| 20 | CO4-1 | 0.73 | 0.67 |
| 22 | CO4-2 | 0.76 | 0.74 |
| 24 | FIBA-1 | 0.77 | 0.64 |
| 26 | FIBA-2 | 0.74 | 0.61 |
| 27 | FIBA-3 | 0.80 | 0.64 |

Table 1 shows AUC values obtained by the analysis by receiver operating characteristic (ROC) curve in the detection of cognitive impairment of each marker peptides.

Using these marker peptides in singly or in combination, using or without using liquid chromatography and/or any other suitable separation methods, directly measuring the abundance in serum using other methods such as mass spectrometry or immunological methods or enzymatic methods, on the diagnosis, it is possible to distinguish between non-psychiatry disease subjects including normal healthy subjects and subjects of cognitive impairment like AD, MCI, DLB and FTD.

INDUSTRIAL APPLICABILITY

By using the biomarkers disclosed in the present invention, mild cognitive impairment and cognitive impairment including Alzheimer disease can be detected. This invention is applicable to the field of medical diagnostics including diagnostic reagent.

Sequence List
10P01009_Sequence.txt

The invention claimed is:

1. A method of diagnosing and treating Alzheimer's dementia, mild cognitive impairment, Dementia with Lewy bodies or frontotemporal dementia in a patient, said method comprising:
   a) obtaining a biological material sample from a human patient;
   b) detecting an amount of Prothrombin-derived peptide THRB consisting of SEQ NO: 14 in the biological material sample by mass spectrometry;
   c) diagnosing the patient with said Alzheimer's dementia, mild cognitive impairment, Dementia with Lewy bodies or frontotemporal dementia when a higher amount of the Prothrombin-derived peptide THRB in the biological material sample is detected by comparing the amount of the Prothrombin-derived peptide THRB in the patient with an amount of the Prothrombin-derived peptide THRB in a biological material sample obtained from a non-psychiatry disease subject; and
   d) administering an effective amount of an anti-acetylcholine esterase inhibitor to the diagnosed patient.

2. The method of claim 1, wherein the biological material is serum, blood, plasma, cerebrospinal fluid, or urine.

3. The method of claim 1, wherein the anti-acetylcholine esterase is Donepezil-hydrochloride.

* * * * *